United States Patent
Zhang et al.

(10) Patent No.: US 12,258,365 B2
(45) Date of Patent: Mar. 25, 2025

(54) ORGANOPHOSPHORUS-SUBSTITUTED COMPOUNDS AS C-MET INHIBITORS AND THERAPEUTIC USES THEREOF

(71) Applicant: BETA PHARMA, INC., Wilmington, DE (US)

(72) Inventors: Don Zhang, Princeton, NJ (US); Jirong Peng, Mequon, WI (US); Michael Nicholas Greco, Lansdale, PA (US); Michael John Costanzo, Warminster, PA (US); Michael Alan Green, Easton, PA (US)

(73) Assignee: BETA PHARMA, INC., Wilmington, DE (US)

( * ) Notice: Subject to any disclaimer, the term of this patent is extended or adjusted under 35 U.S.C. 154(b) by 822 days.

(21) Appl. No.: 17/312,669

(22) PCT Filed: Dec. 14, 2019

(86) PCT No.: PCT/US2019/066414
§ 371 (c)(1),
(2) Date: Jun. 10, 2021

(87) PCT Pub. No.: WO2020/124060
PCT Pub. Date: Jun. 18, 2020

(65) Prior Publication Data
US 2022/0064194 A1 Mar. 3, 2022

Related U.S. Application Data

(60) Provisional application No. 62/779,960, filed on Dec. 14, 2018.

(51) Int. Cl.
*C07F 9/6561* (2006.01)
*A61K 31/675* (2006.01)
*A61P 35/00* (2006.01)

(52) U.S. Cl.
CPC .......... *C07F 9/6561* (2013.01); *A61K 31/675* (2013.01); *A61P 35/00* (2018.01)

(58) Field of Classification Search
CPC .... C07F 9/6561; C07F 9/5004; C07F 9/3211; A61P 35/00; A61K 31/675; C07D 487/04
See application file for complete search history.

(56) References Cited

U.S. PATENT DOCUMENTS

| | | | |
|---|---|---|---|
| 9,242,991 B2 | 1/2016 | Hu et al. | |
| 2011/0039856 A1* | 2/2011 | Collman | A61P 35/02 |
| | | | 514/249 |
| 2015/0218171 A1 | 8/2015 | Zhong et al. | |
| 2015/0315210 A1 | 11/2015 | Hu et al. | |

FOREIGN PATENT DOCUMENTS

| | | |
|---|---|---|
| WO | 2007075567 A1 | 7/2007 |
| WO | 2007132308 A1 | 11/2007 |
| WO | 2010019899 A1 | 2/2010 |
| WO | 2011079804 A1 | 7/2011 |

OTHER PUBLICATIONS

Ahn et al., 2017, Increased HGF Expression Induces Resistance to c-MET tyrosine Kinase Inhibitors in Gastric Cancer, Anticancer Research, 37, 1127-1138 (Year: 2017).*
Extended European Search Report for European Applicatio No. 19897455.2, Date of Mailing Jul. 8, 2022, 7 pages.
Jia, H. et al., "Discovery of (S)-1-(1-(Imidazo[1,2-a]pyridin-6-yl)ethyl)-6-(1-methyl-1H-pyrazol-4-yl)-1H-[1,2,3]triazolo[4,5-b]pyrazine (Volitinib) as a Highly Potent and Selective Mesenchymal-Epithelial Transition Factor (c-Met) Inhibitor In Clinical Development for Treatment of Cancer", Journal of Medicinal Chemistry, vol. 57; Published: Aug. 22, 2014; pp. 7577-7589.
Van Veggel, B. et al., "Crizotinib treatment for patients with EGFR mutation positive NSCLC that acquire cMET amplification after EGFR TKI therapy results in short-lived and heterogeneous responses", Lung Cancer, vol. 124, 2018; pp. 130-134.
Berge et al.; "Pharmaceutical Salts"; Journal of Pharmaceutical Sciences; 66(1); 1-19; (1977).
International Search Report mailed Apr. 6, 2020; International Application No. PCT/US2019/066414; International Filing Date Dec. 14, 2019 (4 pgs).
Written Opinion mailed Apr. 6, 2020; International Application No. PCT/US2019/066414; International Filing Date Dec. 14, 2019 (5 pgs).

* cited by examiner

*Primary Examiner* — Juliet C Switzer
*Assistant Examiner* — Dawanna Shar-Day White
(74) *Attorney, Agent, or Firm* — CANTOR COLBURN LLP

(57) ABSTRACT

The present disclosure provides [1,2,4]triazolo[4,3-b][1,2,4]triazine, [1,2,4] triazolo[4,3-b]pyridazine, and [1,2,3]triazolo[4,5-b]pyrazine derivatives, and pharmaceutically acceptable salts, solvates or prodrugs thereof, as tyrosine kinase c-MET inhibitors, which are useful as novel anticancer and/or anti-inflammatory agents.

30 Claims, No Drawings

ORGANOPHOSPHORUS-SUBSTITUTED COMPOUNDS AS C-MET INHIBITORS AND THERAPEUTIC USES THEREOF

CROSS-REFERENCE TO RELATED APPLICATIONS

This application is a U.S. National Stage Application of PCT/US2019/066414, filed on Dec. 14, 2019, which claims priority to U.S. Provisional Application No. 62/779,960, filed on Dec. 14, 2018, the disclosures of each of which are incorporated herein by reference in their entirety.

FIELD OF THE INVENTION

The present invention is related to the field of compounds, compositions and methods for the treatment or prevention of a disease, disorder, or medical condition mediated through certain kinases, especially the receptor tyrosine kinase c-MET. The diseases include various cancers.

BACKGROUND OF THE INVENTION c-MET (Mesenchymal-Epithelial Transcription factor) is a unique receptor tyrosine kinase, existing as a 190 kDa transmembrane heterodimer proto-oncogene that encodes the receptor for its endogenous ligand, hepatocyte growth factor (HGF). Binding between HGF and c-MET results in the activation of a variety of cellular processes, such as cell proliferation, survival, morphogenesis, motility, invasion, apoptosis and angiogenesis. Dysregulated c-MET/HGF signaling has been implicated in a wide range of malignancies such as breast cancer, non-small cell lung cancer, gastric cancer, hepatocellular cancer, melanoma, pancreatic cancer, esophageal cancer, colorectal cancers, ovarian cancers, glioblastomas and various blood cancers. Consequently, targeting the c-MET signaling pathway represents a promising target for the treatment of various cancers, and there remains a need to develop new c-MET inhibitors as novel anticancer and/or anti-inflammatory agents. c-MET amplification has been linked to the development of acquired resistance to agents that target various epidermal growth factors. The compounds of this invention are inhibitors of c-MET kinase and thus represent potential therapeutic agents for the treatment of various cancers.

Recently, several types of benzo-fused triazole derivatives have been reported to be c-MET inhibitors (e.g. WO 2011/079804, WO 2007/075567, and WO 2010/019899). There remains an urgent need to develop new c-MET inhibitors as novel anticancer and/or anti-inflammatory agents.

SUMMARY OF THE INVENTION

The present invention provides phosphorus-containing derivatives of [1,2,4]triazolo[4,3-b][1,2,4]triazine, [1,2,4]triazolo[4,3-b]pyridazine, and [1,2,3]triazolo[4,5-b]pyrazine, or the like, in which the 6-aryl or 6-heteroaryl moiety R contains a phosphorous substituent and W-Het is a linked fused bicyclic heterocycle as depicted in structures A, B, and C.

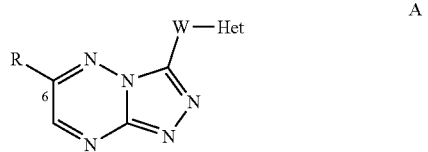

A

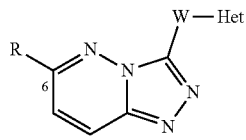

B

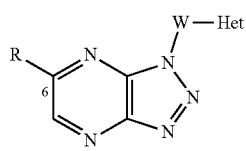

C

These compounds are effective as c-MET inhibitors and useful in the treatment or prevention of diseases, disorders, or medical conditions mediated through certain c-MET signaling pathways, such as various types of cancers.

One aspect of the present invention is directed to a compound of formula I:

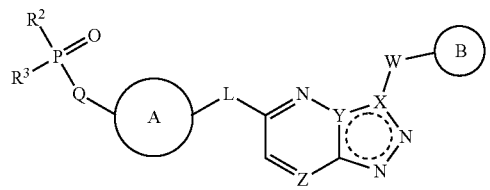

I or a pharmaceutically acceptable salt, solvate, or prodrug thereof, as defined herein below.

In another aspect, the present invention provides a pharmaceutical composition comprising a compound of formula (I), or a pharmaceutically acceptable salt, solvate or prodrug thereof, and a pharmaceutically acceptable carrier.

In another aspect, the present invention provides a method of treating a disease or disorder associated with tyrosine kinase c-MET activity in a subject, comprising administering to the subject a therapeutically effective amount of a compound of formula (I), or a pharmaceutically acceptable salt, solvate, or prodrug thereof, or a pharmaceutical composition comprising a compound of formula (I) or a pharmaceutically acceptable salt, solvate, or prodrug thereof.

In another aspect, the present invention provides use of a compound of formula (I), or a pharmaceutically acceptable salt, solvate or prodrug thereof, in the manufacture of a medicament for treatment of a disease or disorder associated with a tyrosine kinase c-MET activity.

The disease or disorder sometimes preferably is selected from the group consisting of gastric cancer, lung cancer (e.g., non-small cell lung cancer), colon cancer, breast cancer, pancreatic cancer, esophageal cancer, colorectal cancers, ovarian cancers, glioblastomas, hepatocellular cancer, melanoma, and other solid tumors.

DETAILED DESCRIPTION OF CERTAIN EMBODIMENTS

In one aspect, the present invention provides a compound of formula (I):

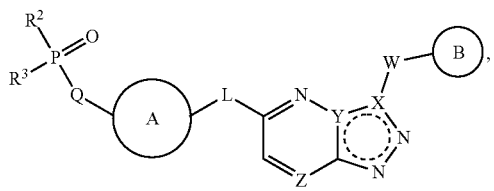

or a pharmaceutically acceptable salt, solvate, or prodrug thereof, wherein:

A is absent (i.e., a direct bond), arylene or heteroarylene, each optionally substituted by one to four substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, hydroxy, $C_1$-$C_6$ acyl, cyano, nitro, and $NR^cR^d$;

L is absent (i.e., a direct bond), O, S, $NR^1$, C(O), or $C(R^L)_2$, wherein $R^L$ at each occurrence is independently hydrogen, halogen, or $C_1$-$C_4$ alkyl;

Q is absent (i.e., a direct bond) or $C(R^Q)_2$, wherein $R^Q$ at each occurrence is independently hydrogen, halogen, $C_1$-$C_4$ alkyl, $C_1$-$C_4$ haloalkyl, $C_1$-$C_4$ alkoxy, or $C_1$-$C_4$ haloalkoxy;

X and Y are each C or N;

Z is $CR^Z$ or N, wherein $R^Z$ is hydrogen, halogen, $C_1$-$C_4$ alkyl, $C_1$-$C_4$ haloalkyl, $C_1$-$C_4$ alkoxy, or $C_1$-$C_4$ haloalkoxy;

when X is C and Y is N, then W is O, $NR^1$, S, or $CR^5R^6$;

when X is N, then W is $CR^5R^6$;

$R^1$ is H or $C_1$-$C_6$ alkyl;

$R^2$ and $R^3$ are each independently alkyl, aryl, cycloalkyl, heteroaryl, heterocyclyl, —$OR^4$, —$NR^7R^8$, or —$OCH_2$ (C=O)$OR^9$, wherein said alkyl, aryl, cycloalkyl, heteroaryl, or heterocyclyl is each optionally substituted by one to five substituents independently selected from the group consisting of $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —C(O)$OR^9$, —C(O)$R^{10}$, —$NR^aR^b$, and —C(O)$NR^cR^d$; or alternatively $R^2$ and $R^3$ together with the phosphorus atom to which they are attached form a 4- to 8-membered ring optionally substituted with one to five substituents independently selected from the group consisting of $C_1$-$C_6$ alkyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —C(O)$OR^9$, —C(O)$R^{10}$, —$NR^aR^b$, —C(O)$NR^cR^d$, and oxo;

$R^4$ at each occurrence is independently hydrogen, alkyl, cycloalkyl, aryl, heteroaryl, heterocyclyl, or arylalkyl, each except hydrogen optionally substituted;

$R^5$ and $R^6$ are each independently selected from H, halogen, $C_1$-$C_6$ alkyl, and $C_1$-$C_6$ alkoxy; or $R^5$ and $R^6$ together form oxo (=O) or with the carbon atom to which they are attached form a 3- to 6-membered ring optionally substituted by one to five substituents independently selected from the group consisting of halogen, $C_1$-$C_6$ alkyl, and $C_1$-$C_6$ alkoxy;

$R^7$ and $R^8$ are independently selected from hydrogen, $C_1$-$C_6$ alkyl, $C_3$-$C_6$ cycloalkyl, $C_6$-$C_{10}$ aryl, 5- to 10-membered heteroaryl, and 5- to 10-membered heterocyclyl; or alternatively, $R^7$ and $R^8$ together with the nitrogen atom to which they are attached, form a 4- to 6-membered ring, wherein said 4- to 6-membered ring optionally may contain one to five substituents independently selected from the group consisting of halogen, $C_1$-$C_6$ alkyl, $C_1$-$C_6$ haloalkyl, $C_6$-$C_{10}$ aryl, and —$OR^9$;

B is aryl, heteroaryl, cycloalkyl, or heterocyclyl, each optionally substituted with one or more, sometimes preferably one to five, sometimes more preferably one to three, substituents independently selected from the group consisting of halogen, $C_1$-$C_6$ alkyl, $C_1$-$C_6$ haloalkyl, $C_2$-$C_6$ alkenyl, $C_3$-$C_6$ cycloalkyl, $C_6$-$C_{10}$ aryl, 5- to 10-membered heteroaryl, 3- to 10-membered heterocyclyl, CN, P(=O)($R^9$)$_2$, P(=O)($OR^9$)$_2$, —C(O)$R^{10}$, —$CO_2R^9$, —$OR^9$, —$SR^9$, —$NR^aR^b$, —$CONR^aR^b$, —$NR^{12}C(O)R^{10}$, —$NR^{12}SO_2R^{11}$, —$NR^{12}SO_2NR^aR^b$, —$SO_2R^{11}$, and —$SO_2NR^aR^b$;

$R^9$ at each occurrence is independently hydrogen, $C_1$-$C_6$ alkyl, or $C_6$-$C_{10}$ aryl;

$R^{10}$ at each occurrence is independently hydrogen, $C_1$-$C_6$ alkyl, $C_1$-$C_6$ haloalkyl, $C_3$-$C_6$ cycloalkyl, $C_6$-$C_{10}$ aryl, or 5- to 10-membered heteroaryl, each except hydrogen optionally substituted;

$R^{11}$ at each occurrence is independently selected from the group consisting of $C_1$-$C_6$ alkyl, $C_3$-$C_6$ cycloalkyl, $C_6$-$C_{10}$ aryl, and 5- to 10-membered heteroaryl, each optionally substituted;

$R^{12}$ each occurrence is independently hydrogen, $C_1$-$C_6$ alkyl, or $C_3$-$C_6$ cycloalkyl;

wherein, unless specifically defined, cycloalkyl and heterocyclyl may optionally be fused onto an aromatic ring and may optionally be substituted with one to five substituents independently selected from the group consisting of halogen, cyano, nitro, —$OR^{13}$, —$SR^{13}$, $C_1$-$C_6$ alkyl, $C_6$-$C_{10}$ aryl, —$NR^aR^b$, and —C(O)$OR^{14}$;

wherein, unless specifically defined, any said aryl and heteroaryl may optionally be substituted with one to five substituents independently selected from halogen, cyano, nitro, —$OR^{13}$, —$SR^{13}$, $C_1$-$C_6$ alkyl, $C_1$-$C_6$ haloalkyl, $C_6$-$C_{10}$ aryl, —C(O)$OR^{14}$, —$NR^aR^b$, and —C(O)$NR^cR^d$;

$R^{13}$ at each occurrence is independently hydrogen, $C_1$-$C_6$ alkyl, or $C_1$-$C_6$ haloalkyl;

$R^{14}$ at each occurrence is independently hydrogen or $C_1$-$C_6$ alkyl;

$R^a$ and $R^b$ are independently selected from hydrogen, $C_1$-$C_6$ alkyl, $C_3$-$C_6$ cycloalkyl, $C_6$-$C_{10}$ aryl, 5- to 10-membered heteroaryl, and benzyl; and $R^c$ and $R^d$ are independently hydrogen or $C_1$-$C_6$ alkyl.

In one embodiment, the present invention provides a compound of formula (I), wherein X is N, Y is C, and Z is N, having a structure of formula (II):

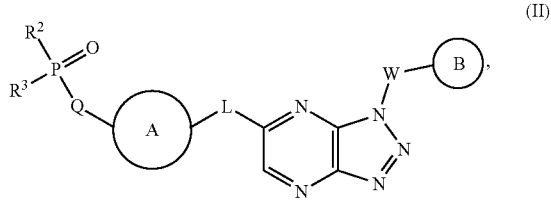

or a pharmaceutically acceptable salt, solvate, or prodrug thereof.

In another embodiment, the present invention provides a compound of formula (I), wherein X is C, Y is N, and Z is CH, having a structure of formula (III):

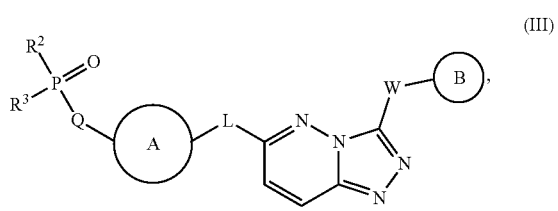

(III)

or a pharmaceutically acceptable salt, solvate, or prodrug thereof.

In another embodiment, the present invention provides a compound of formula (I), wherein X is C, Y is N, and Z is N, having a structure of formula (IV):

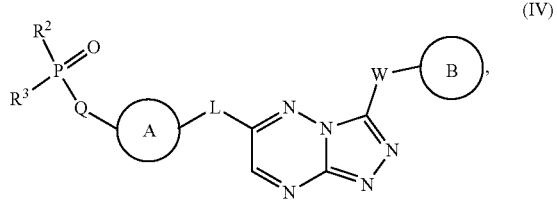

(IV)

or a pharmaceutically acceptable salt, solvate, or prodrug thereof.

In another embodiment, the present invention provides a compound according to any one of formula (I), (II), (III), or (IV), or a pharmaceutically acceptable salt, solvate, or prodrug thereof, wherein A is arylene or heteroarylene each optionally substituted by one or more, sometimes preferably one to four, sometimes more preferably one to three, substituents independent selected from the group consisting of halogen, $C_1$-$C_6$ alkyl, $C_1$-$C_6$ alkoxy, $C_1$-$C_6$ haloalkyl, and $C_1$-$C_6$ haloalkoxy.

In another embodiment, the present invention provides a compound according to any one of formula (I), (II), (III), or (IV), or a pharmaceutically acceptable salt, solvate, or prodrug thereof, wherein A is selected from the group consisting of:

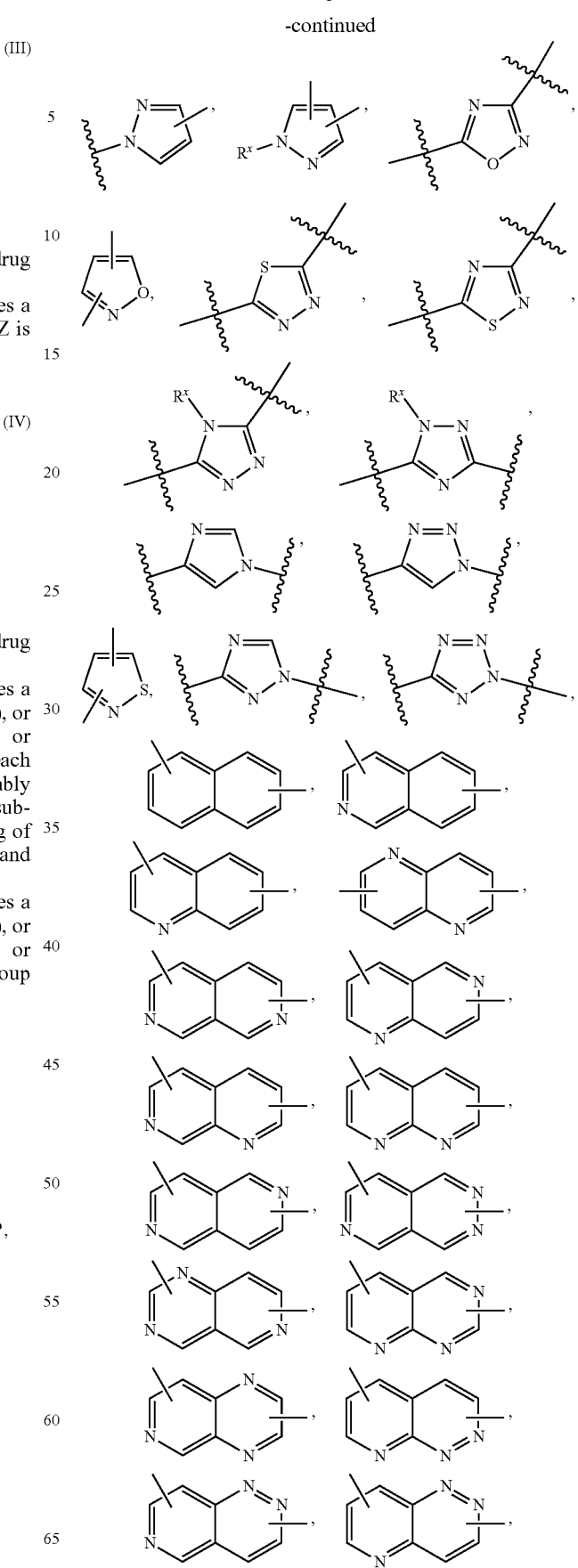

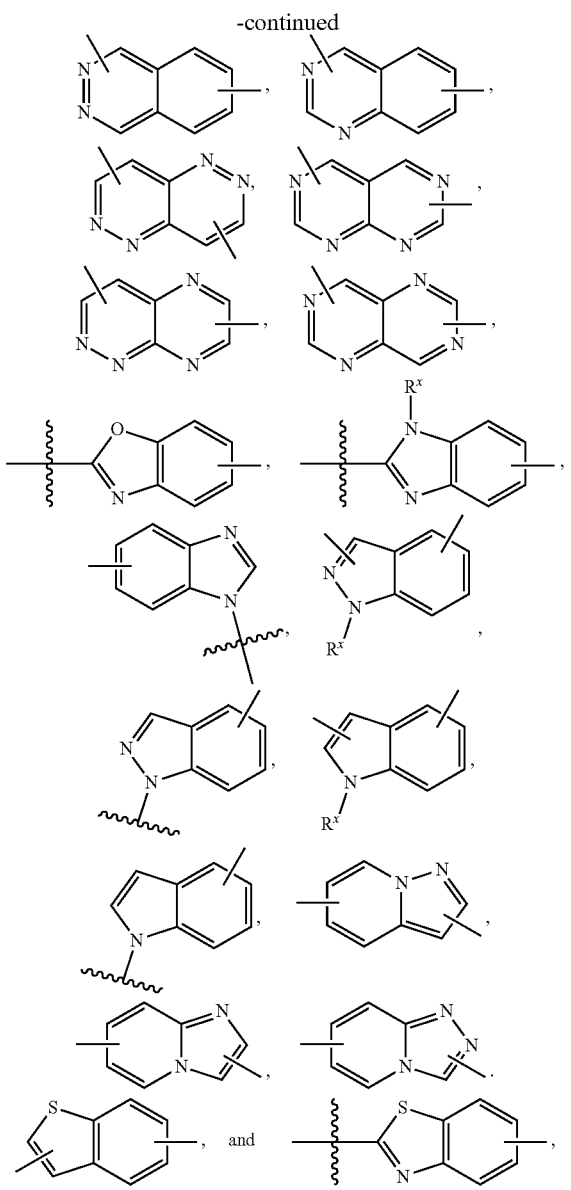

each optionally substituted by one, two, or three substituents independently selected from the group consisting of halogen, $C_1$-$C_4$ alkyl, $C_1$-$C_4$ alkoxy, $C_1$-$C_4$ haloalkyl, and $C_1$-$C_4$ haloalkoxy.

In another embodiment, the present invention provides a compound according to any one of formula (I), (II), (III), or (IV), or a pharmaceutically acceptable salt, solvate, or prodrug thereof, wherein L is absent or $NR^1$, and Q is absent or $C(R^Q)_2$.

In another embodiment, the present invention provides a compound according to any one of formula (I), (II), (III), or (IV), or a pharmaceutically acceptable salt, solvate, or prodrug thereof, wherein L is absent, and Q is $C(R^Q)_2$.

In another embodiment, the present invention provides a compound according to any one of formula (I), (II), (III), or (IV), or a pharmaceutically acceptable salt, solvate, or prodrug thereof, wherein L is $NR^1$, and Q is $C(R^Q)_2$.

In another embodiment, the present invention provides a compound according to any one of formula (I), (II), (III), or (IV), or a pharmaceutically acceptable salt, solvate, or prodrug thereof, wherein L is $NR^1$, and Q is absent.

In another embodiment, the present invention provides a compound according to any one of formula (I), (II), (III), or (IV), or a pharmaceutically acceptable salt, solvate, or prodrug thereof, wherein L and Q are absent.

In another embodiment, the present invention provides a compound according to any one of formula (I), (II), (III), or (IV), or a pharmaceutically acceptable salt, solvate, or prodrug thereof, wherein A, L, and Q are all absent.

In another embodiment, the present invention provides a compound according to any one of formula (I), (II), (III), or (IV), or a pharmaceutically acceptable salt, solvate, or prodrug thereof, wherein B is heteroaryl or heterocyclyl, each optionally substituted with one to three substituents independently selected from the group consisting of halogen, CN, $C_1$-$C_6$ alkyl, $C_1$-$C_6$ haloalkyl, —C(O)$R^{10}$, —$CO_2R^9$, —$OR^9$, —$NR^aR^b$, —C(O)$NR^aR^b$, and —$SO_2NR^aR^b$, wherein $R^9$ is hydrogen or $C_1$-$C_6$ alkyl, $R^{10}$ is $C_1$-$C_4$ alkyl, and $R^a$ and $R^b$ are each independently hydrogen or $C_1$-$C_4$ alkyl.

In another embodiment, the present invention provides a compound according to any one of formula (I), (II), (III), or (IV), or a pharmaceutically acceptable salt, solvate, or prodrug thereof, wherein B is selected from the group consisting of:

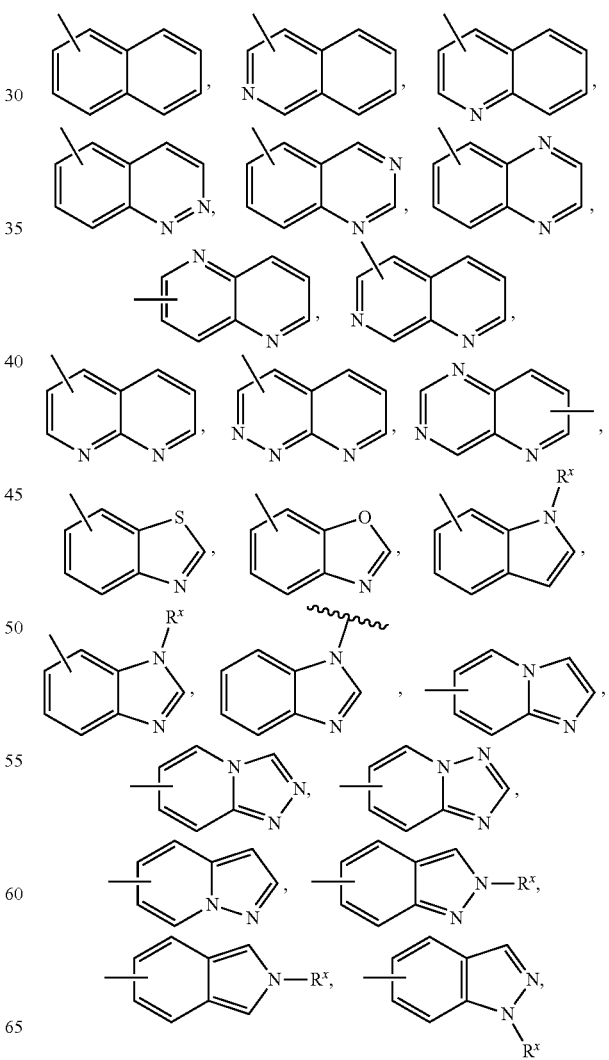

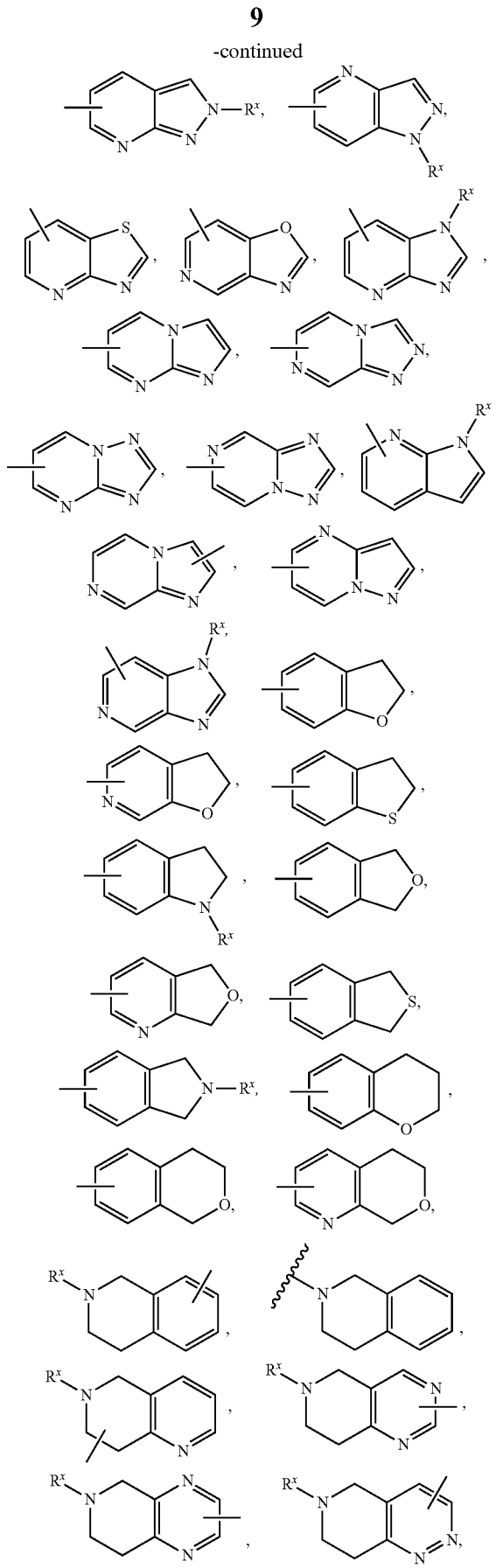

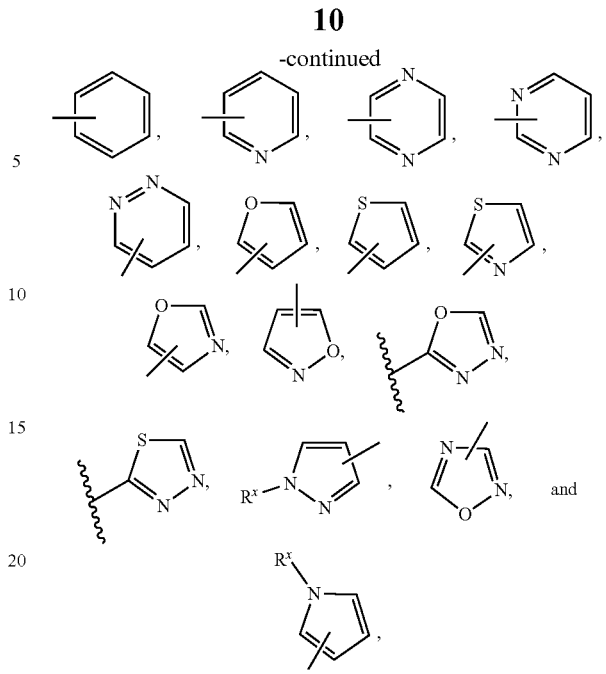

each optionally substituted by one, two, or three substituents independently selected from the group consisting of halogen, $C_1$-$C_6$ alkyl, $C_1$-$C_6$ alkoxy, $C_1$-$C_6$ haloalkyl, and $C_1$-$C_6$ haloalkoxy.

In another embodiment, the present invention provides a compound according to any one of formula (I), (II), (III), or (IV), or a pharmaceutically acceptable salt, solvate, or prodrug thereof, wherein W is $C(R^5R^6)$, wherein $R^5$ and $R^6$ are each independently H, halogen, or $C_1$-$C_4$ alkyl.

In another embodiment, the present invention provides a compound according to any one of formula (I), (II), (III), or (IV), wherein $R^2$ and $R^3$ are independently selected from the group consisting of $C_1$-$C_6$ alkyl, $C_3$-$C_6$ cycloalkyl, —$OR^4$, —$NR^7R^8$, and —$OCH_2(C=O)OR^9$, wherein the alkyl or cycloalkyl is optionally substituted by one to four, sometimes preferably one to three, sometimes, more preferably one to two, substituents independently selected from the group consisting of $C_1$-$C_4$ alkyl, $C_2$-$C_4$ alkenyl, $C_2$-$C_4$ alkynyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —$C(O)OR^9$, —$C(O)R^{10}$, —$NR^aR^b$, and —$C(O)NR^cR^d$; and wherein:

$R^4$ is selected from the group consisting of hydrogen, $C_1$-$C_6$ alkyl, and benzyl;

$R^7$ and $R^8$ are independently selected from hydrogen, $C_1$-$C_6$ alkyl, $C_3$-$C_6$ cycloalkyl, and $C_6$-$C_{10}$ aryl; or alternatively, $R^7$ and $R^8$ together with the nitrogen atom to which they are attached, form a 4- to 6-membered ring, wherein said 4- to 6-membered ring optionally may contain one to three substituents independently selected from the group consisting of halogen, $C_1$-$C_6$ alkyl, $C_1$-$C_6$ haloalkyl, $C_6$-$C_{10}$ aryl, and —$OR^9$;

$R^9$ at each occurrence is independently H, $C_1$-$C_6$ alkyl, or $C_6$-$C_{10}$ aryl;

$R^{10}$ at each occurrence is independently selected from the group consisting of hydrogen, $C_1$-$C_6$ alkyl, $C_3$-$C_6$ cycloalkyl, $C_6$-$C_{10}$ aryl, and 5- to 10-membered heteroaryl;

$R^a$ and $R^b$ are each independently hydrogen or $C_1$-$C_6$ alkyl; and $R^c$ and $R^d$ are independently hydrogen or $C_1$-$C_4$ alkyl.

In another embodiment, the present invention provides a compound according to any one of formula (V), (VI), (VII), or (VIII):

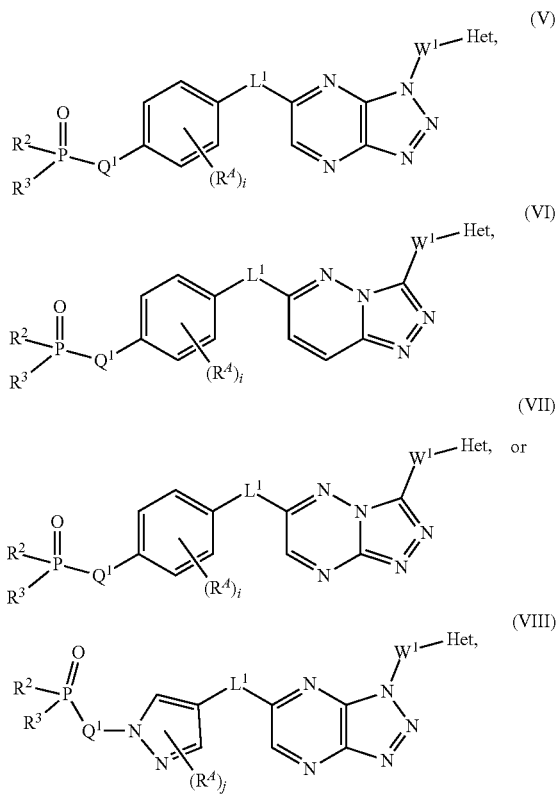

or a pharmaceutically acceptable salt, solvate, or prodrug thereof, wherein:
  i is 1, 2, 3, or 4;
  j is 1 or 2; and
  $R^A$ at each occurrence is independently selected from the group consisting of halogen, $C_1$-$C_6$ alkyl, $C_1$-$C_6$ alkoxy, $C_1$-$C_6$ haloalkyl, $C_1$-$C_6$ haloalkoxy, hydroxy, $C_1$-$C_6$ acyl, cyano, nitro, and $NR^cR^d$;
  $L^1$ is a bond, O, S, $NR^1$, or $C(R^L)_2$, wherein $R^L$ at each occurrence is independently hydrogen, halogen, or $C_1$-$C_4$ alkyl;
  $Q^1$ is a bond or $C(R^Q)_2$, wherein $R^Q$ at each occurrence is independently hydrogen, halogen, or $C_1$-$C_4$ alkyl;
  $R^1$ at each occurrence is independently H or $C_1$-$C_4$ alkyl;
  $R^2$ and $R^3$ are each independently selected from the group consisting of $C_1$-$C_6$ alkyl, $C_3$-$C_6$ cycloalkyl, —$NR^7R^8$, $OR^4$, and —$OCH_2(C=O)OR^9$, wherein the alkyl is optionally substituted by one to three substituents independently selected from the group consisting of $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —$C(O)OR^9$, —$C(O)R^{10}$, —$NR^aR^b$, and —$C(O)NR^cR^d$
  $R^4$ at each occurrence is independently H, $C_1$-$C_4$ alkyl, or phenyl;
  $W^1$ is a bond or $CR^5R^6$, wherein $R^5$ and $R^6$ are each independently H, halogen, or $C_1$-$C_4$ alkyl, or $R^5$ and $R^6$ together with the carbon atom to which they are attached form a 3- to 6-membered ring optionally substituted;
  $R^7$ and $R^8$ are independently selected from hydrogen, $C_1$-$C_6$ alkyl, $C_3$-$C_6$ cycloalkyl, $C_6$-$C_{10}$ aryl, 5- to 10-membered heteroaryl, and 5- to 10-membered heterocyclyl; or alternatively, $R^7$ and $R^8$ together with the nitrogen atom to which they are attached, form a 4- to 6-membered ring, wherein said 4- to 6-membered ring optionally may contain one to three substituents independently selected from the group consisting of halogen, $C_1$-$C_6$ alkyl, $C_1$-$C_6$ haloalkyl, $C_6$-$C_{10}$ aryl, and —$OR^9$;
  "Het" is heteroaryl or heterocyclyl, each optionally substituted with one to four substituents independently selected from the group consisting of halogen, $C_1$-$C_6$ alkyl, $C_1$-$C_6$ haloalkyl, $C_2$-$C_6$ alkenyl, $C_3$-$C_6$ cycloalkyl, $C_6$-$C_{10}$ aryl, 5- to 10-membered heteroaryl, 3- to 10-membered heterocyclyl, and CN;
  $R^9$ at each occurrence is independently H or $C_{1-6}$ alkyl;
  $R^{10}$ at each occurrence is independently H or $C_{1-6}$ alkyl;
  $R^{13}$ at each occurrence is independently hydrogen, $C_1$-$C_6$ alkyl, or $C_1$-$C_6$ haloalkyl;
  $R^{14}$ at each occurrence is independently hydrogen or $C_1$-$C_6$ alkyl;
  $R^a$ and $R^b$ are independently selected from hydrogen, $C_1$-$C_6$ alkyl, $C_3$-$C_6$ cycloalkyl, $C_6$-$C_{10}$ aryl, 5- to 10-membered heteroaryl, and benzyl; and
  $R^c$ and $R^d$ are independently hydrogen or $C_1$-$C_6$ alkyl.

In another embodiment, the present invention provides a compound according to any one of formula (V), (VI), (VII), or (VIII), or a pharmaceutically acceptable salt or solvate thereof, wherein $L^1$ is absent or $NR^1$, and $Q^1$ is absent or $C(R^Q)_2$.

In another embodiment, the present invention provides a compound according to any one of formula (V), (VI), (VII), or (VIII), or a pharmaceutically acceptable salt or solvate thereof, wherein $L^1$ is absent, and $Q^1$ is $C(R^Q)_2$ In another embodiment, the present invention provides a compound according to any one of formula (V), (VI), (VII), or (VIII), or a pharmaceutically acceptable salt or solvate thereof, wherein $L^1$ is $NR^1$, and $Q^1$ is $C(R^Q)_2$.

In another embodiment, the present invention provides a compound according to any one of formula (V), (VI), (VII), or (VIII), or a pharmaceutically acceptable salt or solvate thereof, wherein $L^1$ is $NR^1$, and $Q^1$ is absent.

In another embodiment, the present invention provides a compound according to any one of formula (V), (VI), (VII), or (VIII), or a pharmaceutically acceptable salt or solvate thereof, wherein $L^1$ and $Q^1$ are both absent.

In another embodiment, the present invention provides a compound according to any one of formula (V), (VI), (VII), or (VIII), or a pharmaceutically acceptable salt, solvate, or prodrug thereof, wherein the Het is selected from the group consisting of:

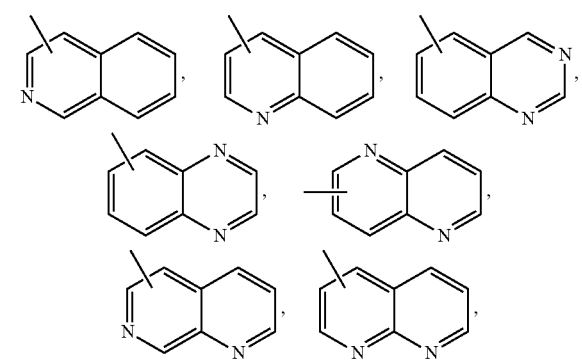

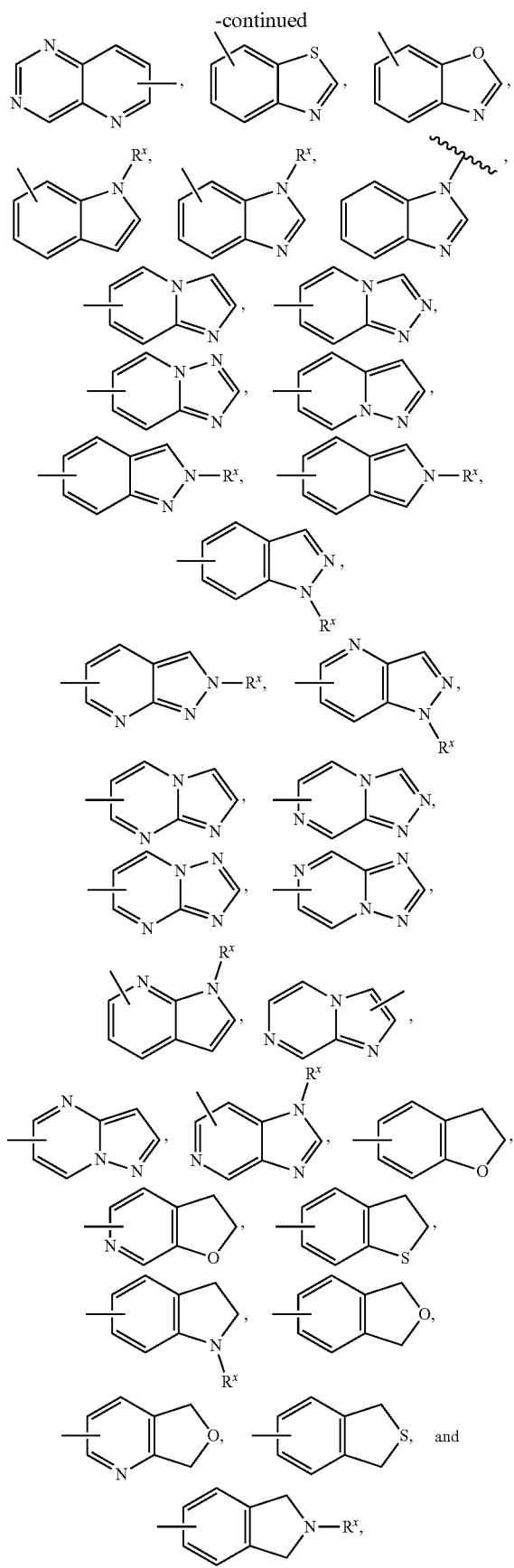

each optionally substituted by one, two, or three substituents independently selected from the group consisting of halogen, $C_1$-$C_6$ alkyl, $C_1$-$C_6$ alkoxy, $C_1$-$C_6$ haloalkyl, and $C_1$-$C_6$ haloalkoxy.

In another embodiment, the present invention provides a compound according to any one of formula (V), (VI), (VII), or (VIII), or a pharmaceutically acceptable salt, solvate, or prodrug thereof, wherein $R^2$ and $R^3$ are independently selected from the group consisting of $C_1$-$C_6$ alkyl, $C_3$-$C_6$ cycloalkyl, —$OR^4$, —$NR^7R^8$, and —$OCH_2(C=O)OR^9$, wherein the alkyl or cycloalkyl is optionally substituted by one to four substituents independently selected from the group consisting of $C_1$-$C_4$ alkyl, $C_6$-$C_{10}$ aryl, 5- to 10-membered heteroaryl, and $C_3$-$C_6$ cycloalkyl; wherein $R^4$ is hydrogen or $C_1$-$C_6$ alkyl, $R^7$ and $R^8$ are independently hydrogen or $C_1$-$C_4$ alkyl, and $R^9$ is $C_1$-$C_4$ alkyl.

In another embodiment, the present invention provides a compound of formula (I), or a pharmaceutically acceptable salt, solvate or prodrug thereof, selected from the group consisting of (Compound List 1):

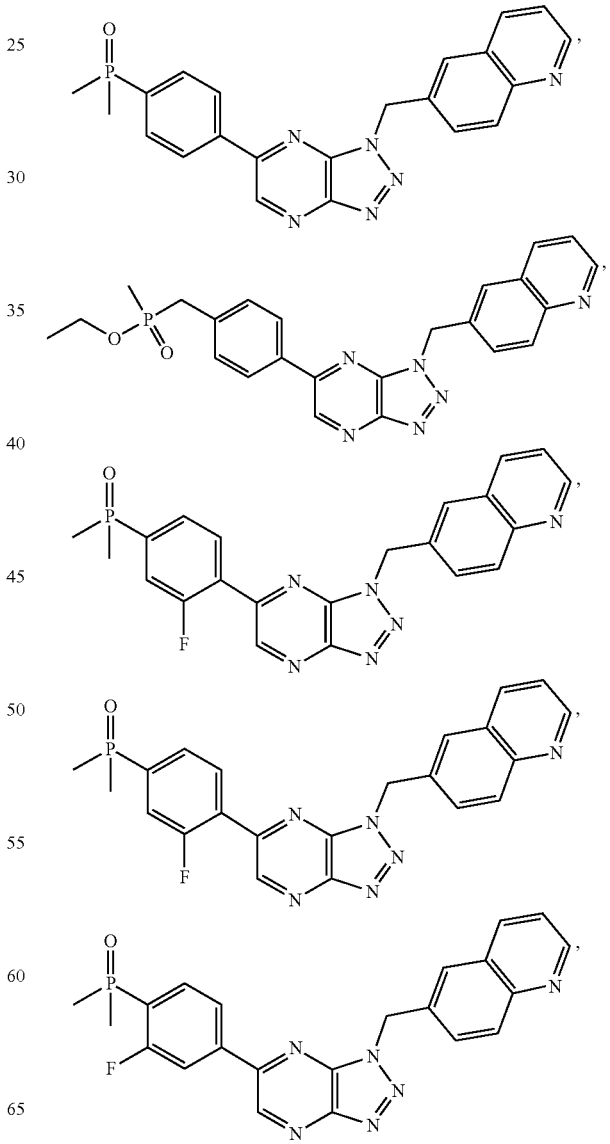

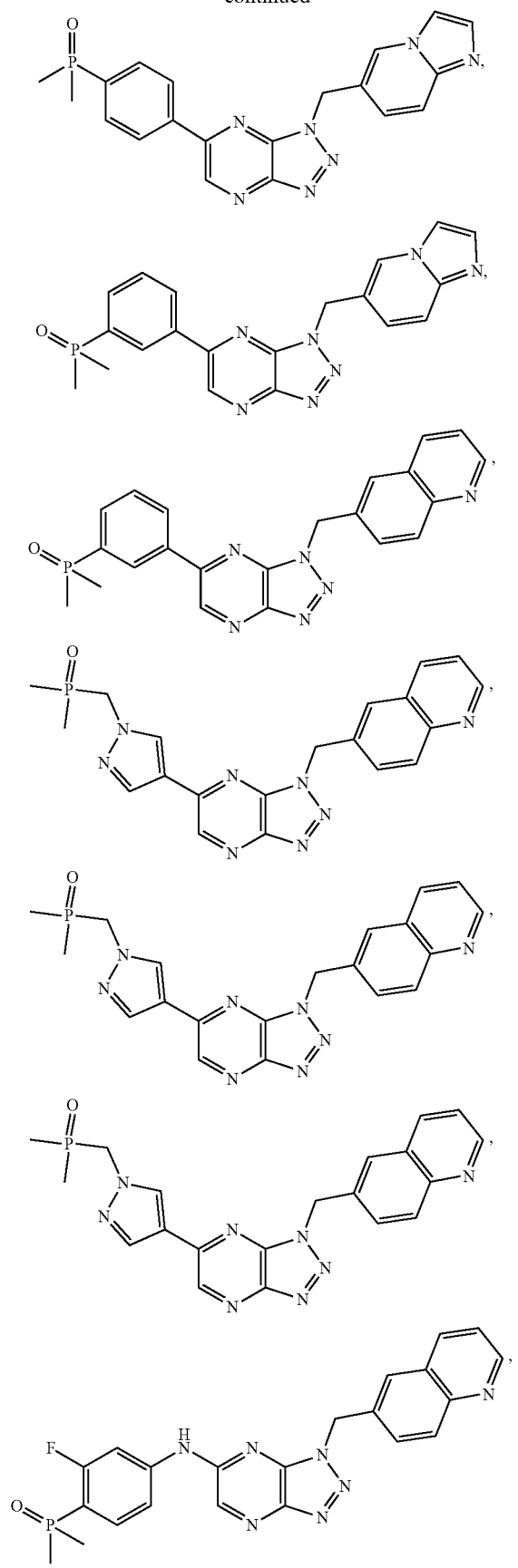
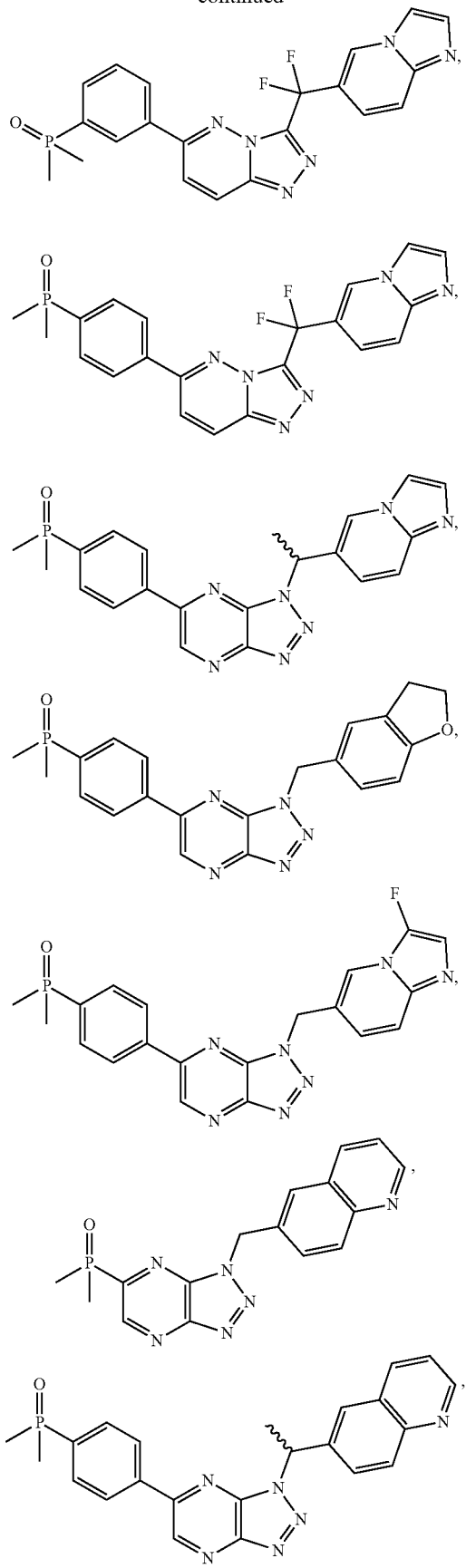

17
-continued
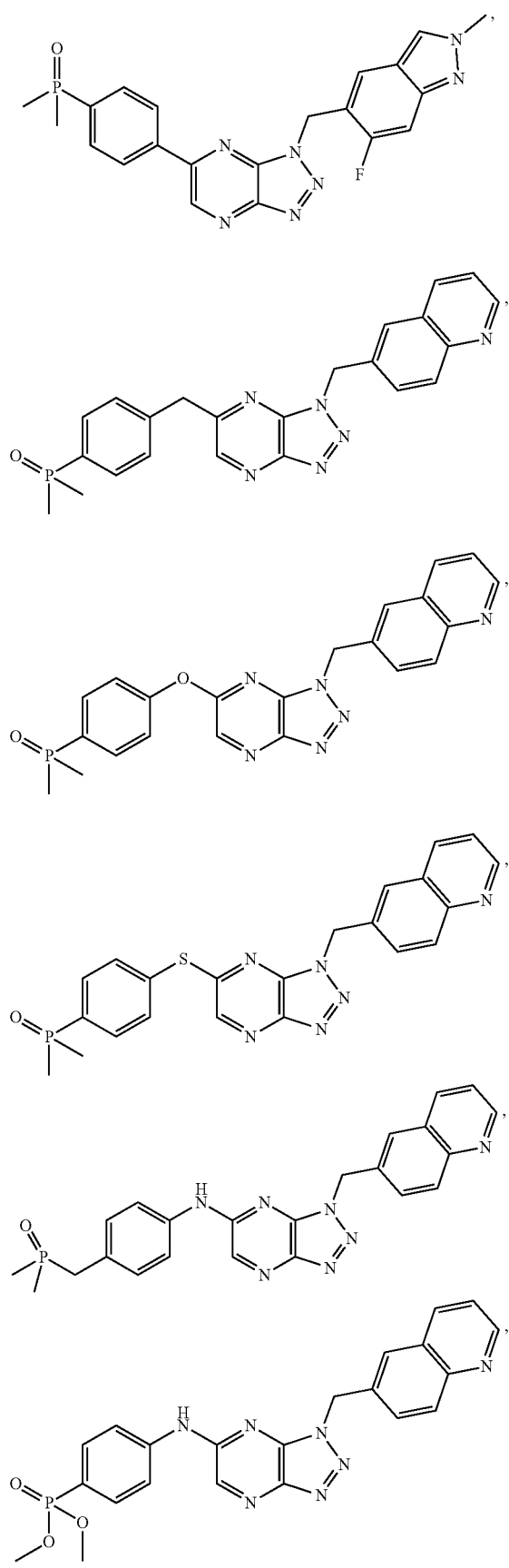
18
-continued
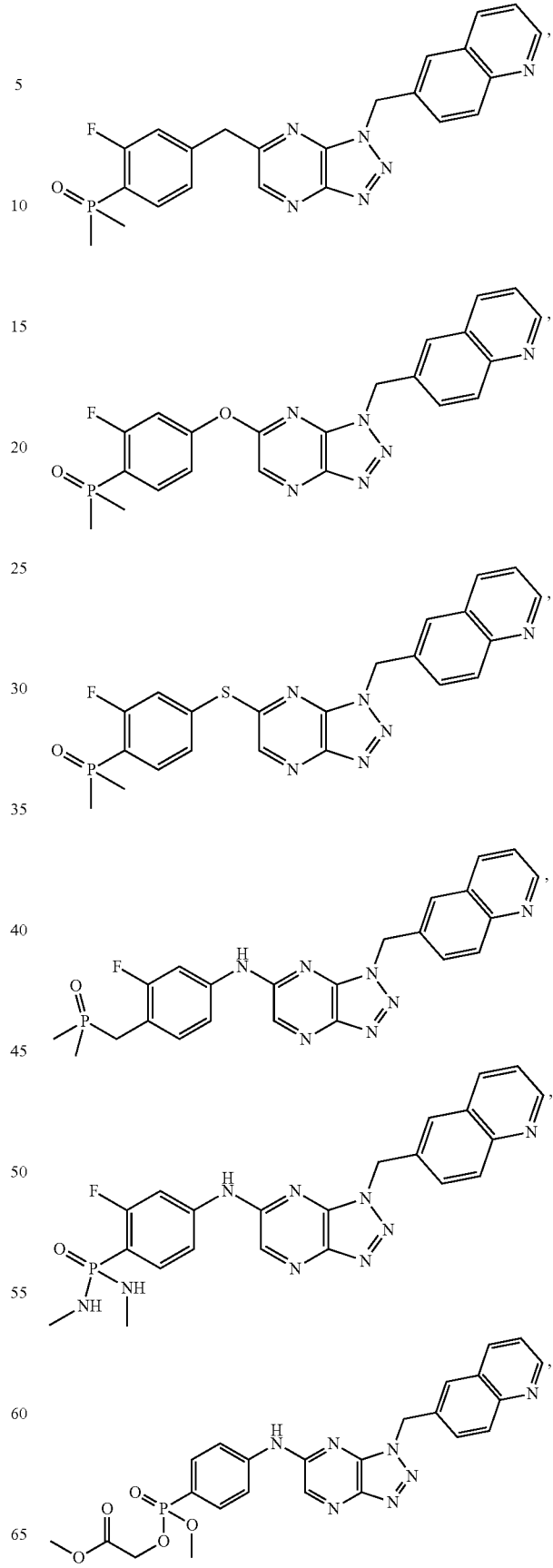

19
-continued
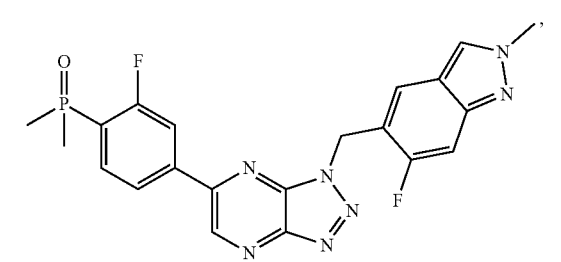
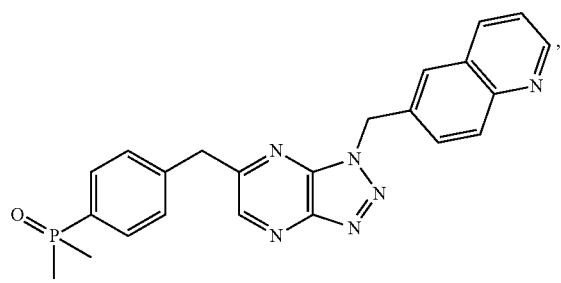
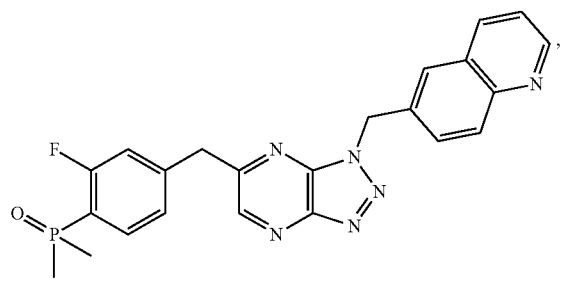
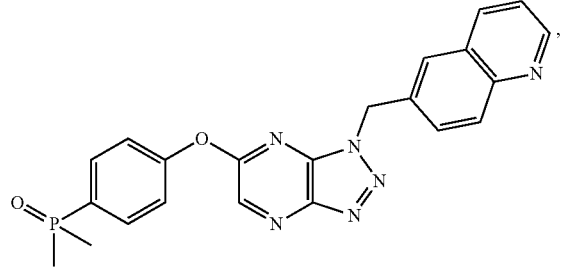
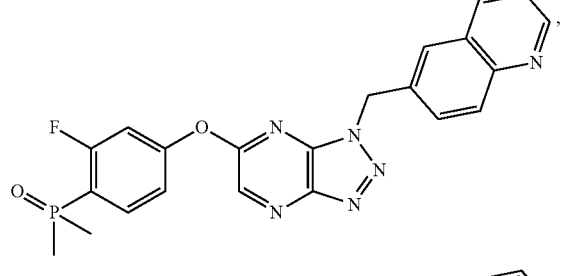
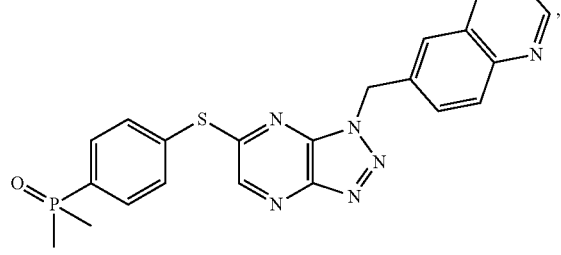
20
-continued
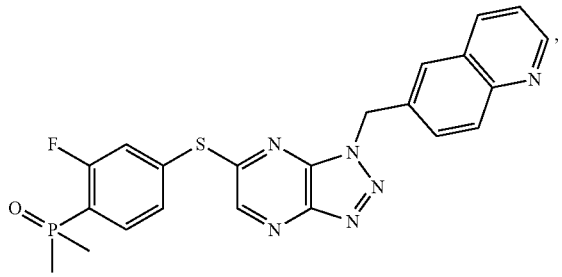
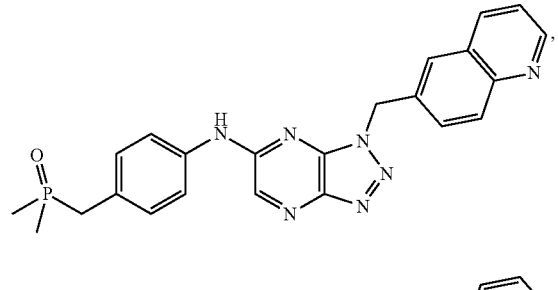
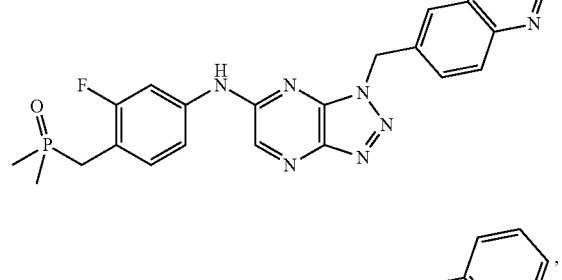
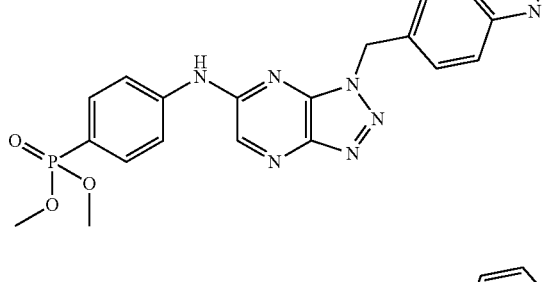
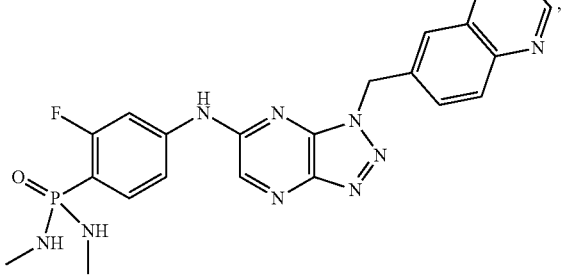
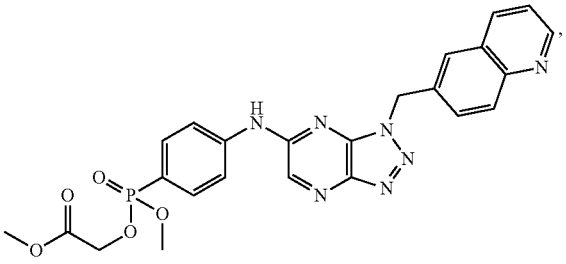

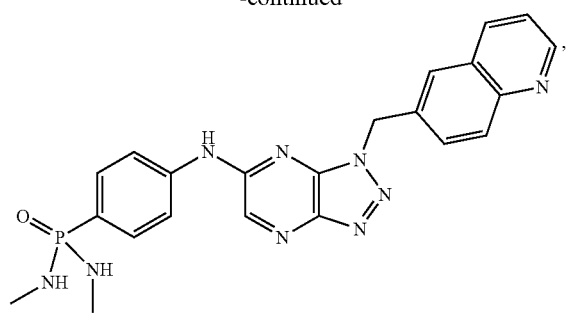
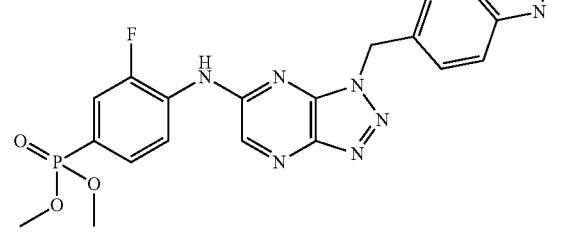
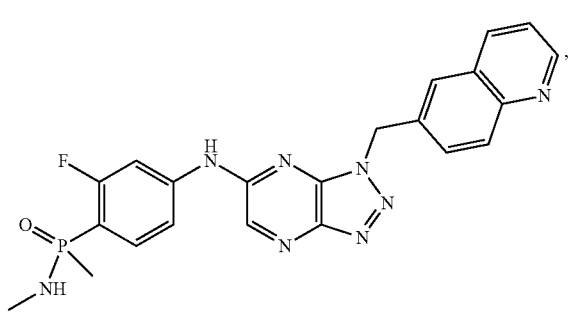
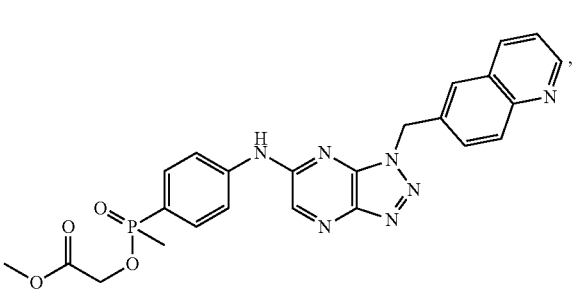
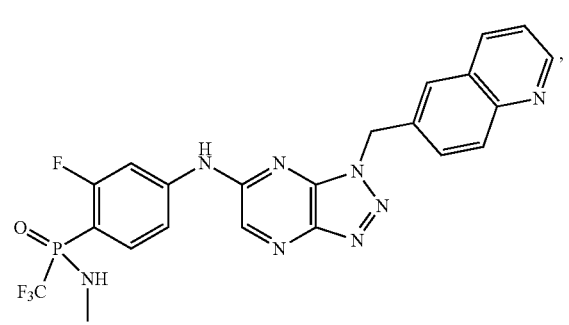
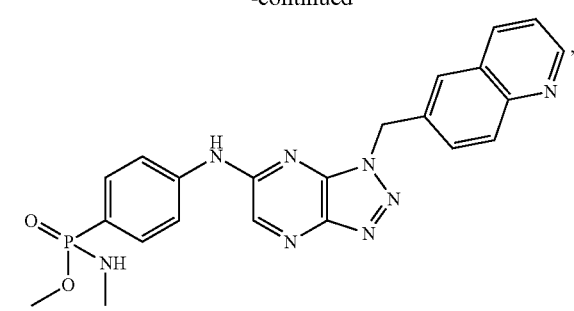
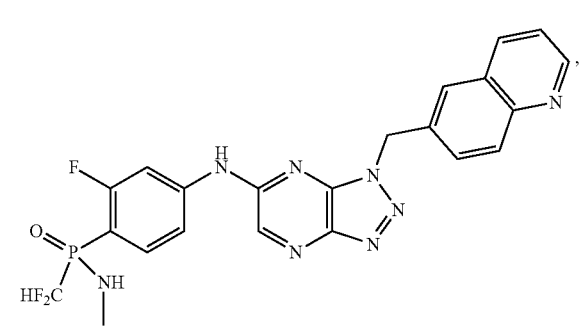
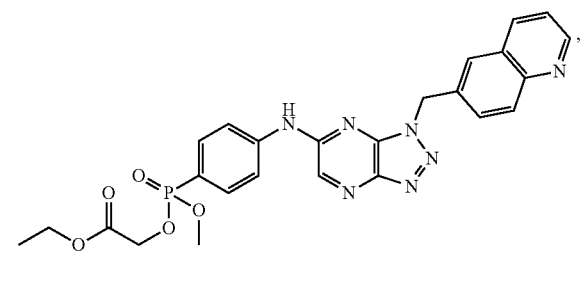
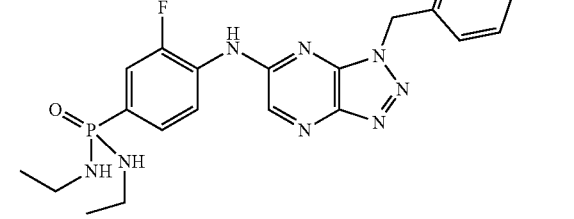
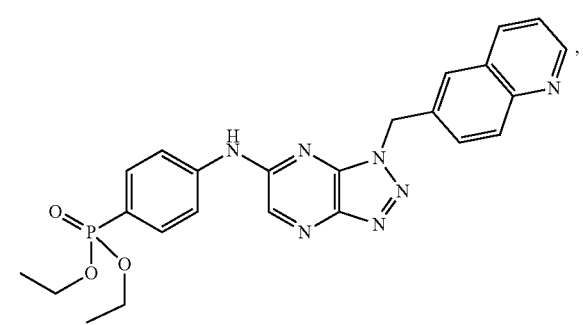

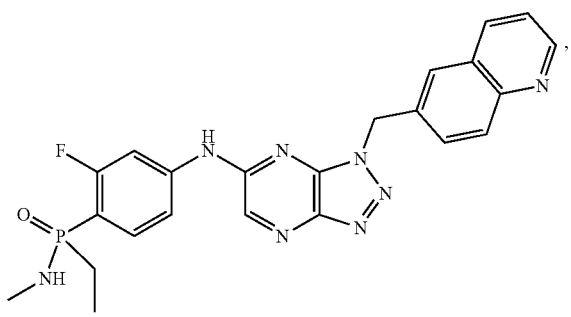
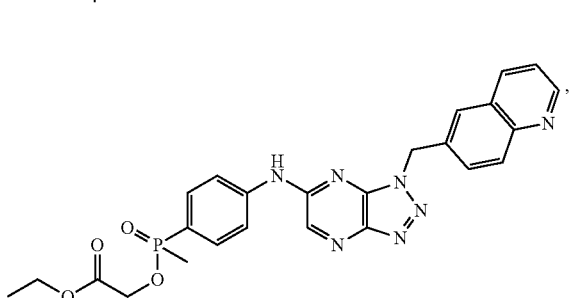
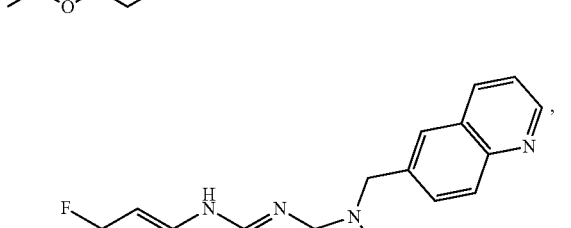
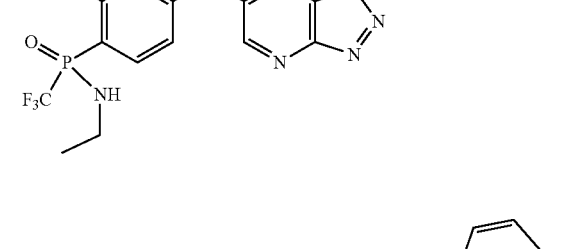
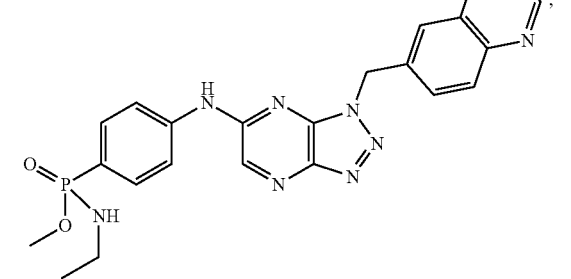
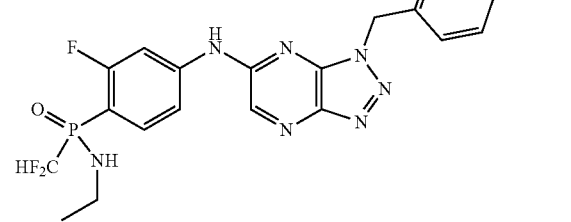
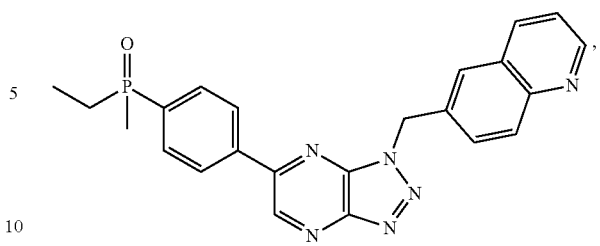
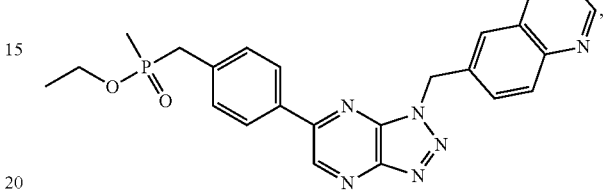
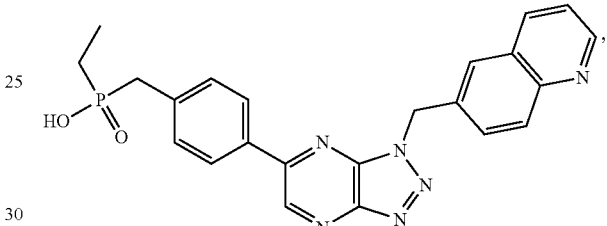
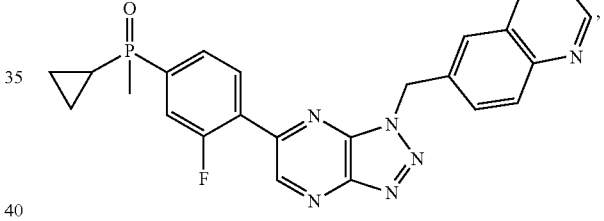
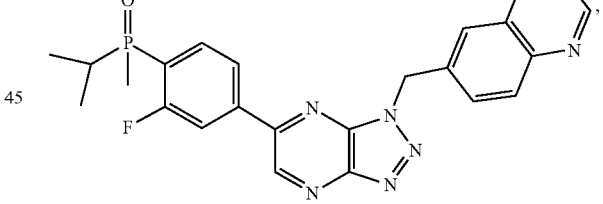
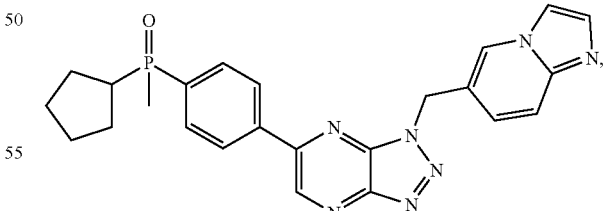
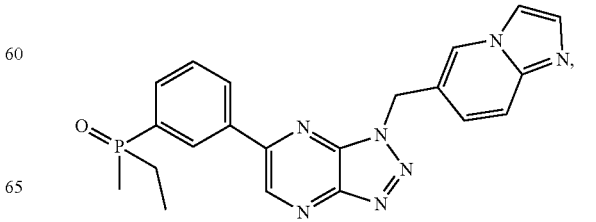

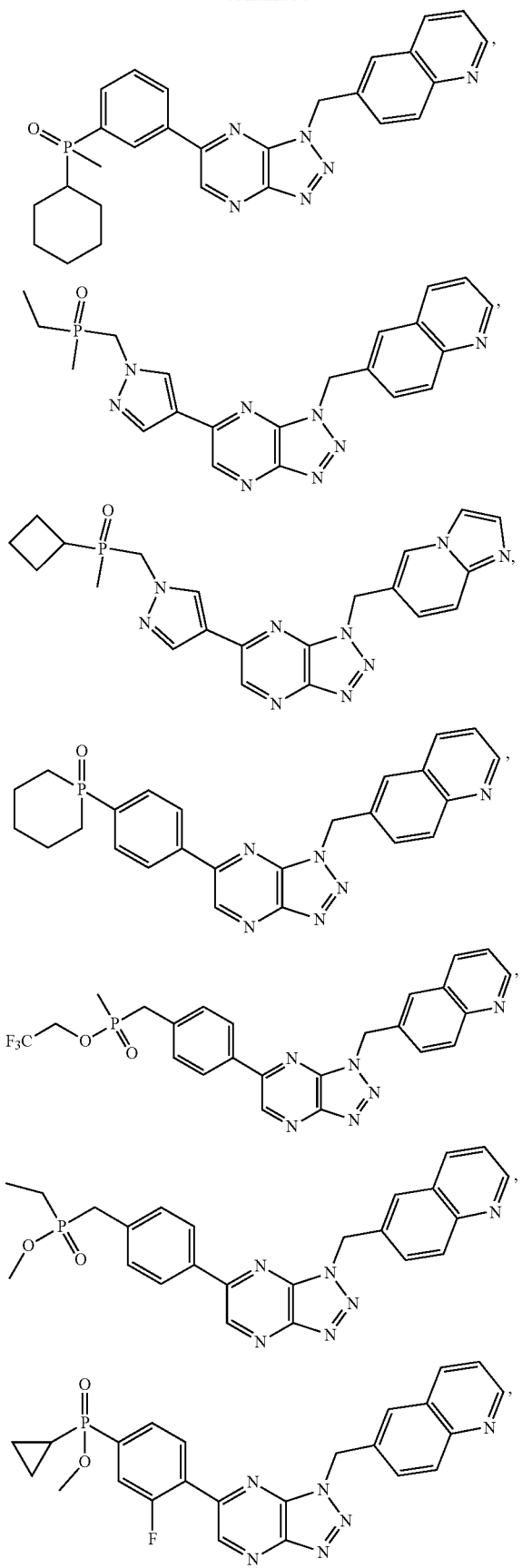
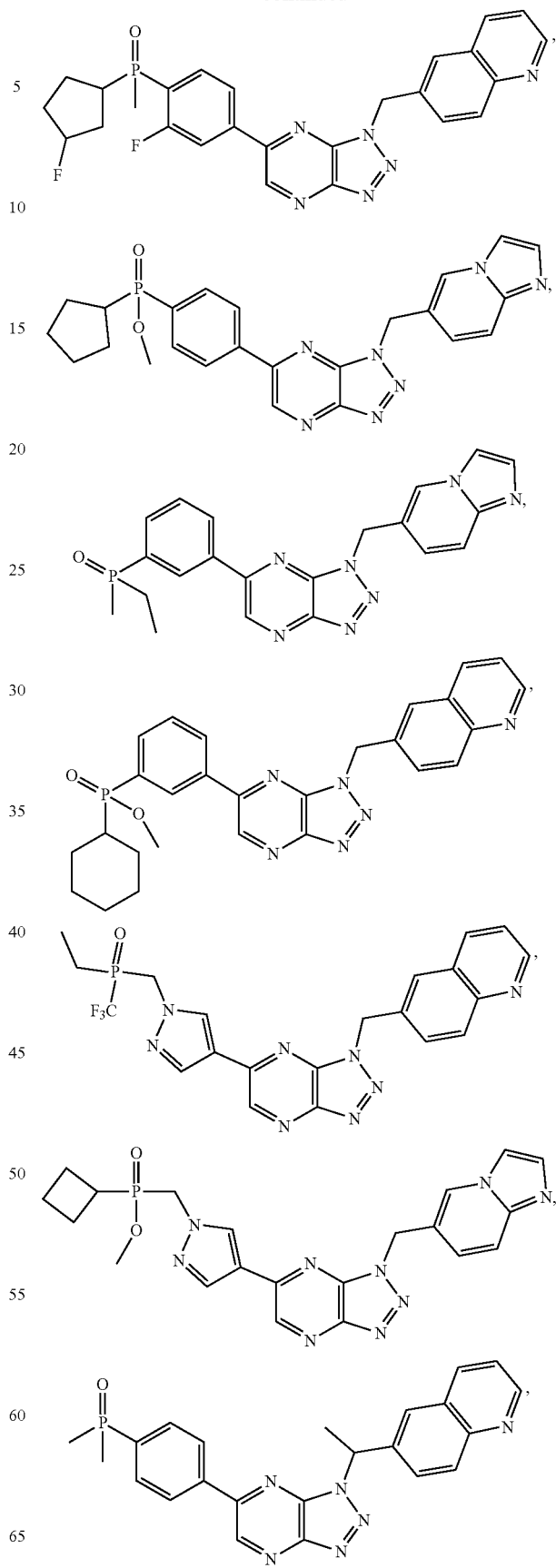

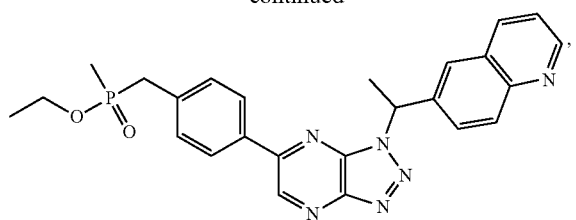
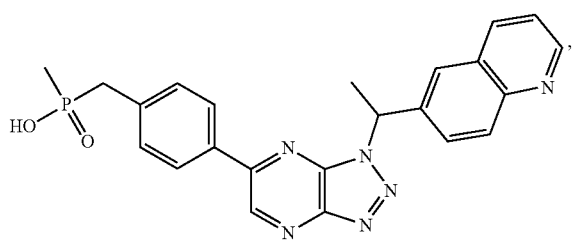
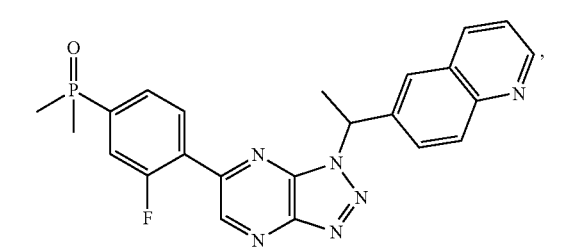
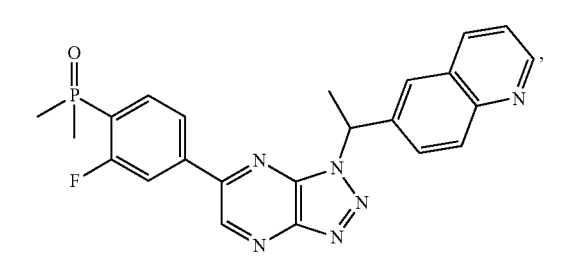
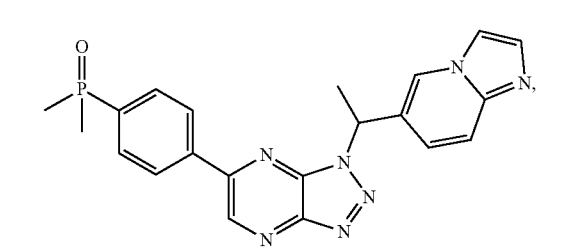
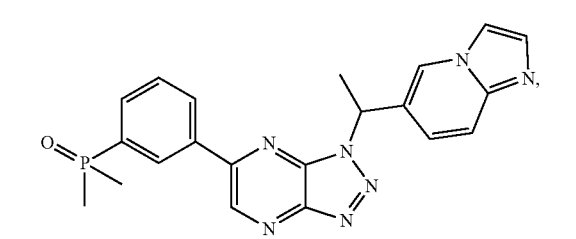
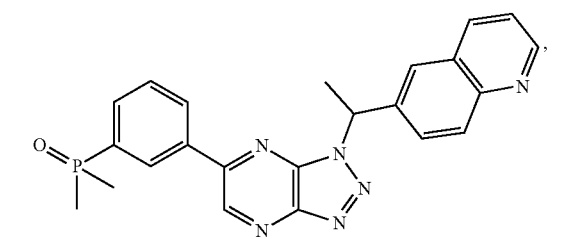
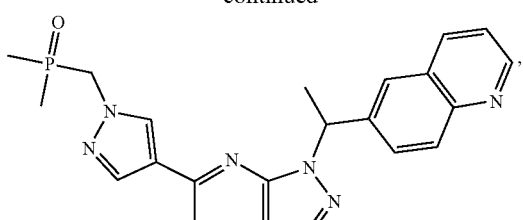
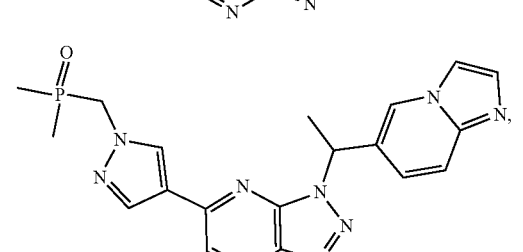
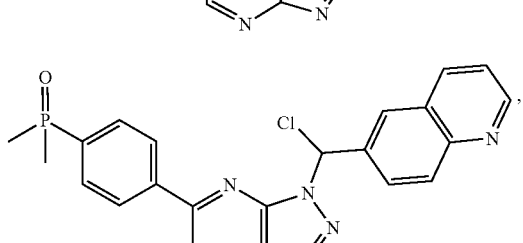
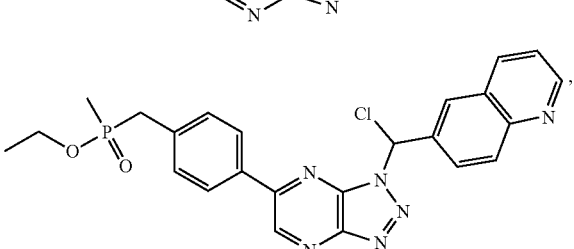
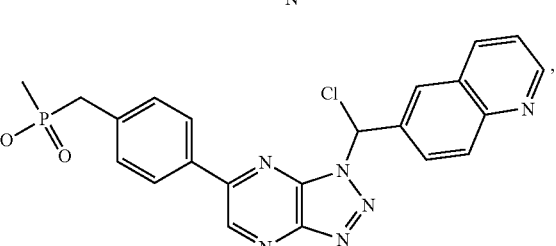
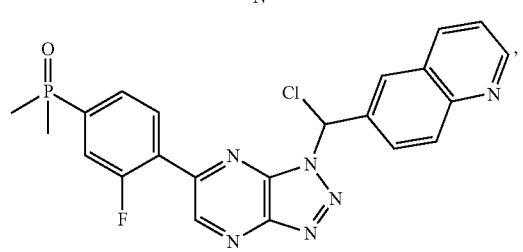
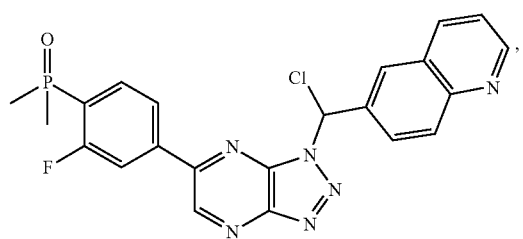

-continued

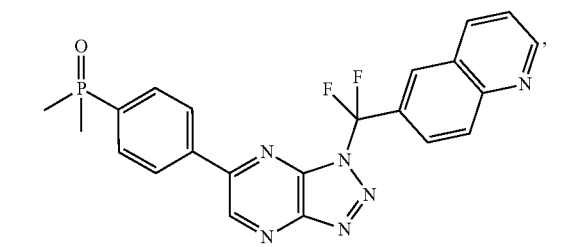
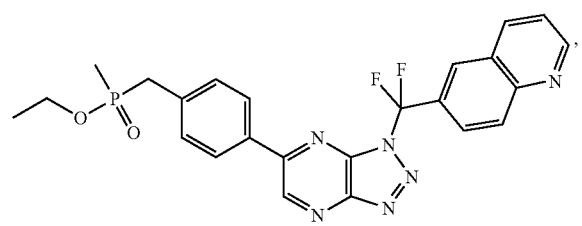
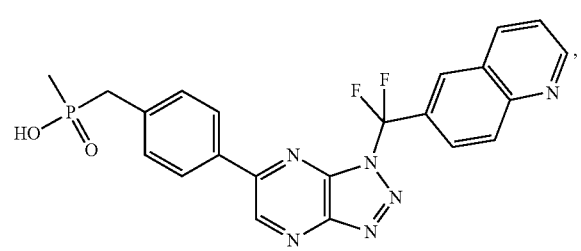
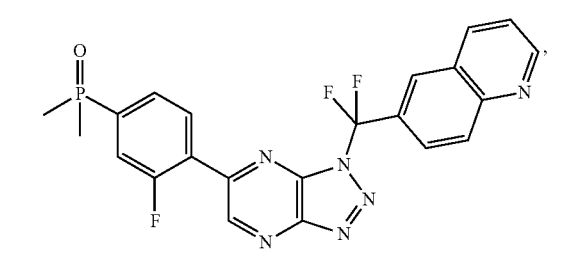
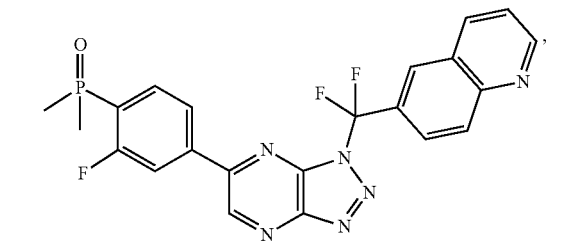
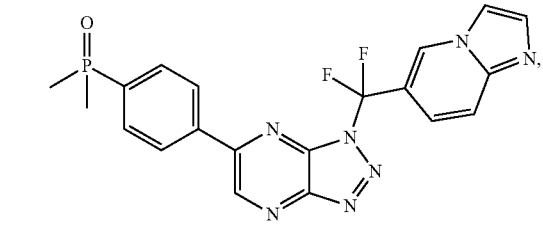
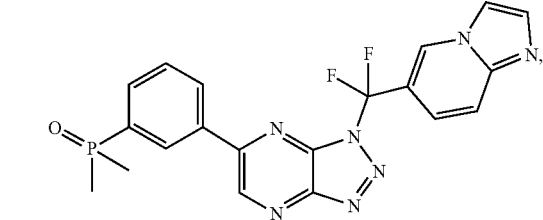
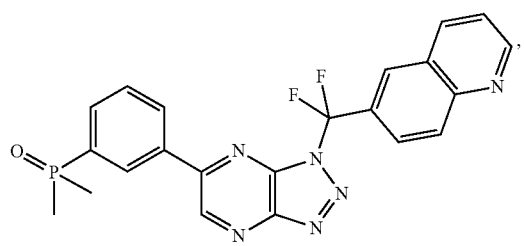
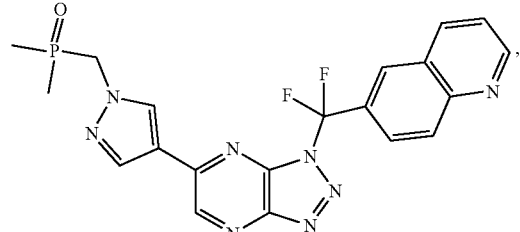
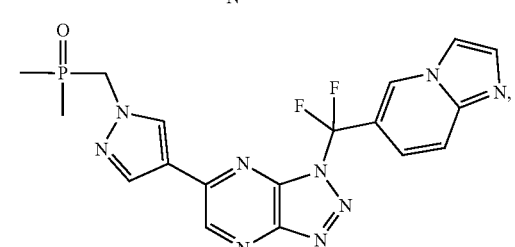
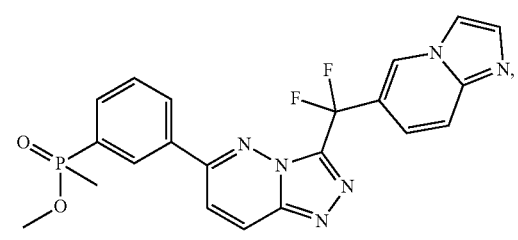
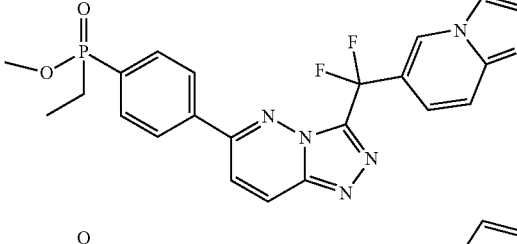
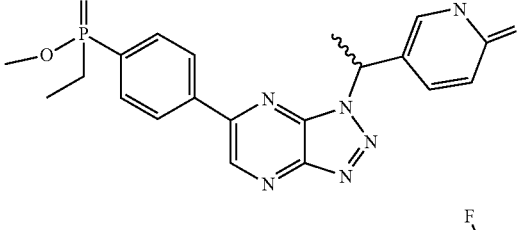
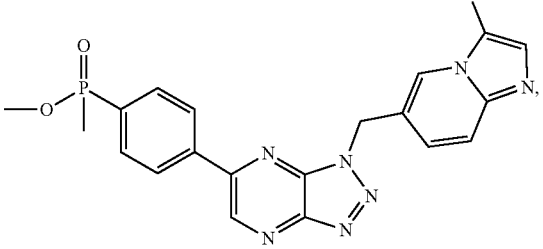

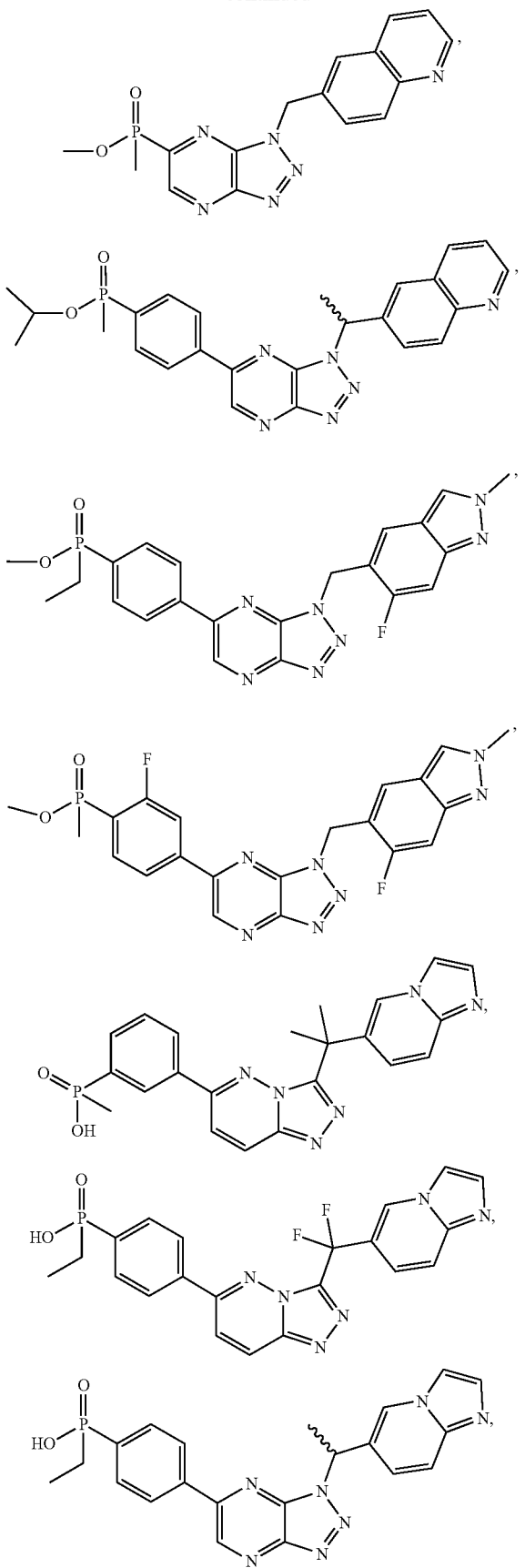
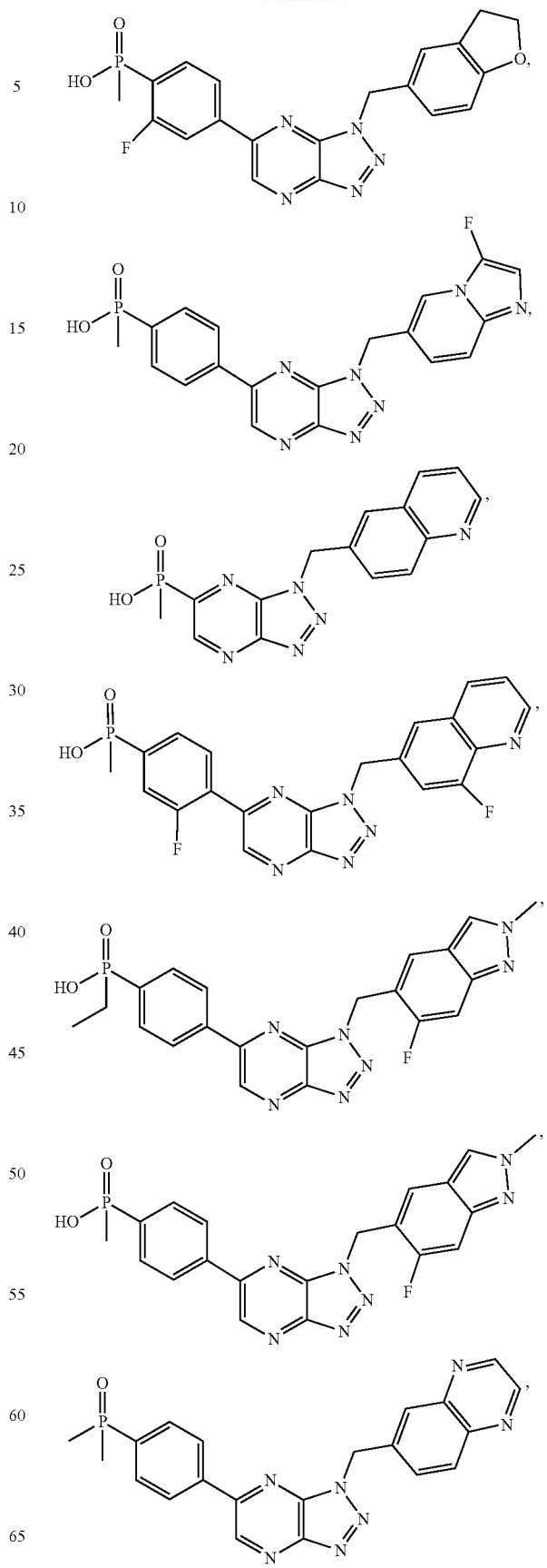

-continued
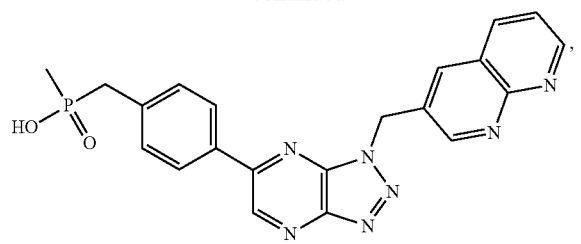
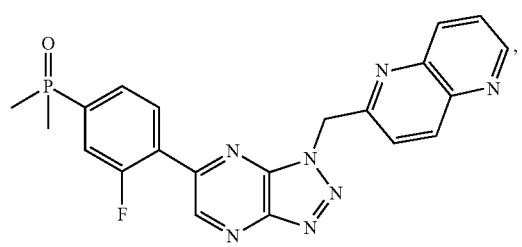
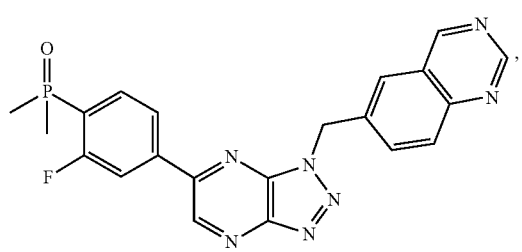
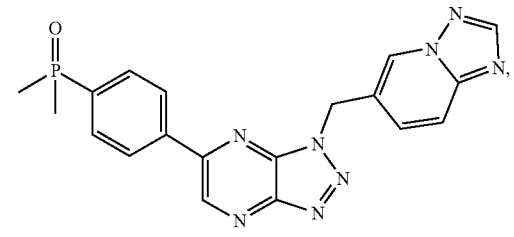
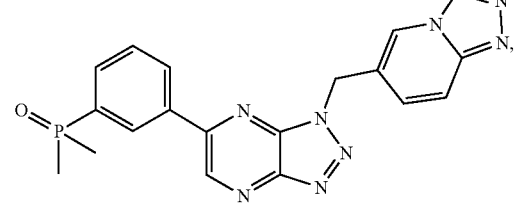
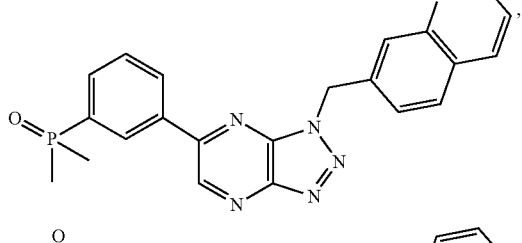
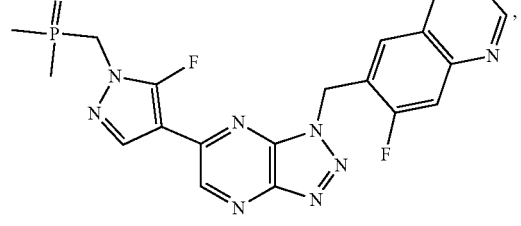
-continued
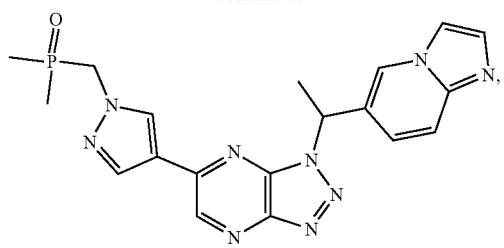
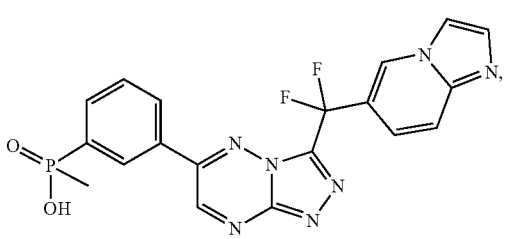
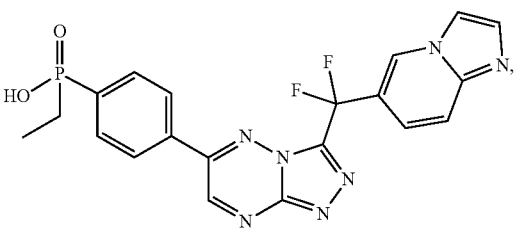
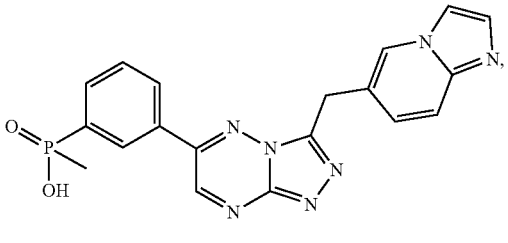
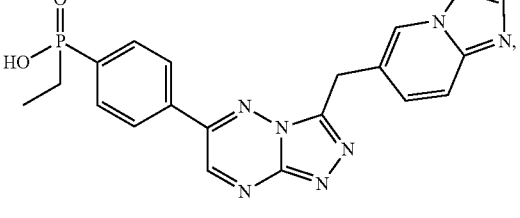
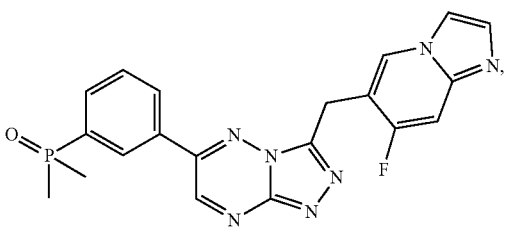
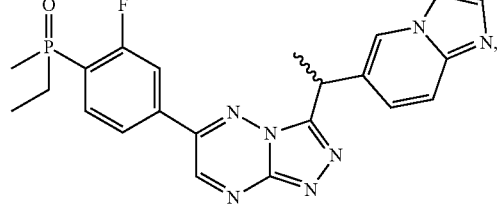

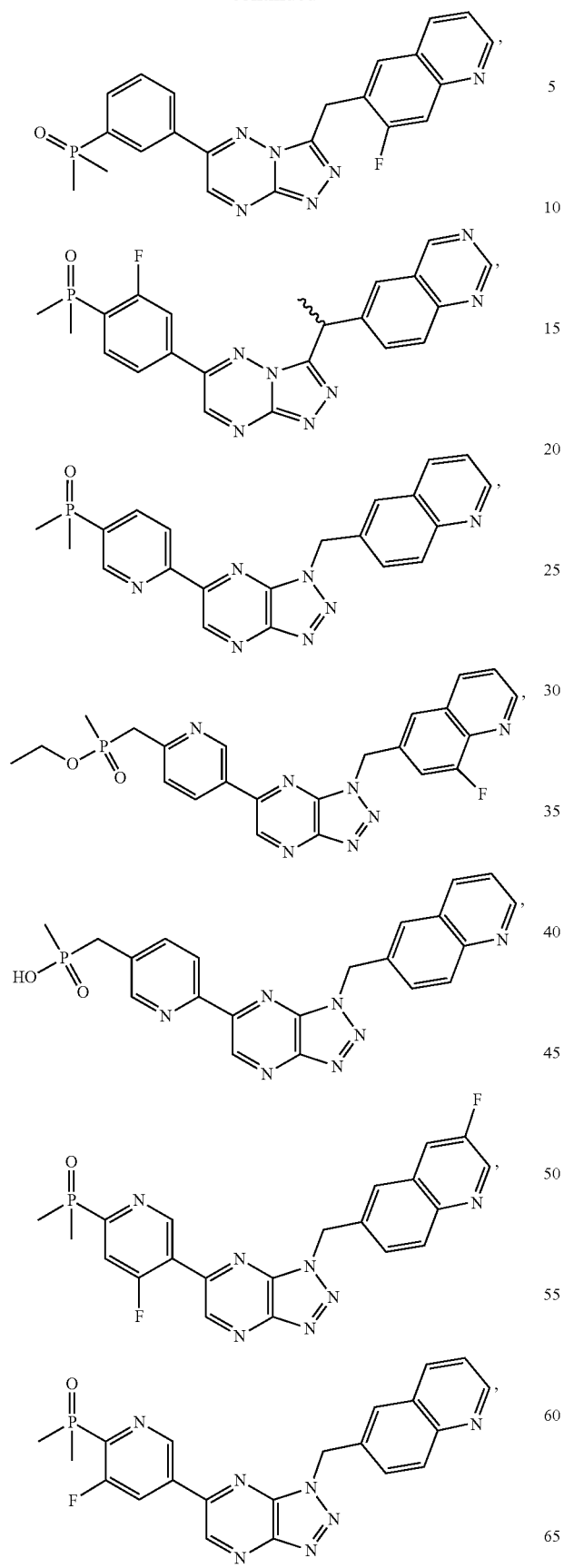
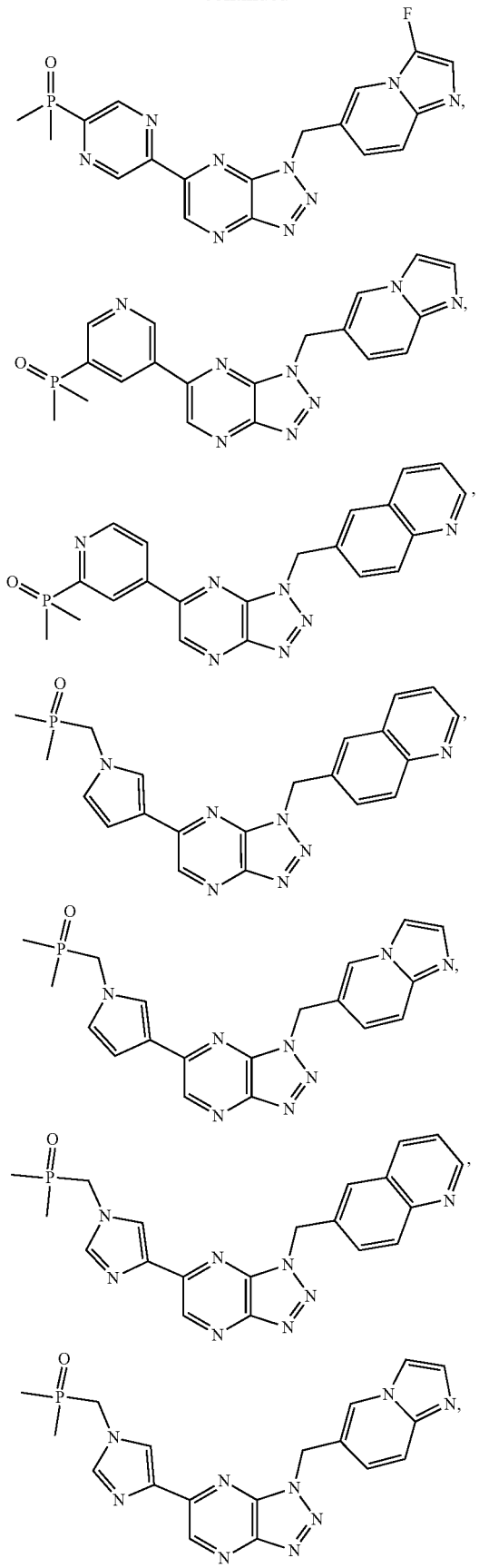

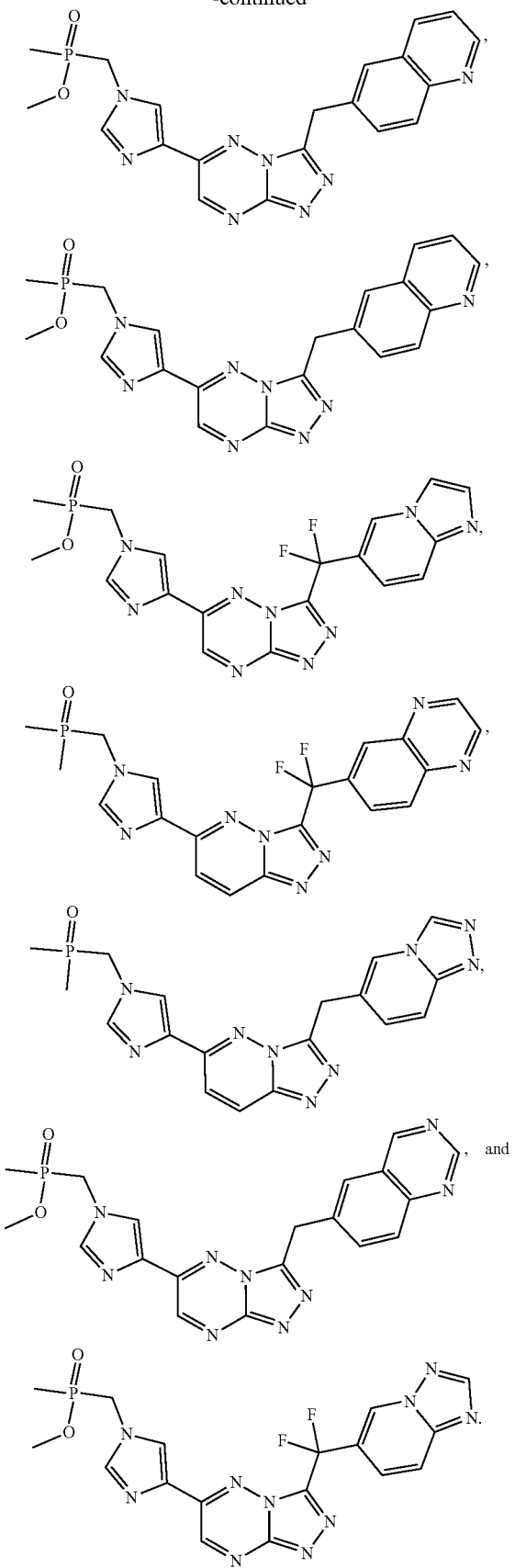

In another aspect, the present invention provides a pharmaceutical composition comprising a compound of formula (I), (II), (III), (IV), (V), (VI), (VII), or (VIII) according to any embodiment described herein, or a pharmaceutically acceptable salt, solvate or prodrug thereof, and a pharmaceutically acceptable carrier.

In another aspect, the present invention provides a method of treating a disease or disorder in a subject, comprising administering to the subject a therapeutically effective amount of a compound of formula (I), (II), (III), (IV), (V), (VI), (VII), or (VIII) according to any embodiment described herein, or a pharmaceutically acceptable salt, solvate or prodrug thereof.

In another aspect, the present invention provides a method of treating a disease or disorder in a subject, comprising administering to the subject a therapeutically effective amount of a compound comprising administering to the subject a pharmaceutical composition comprising a compound of formula (I), (II), (III), (IV), (V), (VI), (VII), or (VIII) according to any embodiment described herein and a pharmaceutically acceptable carrier.

In a preferred embodiment, the disease or disorder is associated with tyrosine kinase c-MET activity.

In some embodiments, sometimes preferred, the disease or disorder is selected from the group consisting of gastric cancer, lung cancer (e.g., non-small cell lung cancer), colon cancer, breast cancer, pancreatic cancer, esophageal cancer, colorectal cancers, ovarian cancers, brain cancer (e.g., glioblastomas), hepatocellular cancer, melanoma, atherosclerosis, and fibrosis of the lung.

In another aspect, the present invention provides use of a compound of any of formulas (I) through (VIII) according to any embodiment described herein, or a pharmaceutically acceptable salt, solvate or prodrug thereof, in the manufacture of a medicament for treatment of a disease or disorder associated with a tyrosine kinase c-MET activity, which disease or disorder sometimes preferably is selected from the group consisting of gastric cancer, lung cancer (e.g., non-small cell lung cancer), colon cancer, breast cancer, pancreatic cancer, esophageal cancer, colorectal cancers, ovarian cancers, glioblastomas, hepatocellular cancer, melanoma, and other solid tumors, such as sarcoma, fibrosarcoma, osteoma, neuroblastoma, teratocarcinoma, retinoblastoma, rhabdomyosarcoma, hematopoietic malignancy, malignant ascites, and the like.

In some embodiments, the compounds of formula (I), (II), (III), (IV), (V), (VI), (VII), or (VIII) according to any embodiment described herein, and pharmaceutically acceptable salts, solvates or prodrugs thereof, or a pharmaceutical composition thereof, can also be used for treating, delaying or preventing the progression or onset of diseases or disorders such as cardiovascular diseases, immunological disorders, autoimmune disorders, ocular disorders, cancers, or cancer metastasis, for example, non-small cell lung cancer in advanced stage and its metastasis.

In some embodiments, sometimes preferred, the compounds of formula (I), (II), (III), (IV), (V), (VI), (VII), or (VIII) according to any embodiment described herein, and pharmaceutically acceptable salts, solvates or prodrugs thereof, or a pharmaceutical composition thereof, can be used for treating disorders or disorders in combination with administration of one or more additional active agents, for example, cytotoxic agents, chemotherapeutic agents, peptides, antibodies, antigens, adjuvants, etc., in particular, anticancer agents such as checkpoint inhibitors, CTLA-4, LAG-3 and PD-1 pathway antagonists, Epidermal growth factor receptor (EGFR) inhibitors, vascular endothelial growth factor (VEGF) receptor inhibitors, alkylating agents, anti-tumor antibiotics, retinoids, and immunomodulatory agents, or the like.

In another aspect, the present invention provides use of a compound of any one of formulae (I) through (VIII) according to any embodiment described herein, or a pharmaceutically acceptable salt, solvate or prodrug thereof, or a pharmaceutical composition thereof, for use in the treatment of a disease or disorder associated with tyrosine kinase c-MET activity.

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group, such as benzyl, may be substituted as described in the definition of the term "aryl."

Unless fixed at a specific position, a mono-valent bond floating on any position of a substituent ring structure indicates that the substituent can be connected with the rest of molecular moiety through any available open position in the ring structure, but it is not limited to the specific ring structure where the bond is floating on, as long as it does not violate basic bonding principles and forms a stable compound. For example, an isoquinolinyl group represented by either

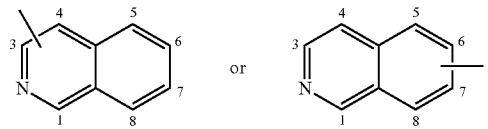

is equivalent, and both represent that any of the positions 1, 3, 4, 5, 6, 7, and 8 may be connected to the rest of the molecular moiety. Similarly, a divalent isoquinolinyl group represented by

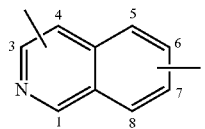

can be connected to the rest of molecular moiety through any combinations of the two positions among 1, 3, 4, 5, 6, 7, and 8.

"Alkoxy" means the group —OR wherein R is alkyl, as defined herein. Representative examples include methoxy, ethoxy, propoxy, isopropoxy, sec-butoxy, tert-butoxy, pentyloxy, hexyloxy, 3-methylhexyloxy, or the like.

"Alkyl" refers to a group derived from a straight or branched chain saturated hydrocarbon by removal of a hydrogen from one of the saturated carbons. The alkyl group preferably contains from one to ten carbon atoms, sometimes preferably one to six carbon atoms ("lower alkyl"), and sometimes even more preferably one to four carbon atoms. Representative examples of alkyl group include, but are not limited to, methyl, ethyl, n-propyl, isopropyl, n-butyl, sec-butyl, tert-butyl, pentyl, hexyl, 3-methylheptyl, or the like.

"Amino" means a —NH$_2$ group.

"Aryl" means a monocyclic, bicyclic, or polycyclic aromatic radical having 6 to 14 ring carbon atoms formed from removal of a hydrogen atom from a corresponding aromatic carbocyclic compound. The monocyclic aryl radical is aromatic and whereas the polycyclic aryl radical may be partially saturated, so long as the valency (radical) is located on an aromatic ring. Representative examples include phenyl, naphthyl, indanyl, and the like. An aryl group can be substituted or unsubstituted. When substituted, unless specifically defined, the substituent group(s) is preferably one or more, e.g., one to five, sometimes preferably one to three, groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxyl, cycloalkylthio, heterocylic alkylthio and —NR$^9$R$^{10}$.

The term "cyano," as used herein, refers to —CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl.

The terms "halo" and "halogen," as used herein, refer to F, Cl, Br, or I.

The term "haloalkoxy," as used herein, refers to —OR, wherein R is a haloalkyl group containing one to ten carbons, sometimes preferably one to six carbons, and sometimes more preferably one to four carbons.

The term "haloalkyl," as used herein, refers to a $C_1$-$C_{10}$, sometimes preferably $C_1$-$C_6$, and sometimes more preferably $C_1$-$C_4$, alkyl group substituted by at least one halogen atom. The haloalkyl group can be an alkyl group of which all hydrogen atoms are substituted by halogens. Representative examples of haloalkyl include, but are not limited to, trifluoromethyl, fluoromethyl, difluoromethyl, bromomethyl, 1-chloroethyl, perchloroethyl, and 2,2,2-trifluoroethyl, or the like.

The term "heteroaryl," as used herein, refers to 5- to 14-membered monocyclic, bicyclic, or tricyclic, sometimes preferably 5- to 10-membered monocyclic or bicyclic, aromatic radical comprising one or more, preferably one to four, sometimes preferably one to three, heteroatoms independently selected from nitrogen (N), oxygen (O), and sulfur (S) in the aromatic ring(s). As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyrrolyl, imidazolyl, thienyl, furanyl, triazinyl, benzisoxazolyl, 1,2,4-triazolyl, 1,3,5-triazolyl, indolyl, 2,3-dihydro-1H-indolyl, isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, phthalimidyl, pyridinyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl, 2,3,3a,7a-tetrahydro-1H-isoindolyl, pyrrolo[3,2-c]pyridinyl, benzopyranyl, thiazolyl, isothiazolyl, thiadiazolyl, benzothiazolyl, benzothienyl. The heteroaryl group can be substituted or unsubstituted. When substituted, unless specifically defined, the substituent group(s) is preferably one or more groups independently selected from the group consisting of $C_1$-$C_6$ alkyl, $C_1$-$C_6$ alkenyl, $C_1$-$C_6$ alkynyl, $C_1$-$C_6$ alkoxy, $C_1$-$C_6$ alkylsulfo, $C_1$-$C_6$ alkylamino, halogen, thiol, hydroxyl, nitro, cyano, $C_3$-$C_6$ cycloalkyl, $C_1$-$C_6$ heterocyclyl, aryl, heteroaryl, $C_1$-$C_6$ cycloalkoxy, $C_3$-$C_6$ cycloalkylthio, and —$NR^9R^{10}$, wherein $R^9$ and $R^{10}$ are independently hydrogen, $C_1$-$C_6$ alkyl, or C(O)—$R^{11}$, wherein $R^{11}$ is hydrogen or $C_1$-$C_6$ alkyl optionally substituted by one or more halogen.

The term "heterocyclyl," as used herein, refers to a 3- to 14-membered monocyclic, bicyclic, or polycyclic, sometimes preferably 5- to 10-membered monocyclic or bicyclic, nonaromatic group comprising one or more, preferably one to three, heteroatoms independently selected from nitrogen (N), oxygen, and sulfur (S, S(O) or S(O)$_2$) in the nonaromatic ring(s). The heterocyclyl groups of the present disclosure can be attached to the parent molecular moiety through a carbon atom or a nitrogen atom in the group. A heterocyclyl group can be saturated or unsaturated, for example, containing one or more double bond(s) in the ring. Unless otherwise stated, the valency of the group may be located on any atom of any ring within the radical, valency rules permitting. In particular, when the point of valency is located on a nitrogen atom, Ry is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4 piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, or the like. The ring of a heterocyclyl can be fused to the ring of an aryl, heteroaryl or cycloalkyl.

The terms "hydroxy" or "hydroxyl," as used herein, refers to —OH.

The term "nitro," as used herein, refers to —$NO_2$.

The term "oxo," as used herein, refers to "=O".

When any group, for example, alkyl, alkenyl, "cycloalkyl," "aryl," "heterocyclyl," or "heteroaryl", is said to be "optionally substituted," unless specifically defined, it means that the group is or is not substituted by from one to five, sometimes preferably one to three, substituents independently selected from halogen, $C_1$-$C_6$ alkyl, $C_1$-$C_6$ alkoxy, $C_1$-$C_6$ haloalkyl, $C_1$-$C_6$ haloalkoxy, hydroxy, oxo, $C_1$-$C_6$ acyl, cyano, nitro, and $NR^aR^b$ ($R^a$ and $R^b$ are each independently H or $C_1$-$C_4$ alkyl), or the like, provided that such substitution would not violate the conventional bonding principles known to a person of skill in the art. When the phrase "optionally substituted" is used before a list of groups, it means that each one of the groups listed may be optionally substituted.

As a person of skill in the art would understand, when an aryl, heteroaryl, cycloalkyl, heterocyclyl, or the like, is between two or more groups, it should be interpreted as a divalent group with a proper name "arylene," "heteroarylene," "cycloalkylene," "heterocyclylene," or the like. Although sometimes no such distinction is made, for example, "aryl" should be interpreted as "arylene", as a person of skill in the art would understand.

The term "optionally substituted" means the substitution may or may not occur and includes instances where said substitution occurs and instances in which it does not. One of ordinary skill in the art would understand that with respect to any molecule described as containing one or more substituents, only sterically practical and/or synthetically feasible compounds are meant to be included. Unless otherwise specified in this specification, when a variable is said to optionally substituted or substituted with a substituent(s), this is to be understood that this substitution occurs by replacing a hydrogen that is covalently bound to the variable with one these substituent(s).

Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier, excipient, and/or diluent and a compound of this disclosure as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compounds in this disclosure can also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules are preferred) and the bioavailability of the drug substance.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

The compounds of this disclosure, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of this disclosure as the/an active agent, and, in addition, can include other medicinal agents and pharmaceutical agents. Compositions of the compounds in this disclosure can be used in combination with anticancer and/or other agents that are generally administered to a patient being treated for cancer, e.g. surgery, radiation and/or chemotherapeutic agent(s).

If formulated as a fixed dose, such combination products employ the compounds of this disclosure within the dosage range described above and the other pharmaceutically active agent(s) within its approved dosage range. Compounds of this disclosure can alternatively be used sequentially with known pharmaceutically acceptable agent(s) when a combination formulation is inappropriate.

The compounds described herein, as well as their pharmaceutically acceptable salts, or other derivatives thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine and chloride, such as $^2$H (deuterium), $^3$H (tritium), $^{13}$C, $^{14}$C, $^{15}$N, $^{18}$O, $^{17}$, $^{31}$P, $^{32}$P, $^{35}$S, $^{18}$F and $^{36}$Cl, respectively. Isotopically labeled compounds of the present invention, as well as pharmaceutically acceptable salts, esters, prodrugs, solvates, hydrates or other derivatives thereof, generally can be prepared by carrying out the procedures disclosed in the Schemes and/or in the Examples and Preparations below, by substituting a readily available isotopically labeled reagent for a non-isotopically labeled reagent.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements). Moreover, certain isotopically-labeled compounds, for example those into which radioactive isotopes such as $^3$H and $^{14}$C are incorporated, are useful in drug and/or substrate tissue distribution assays such as positron emission tomography (PET). Tritiated, ($^3$H) and carbon-14 ($^{14}$C) isotopes are useful for these embodiments because of their detectability.

The term "pharmaceutically acceptable salt," as used herein, means any non-toxic salt that, upon administration to a recipient, is capable of providing the compounds or the prodrugs of a compound of this invention. The salts can be prepared during the final isolation and purification of the compounds or separately by reacting a suitable nitrogen atom with a suitable acid. Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include, but are not limited to, lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, Nmethylpiperidine, and N-methylmorpholine.

Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19, both of which are incorporated herein by reference.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

"Prodrug" refers to compounds that can be transformed in vivo to yield the active parent compound under physiological conditions, such as through hydrolysis in blood. Common examples include, but are not limited to, ester and amide forms of a compound having an active form bearing a carboxylic acid moiety. Amides and esters of the compounds of the present invention may be prepared according to conventional methods. In particular, in the present invention, a prodrug may also be formed by acylation of an amino group or a nitrogen atom in a heterocyclyl ring structure, which acyl group can be hydrolyzed in vivo. Such acyl group includes, but is not limited to, a $C_1$-$C_6$ acyl, preferably $C_1$-$C_4$ acyl, and more preferably $C_1$-$C_2$ (formyl or acetyl) group, or benzoyl. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The term "therapeutically effective amount," as used herein, refers to the total amount of each active component that is sufficient to show a meaningful patient benefit.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "patient" or "subject" includes both human and other mammals, for example, dogs, cats, horses, monkeys, chimpanzees, or the like.

The term "treating" generally refers to (i) inhibiting the disease, disorder, or condition, i.e., arresting its development; and (ii) relieving the disease, disorder, or condition, i.e., causing regression of the disease, disorder, and/or condition. In addition, the compounds of the present invention may also be used for their prophylactic effects, i.e., preventing a disease, disorder or condition from occurring in a subject that may be predisposed to the disease, disorder, and/or condition but has not yet been diagnosed as having it.

The examples and scheme below depict the general synthetic procedure for the compounds disclosed herein. Synthesis of the compounds disclosed herein, and embodiments thereof, are not limited by these examples and schemes. In the descriptions below, one of ordinary skill in the art would recognize that specific reaction conditions, added reagents, solvents, and reaction temperatures can be modified for the synthesis of specific compounds that fall within the scope of this disclosure. All intermediate compounds described below, for which there is no description of how to synthesize such intermediates within these examples below, are commercially available compounds unless otherwise specified.

Methods

Chemical Synthesis

The compounds described herein, and/or the pharmaceutically acceptable salts thereof, can be synthesized from commercially available starting materials by methods well known to those skilled in the art. The following general synthetic Schemes 1-11 illustrate methods for most of compound preparation. In each of the following schemes, G and G' are leaving groups that are the same or different and are exemplified but not limited to halogen, mesylate, tosylate or triflate. In addition, the reagents, solvents, temperatures, catalysts and ligands are not limited to what is depicted for illustrative purposes. Certain abbreviations and acronyms well known to those trained in the art that are used in the schemes are listed below for clarity.

Abbreviations and Acronyms

The following abbreviations and acronyms may be used in this application:
aq.=aqueous;
$B_2pin_2$=bis(pinacolato)diboron;
n-$Bu_3$P=tri-n-butylphosphine;
CAS #=Chemical Abstracts Service Registry Number;
Compd=compound;
d=day(s);
DCM=dichloromethane;
DIEA=DIPEA=N,N-diisopropylethylamine;
DMF=N,N-dimethylformamide;
DMSO=dimethylsulfoxide;
DMA=N,N-dimethylacetamide;
dppf=1,1'-bis(diphenylphosphino)ferrocene)
EtOAc=ethyl acetate;
Ex=Example;
FCC=flash column chromatography using silica;
h=hour(s);
LDA=lithium diisopropylamide;
LiHMDS=lithium bis(trimethylsilyl)amide [LiN(SiMe$_3$)$_2$];
MeOH=methanol;
min.=minutes;
Pd$_2$(dba)$_3$=tris(dibenzylideneacetone)dipalladium(0);
Pd(dppf)Cl$_2$=[1,1'-bis(diphenylphosphino)ferrocene]dichloropalladium(II);
r.t.=room temperature;
satd.=saturated solution;
TFA=trifluoroacetic acid;
THF=tetrahydrofuran;
Xantphos=4,5-bis(diphenylphosphino)-9,9-dimethylxanthene (CAS #161265-03-8);
XtalFluor-E=(diethylamino)difluorosulfonium tetrafluoroborate (CAS #63517-29-3);

General Synthetic Schemes

Scheme 1: Where L is absent (i.e. a direct bond)

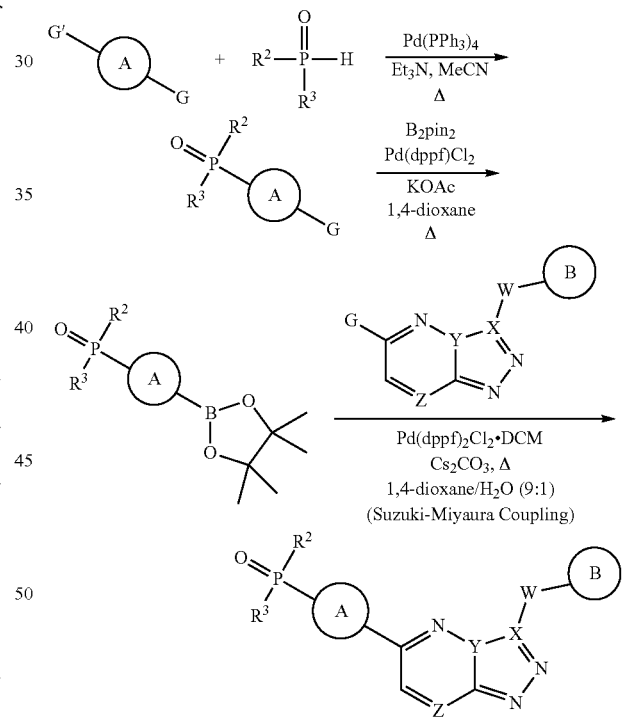

Scheme 2: Where L is absent (i.e. a direct bond)

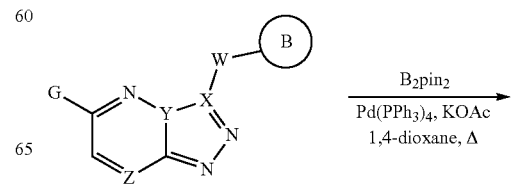

-continued

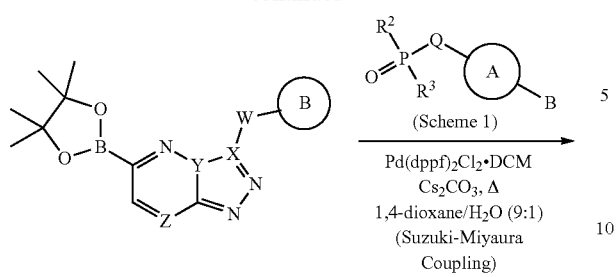
(Scheme 1)
Pd(dppf)₂Cl₂•DCM
Cs₂CO₃, Δ
1,4-dioxane/H₂O (9:1)
(Suzuki-Miyaura Coupling)

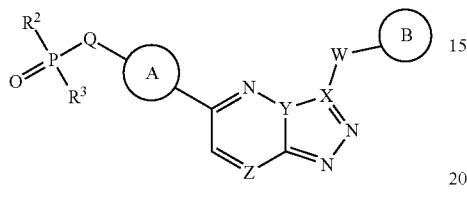

Scheme 3: Where L is NR¹

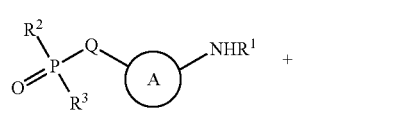

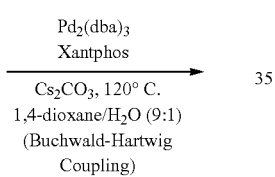
Pd₂(dba)₃
Xantphos
───────────
Cs₂CO₃, 120° C.
1,4-dioxane/H₂O (9:1)
(Buchwald-Hartwig Coupling)

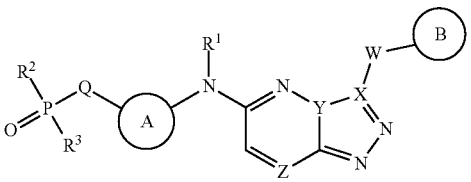

Scheme 4: Where L is O, S or NR¹

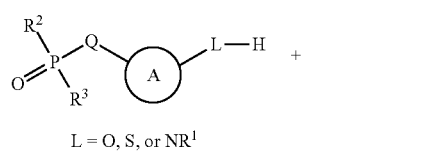

L = O, S, or NR¹

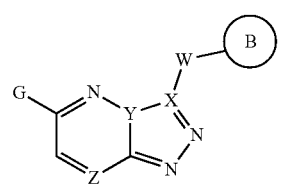
CuI, L-proline
───────────
DMSO, Δ
(Ullman Coupling)

-continued

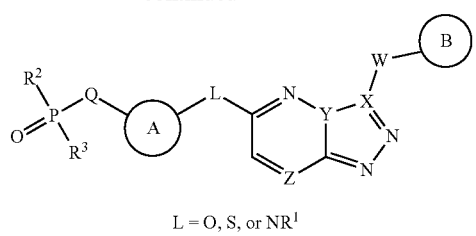

L = O, S, or NR¹

Scheme 5: Where L is O, S or NR¹

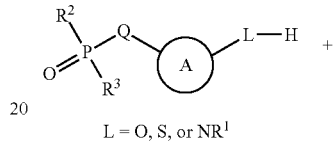

L = O, S, or NR¹

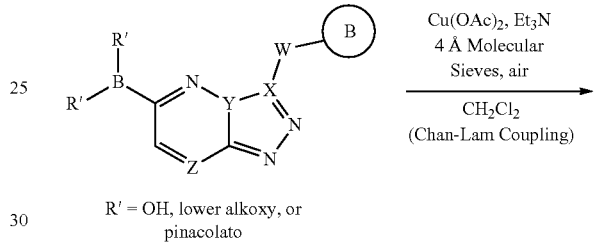
Cu(OAc)₂, Et₃N
4 Å Molecular Sieves, air
───────────
CH₂Cl₂
(Chan-Lam Coupling)

R' = OH, lower alkoxy, or pinacolato

L = O, S, or NR¹

Scheme 6: Where L is O, S or NR¹

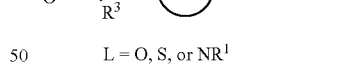

L = O, S, or NR¹

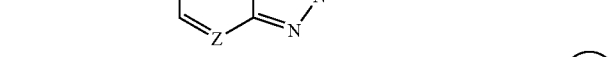
t-BuONa
───────
THF, Δ

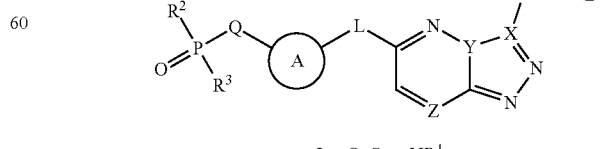

L = O, S, or NR¹

Scheme 7: Where L is CH₂
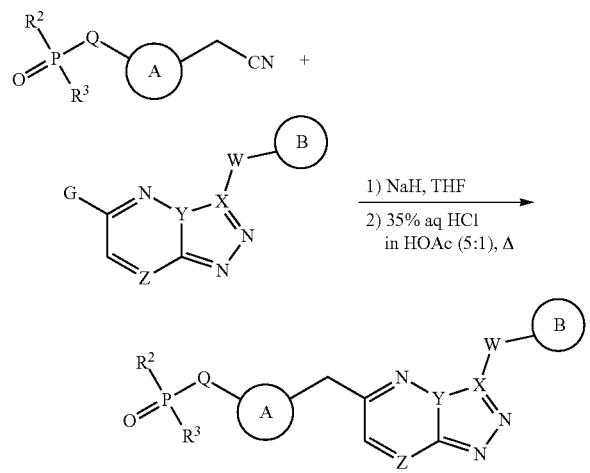
Scheme 8: Where Q is CH₂
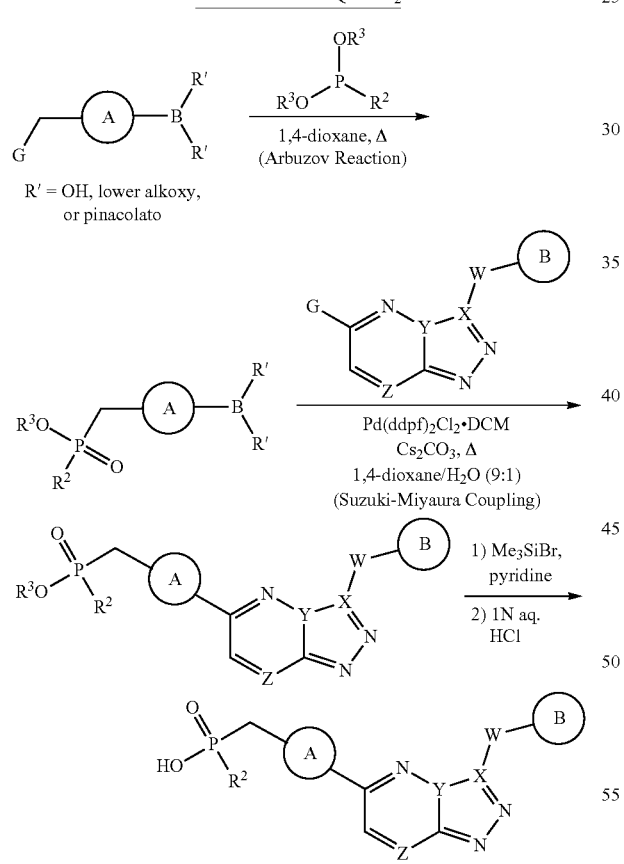
Scheme 9: Synthesis of [1,2,4]triazolo[4,3-b][1,2,4]triazine derivative
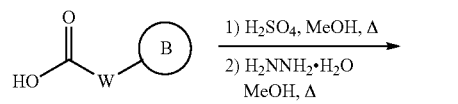
-continued
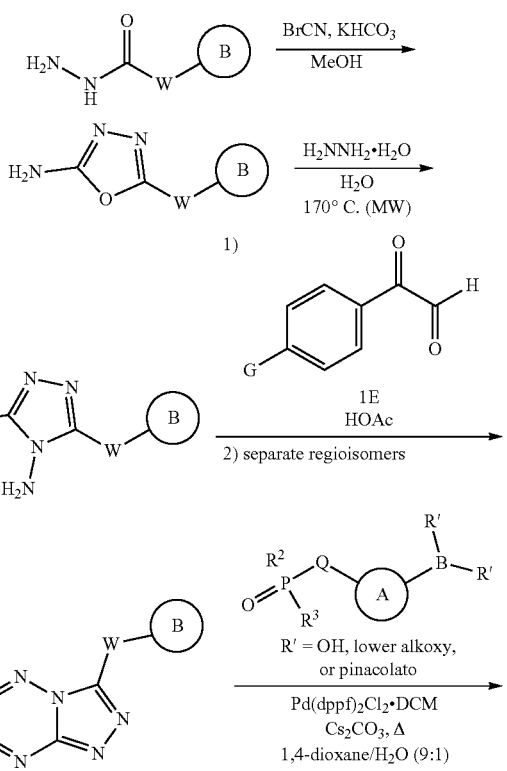
Scheme 10: Synthesis of [1,2,4]triazolo[4,3-b]pyridazine derivatives
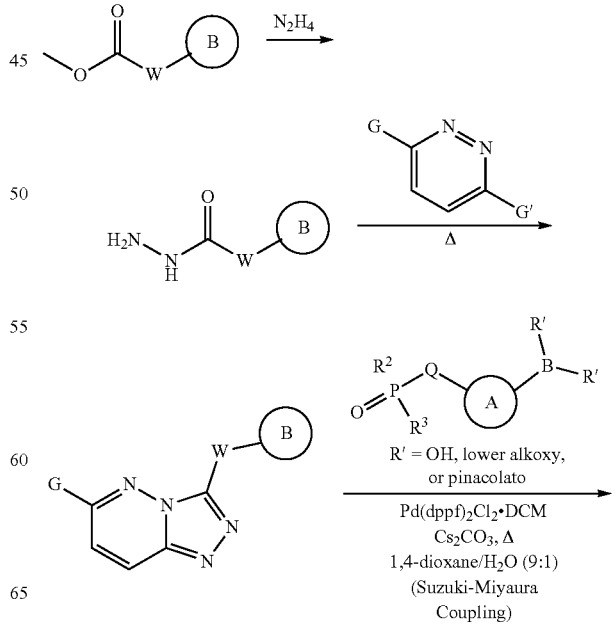

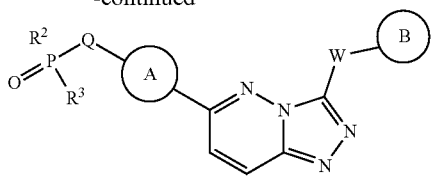

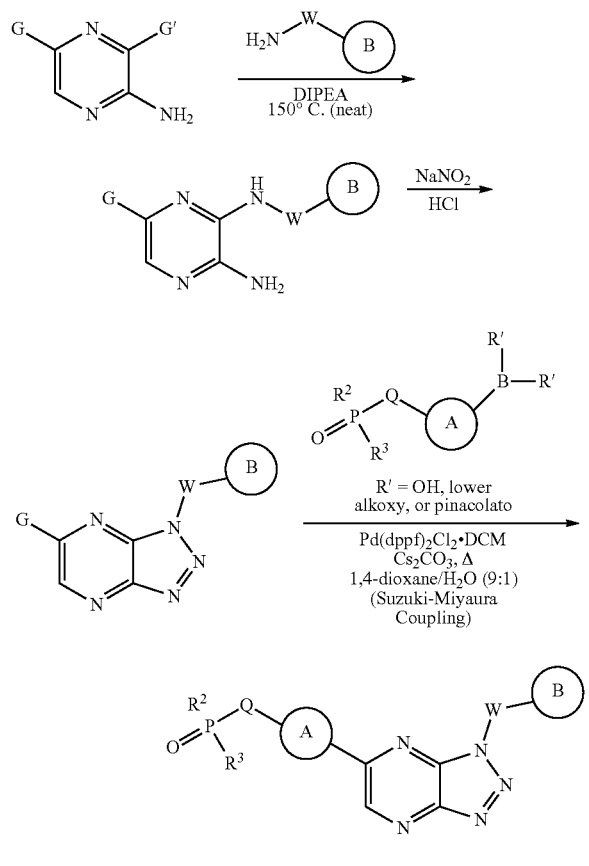

The compounds thus obtained can be further modified at their peripheral positions to provide the desired compounds. Synthetic chemistry transformations are described, for example, in R. Larock *Comprehensive Organic Transformations*, VCH Publishers (1989); T. W. Greene and P.G.M. Wuts, Protective Groups in Organic Synthesis, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. The compounds of the formula IV and/or their pharmaceutically acceptable salts described herein can be purified by column chromatography, high performance liquid chromatography, crystallization, or other suitable methods.

EXAMPLES

The following non-limiting Examples further illustrate certain aspects of the present invention. These compounds were prepared according to the general synthetic schemes described above.

Example 1

Dimethyl(4-(1-(quinolin-6-ylmethyl)-1H-[1,2,3]triazolo[4,5-b]pyrazin-6-yl)phenyl)-phosphine oxide (1)

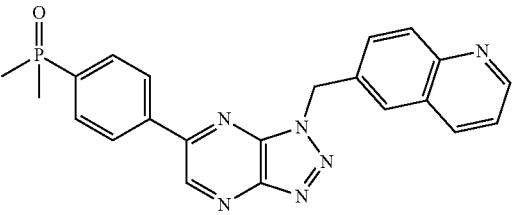

Compound 1 was prepared according to Scheme 12.

Scheme 12

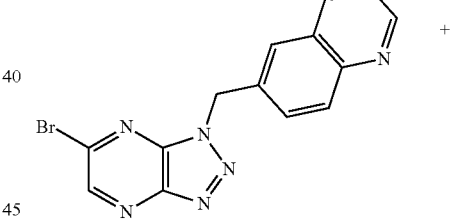

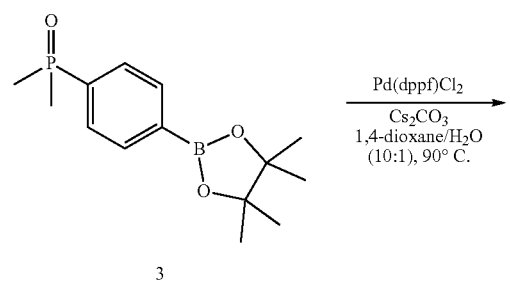

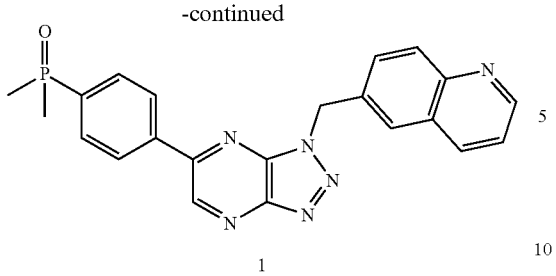

Method A

Dimethyl(4-(1-(quinolin-6-ylmethyl)-1H-[1,2,3]triazolo[4,5-b]pyrazin-6-yl)phenyl)-phosphine oxide (1)

6-((6-Bromo-1H-[1,2,3]triazolo[4,5-b]pyrazine-1-yl)methyl)quinoline (2) (56 mg, 0.16 mmol; CAS #956907-14-5), dimethyl(4-(4,4,5,5-tetramethyl-1,3,2-dioxaborolan-2-yl)phenyl)phosphine oxide (3) (112 mg, 0.40 mmol; CAS #1394346-20-3) and cesium carbonate (156 mg, 0.48 mmol) were combined in 10 mL of 1,4 dioxane/water (10:1). The reaction mixture was degassed with $N_2$, then Pd(dppf)Cl$_2$ (20 mg, 0.02 mmol) was added and the mixture was heated at 90° C. with stirring for 6 h. The mixture was concentrated to dryness and the residue was purified by silica gel chromatography using a MeOH—CH$_2$Cl$_2$ gradient to yield 42 mg of dimethyl(4-(1-(quinolin-6-ylmethyl)-1H-[1,2,3]triazolo[4,5-b]pyrazin-6-yl)phenyl)-phosphine oxide (1) as a tan solid: MS (m/z) MH$^+$ 415; $^1$H NMR (300 MHz, DMSO-d$_6$): δ 1.85 (d, J=13.0 Hz, 6H), 6.27 (s, 2H), 7.52-8.85 (overlapping m, 10H), 9.41 (s, 1H).

Examples 2 and 3

Ethyl methyl(4-(1-(quinolin-6-ylmethyl)-1H-[1,2,3]triazolo[4,5-b]pyrazin-6-yl)benzyl)-phosphinate (4)

Methyl(4-(1-(quinolin-6-ylmethyl)-1H-[1,2,3]triazolo[4,5-b]pyrazin-6-yl)benzyl)-phosphinic Acid (5)

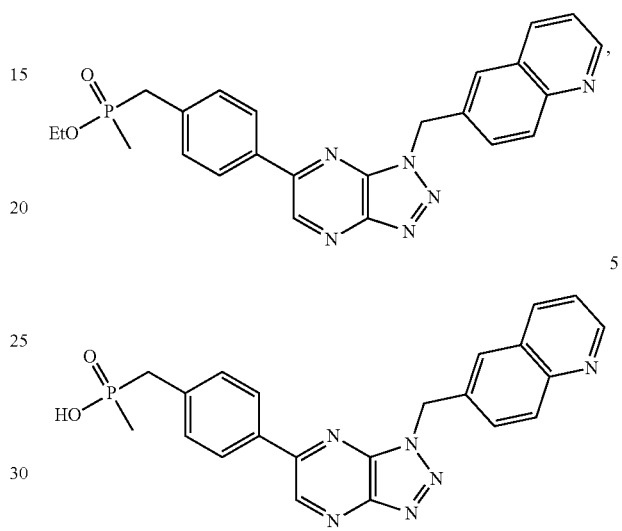

Compounds 4 and 5 were prepared according to Scheme 13.

Scheme 13

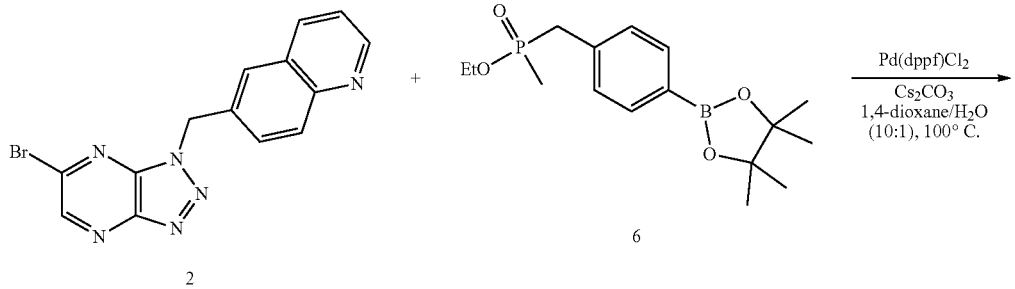

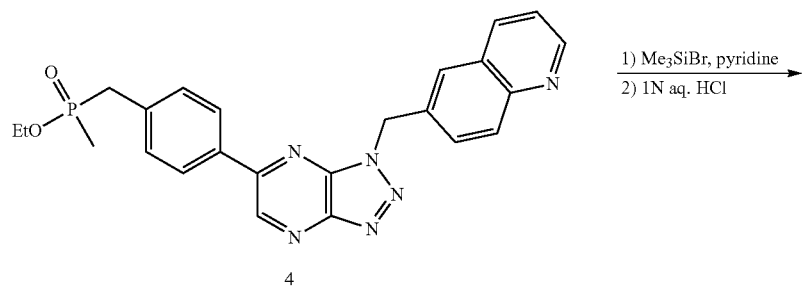

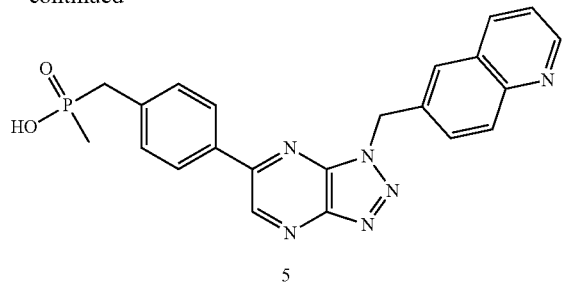

5

Ethyl methyl(4-(1-(quinolin-6-ylmethyl)-1H-[1,2,3]triazolo[4,5-b]pyrazin-6-yl)-benzyl)phosphinate (4)

6-((6-Bromo-1H-[1,2,3]triazolo[4,5-b]pyrazine-1-yl)methyl)-quinoline (2) (585 mg, 1.7 mmol; CAS #956907-14-5), $Cs_2CO_3$, (1.7 g, 5.1 mmol), ethyl methyl(4-(4,4,5,5-tetramethyl-1,3,2-dioxaborolan-2-yl)benzyl)phosphinate (6) (1.4 g, 4.25 mmol; CAS #1273492-75-3) were combined in 10 mL of 1,4 dioxane/water (10:1). The mixture was degassed with $N_2$, then Pd(dppf)Cl$_2$ (140 mg, 0.17 mmol) was added and the mixture was heated with stirring at 100° C. for 3 h. The reaction mixture was concentrated to dryness and the residue was purified by silica gel chromatography using a MeOH—$CH_2Cl_2$ gradient to yield 537 mg of ethyl methyl(4-(1-(quinolin-6-ylmethyl)-1H-[1,2,3]triazolo[4,5-b]pyrazin-6-yl)benzyl)phosphinate (4) as a tan semi-solid: MS (m/z) MH$^+$=459; $^1$H NMR (300 MHz, CD$_4$OD): δ 1.30 (t, J=7.0 Hz, 3H), 3.40 (s, 2H), 4.04-4.09 (m, 2H), 6.23 (s, 2H), 7.50-8.36 (overlapping m, 9H), 8.76-8.84 (m, 1H), 9.32 (s, 1H).

Methyl(4-(1-(quinolin-6-ylmethyl)-1H-[1,2,3]triazolo[4,5-b]pyrazin-6-yl)benzyl)-phosphinic Acid (5)

To a solution of ethyl methyl(4-(1-(quinolin-6-ylmethyl)-1H-[1,2,3]triazolo[4,5-b]pyrazin-6-yl)benzyl)phosphinate (4) (537 mg, 1.0 mmol) in 7 mL of pyridine was added trimethylsilyl bromide (0.4 mL, 3.0 mmol) dropwise with stirring at room temperature. After 2 h, an additional 0.5 mL of trimethylsilyl bromide was added until the conversion was complete, as monitored by LC/MS. After a total of 4 h, the mixture was concentrated and stirred with excess aq. 1N HCl for 2 h. The precipitate was collected, washed thoroughly with water, and then triturated with hot methanol. The resulting solid was collected and dried under vacuum to afford 489 mg of methyl(4-(1-(quinolin-6-ylmethyl)-1H-[1,2,3]triazolo[4,5-b]pyrazin-6-yl)benzyl)-phosphinic acid (5) as a white solid: MS (m/z) MH$^+$=489; $^1$H NMR (300 MHz, DMSO-d$_6$): δ 1.24 (d, J=14.0 Hz, 3H), 3.20 (s, 2H), 6.30 (s, 2H), 7.45-9.17 (m, 10H), 9.45 (s, 1H).

Example 4

(3-Fluoro-4-(1-(quinolin-6-ylmethyl)-1H-[1,2,3]triazolo[4,5-b]pyrazin-6-yl)phenyl)dimethylphosphine oxide (7)

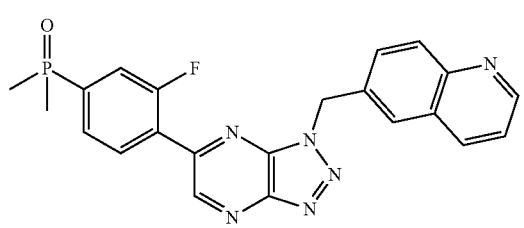

7

Compound 7 was prepared according to Scheme 14.

Scheme 14.

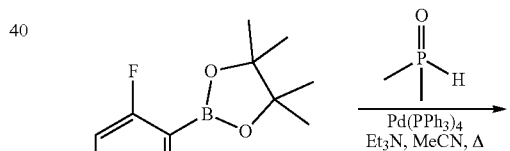

8

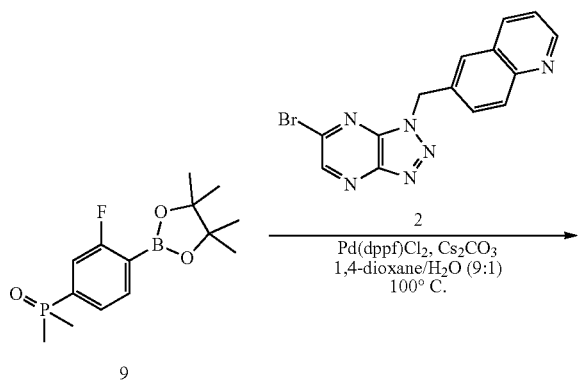

9

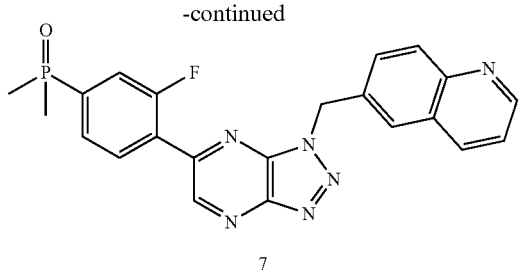

(3-Fluoro-4-(1-(quinolin-6-ylmethyl)-1H-[1,2,3]triazolo[4,5-b]pyrazin-6-yl)phenyl)-dimethylphosphine Oxide (7)

A solution of 2-(4-bromo-2-fluorophenyl)-4,4,5,5-tetramethyl-1,3,2-dioxaborolane (8) (200 mg, 0.67 mmol), dimethylphosphine oxide (53 mg, 0.67 mmol), and triethylamine (2.68 mmol) in 5 mL of $CH_3CN$ was degassed with $N_2$. Tetrakis(triphenylphosphine)palladium(0) (0.033 mmol) was added, and the mixture was stirred and heated at reflux for 7 h, then cooled to room temperature and concentrated in vacuo. The crude product (9) was combined with 6-((6-bromo-1H-[1,2,3]triazolo[4,5-b]pyrazin-1-yl)methyl)quinoline (2) (92 mg, 0.27 mmol; CAS #956907-14-5) and $Cs_2CO_3$ (266 mg, 0.81 mmol) in 10 mL of 9:1 mixture of dioxane/$H_2O$ and degassed with $N_2$. Pd(dppf)$Cl_2$ (124 mg, 0.17 mmol) was added and the mixture was heated at 100° C. for 3 h. The mixture was concentrated and the crude residue was purified by column chromatography (silica gel, gradient of MeOH in $CH_2Cl_2$) followed by trituration of the isolated product with diethyl ether to afford (3-fluoro-4-(1-(quinolin-6-ylmethyl)-1H-[1,2,3]triazolo[4,5-b]pyrazin-6-yl)phenyl)dimethyl-phosphine oxide (7) as a brown semi-solid: MS (m/z) $MH^+$434; $^1$H NMR (300 MHz, $CD_3OD$): δ 1.87 (d, J=13.6 Hz, 6H), 6.28 (s, 2H), 7.33-8.44 (overlapping m, 7H), 8.84-8.53 (m, 1H), 9.25-9.26 (m, 1H).

Example 5

(2-Fluoro-4-(1-(quinolin-6-ylmethyl)-1H-[1,2,3]triazolo[4,5-b]pyrazin-6-yl)phenyl)dimethyl-phosphine Oxide (10)

Compound 10 was prepared according to Scheme 15.

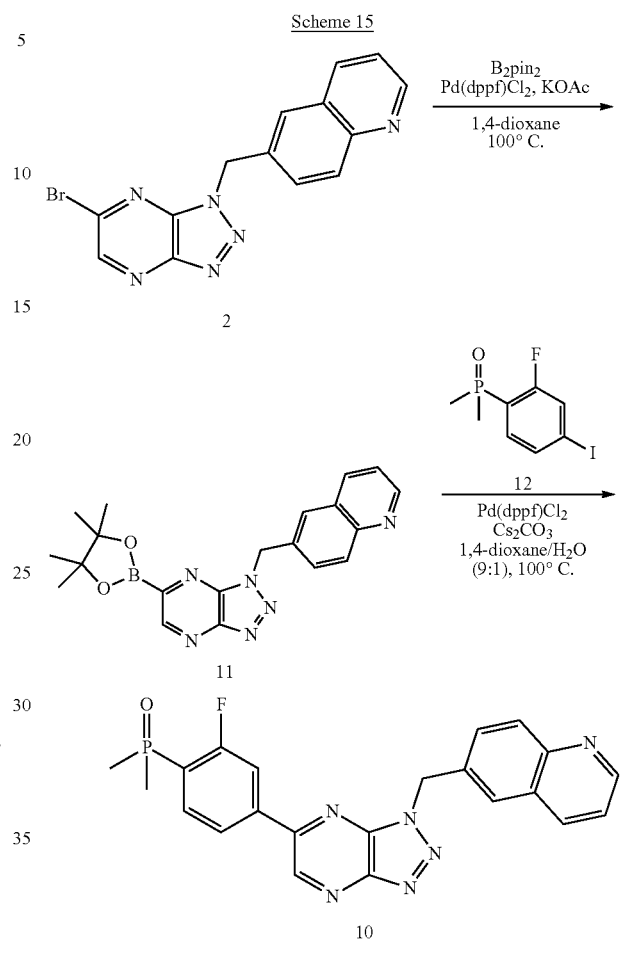

The synthesis of the required starting material (2-fluoro-4-iodophenyl)dimethylphosphine oxide (12) is shown below in Scheme 16.

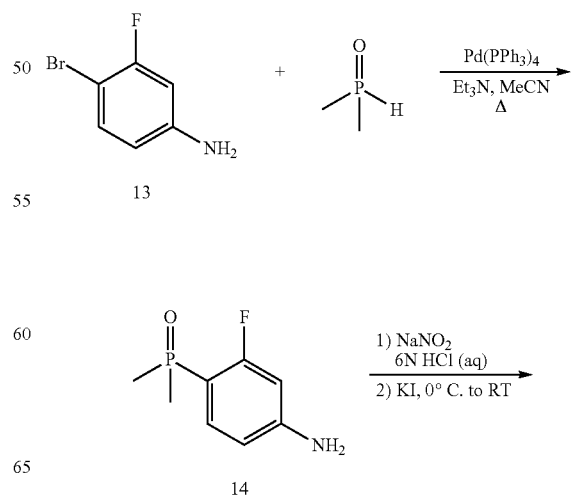

-continued

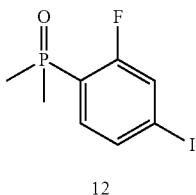

12

Method B (4-Amino-2-fluorophenyl)dimethylphosphine Oxide (14)

Triethylamine (7.5 mL, 53.8 mmol) was added to a stirred, clear colorless solution of 4-bromo-3-fluoroaniline (13) (2.55 g, 13.4 mmol) and dimethylphosphine oxide (1.05 g, 13.4 mmol) in acetonitrile (45 mL) at ambient temperature. The stirred solution was taken through 10 degassing cycles of evacuation (until the solvent just boils) followed by blanketing with $N_2$. Tetrakis(triphenylphosphine) palladium(0) (799 mg, 0.7 mmol) was added to the reaction mixture and the system again taken through 10 degassing cycles. The resulting suspension was then heated at reflux while stirring under $N_2$ and monitored by UPLC-MS. After 2 days, additional dimethylphosphine oxide (0.52 g, 6.7 mmol) and tetrakis(triphenylphosphine) palladium(0) (324.1 mg, 0.3 mmol) were added under $N_2$ purge and the reaction allowed to continue at reflux for a total of 6 days. The cooled reaction was concentrated in vacuo and purified by chromatography on silica gel eluting with a gradient of 1-10% MeOH (containing 2% concd. $NH_4OH$) in $CH_2Cl_2$ to provide 1.0 g of (4-amino-2-fluorophenyl)dimethylphosphine oxide (14) as an off-white solid: MS (m/z) MH$^+$=188; $^1$H NMR (300 MHz, DMSO-$d_6$): δ 7.38-7.28 (m, 1H), 6.46 (d, J=8.3 Hz, 1H), 6.37-6.31 (m, 1H), 6.00 (s, 2H), 1.58 (d, J=13.5 Hz, 6H). $^{13}$C NMR (75 MHz, DMSO-$d_6$): δ 163.8 (d, J=245.0 Hz), 155.1 (d, J=245.0 Hz), 133.8, 110.0 (d, J=9.7 Hz), 107.0 (d, J=103.5 Hz), 99.8 (d, J=26.3 Hz), 19.0 (d, J=71.0 Hz).

(2-Fluoro-4-iodophenyl)dimethylphosphine Oxide (12)

A solution of sodium nitrite (122 mg, 1.8 mmol) in water (3 mL) was slowly added at 0° C. beneath the surface of a solution of (4-amino-2-fluorophenyl)dimethylphosphine oxide (14) (302 mg, 1.6 mmol) in 50 mL of 6 N aq. HCl. The cold, now orange, solution was stirred at 0° C. for 5 min. and then a solution of potassium iodide (401 mg, 2.4 mmol) in water (3 mL) was added in one portion. Gas evolution ($N_2$) occurred and the reaction turned black. Subsequently, the reaction mixture was warmed to room temperature, stirred for 5 min., poured into 20% aq. NaOH and extracted with EtOAc. The organic extract was washed with brine, dried (CaSO$_4$), filtered, and concentrated in vacuo. The residue was purified by chromatography on silica gel eluting with a gradient of 1-10% MeOH in $CH_2Cl_2$ to yield 31.5 mg of (2-fluoro-4-iodophenyl)dimethylphosphine oxide (12) as a white solid: MS (m/z) MH$^+$=299; $^1$H NMR (300 MHz, DMSO-$d_6$): δ 7.82-7.78 (m, 1H), 7.73-7.68 (m, 1H), 7.58-7.49 (m, 1H), 1.83 (d, J=13.8 Hz, 6H); $^{13}$C NMR (75 MHz, DMSO-$d_6$): δ 161.5 (d, J=255.5 Hz), 134.4 (dd, J=13.4, 6.8 Hz), 133.5 (t, J=4.9 Hz), 125.2 (dd, J=31.4, 20.1 Hz), 120.5 (dd, J=95.4, 19.9 Hz), 99.5 (dd, J=11.1, 5.3 Hz), 16.2 (d, J=74.0 Hz).

(2-Fluoro-4-(1-(quinolin-6-ylmethyl)-1H-[1,2,3] triazolo[4,5-b]pyrazin-6-yl)phenyl)-dimethyl-phosphine Oxide (10)

A mixture of 6-((6-bromo-1H-[1,2,3]triazolo[4,5-b]pyrazin-1-yl)methyl)quinoline (2) (50 mg, 0.15 mmol; CAS #956907-14-5), bis(pinacolato)diboron (74 mg, 0.3 mmol) and KOAc (74 mg, 0.75 mmol) in 7 mL of 1,4 dioxane was degassed with $N_2$ for 15 min. Pd(dppf)Cl$_2$ (11 mg, 0.015 mmol) was added and the mixture was heated at reflux with monitoring for consumption of 2. After 3 h, the mixture was cooled to room temperature and concentrated under reduced pressure. The crude product 6-((6-(4,4,5,5-tetramethyl-1,3,2-dioxaborolan-2-yl)-1H-[1,2,3]triazolo[4,5-b]pyrazin-1-yl)methyl)quinoline (11) was combined with (2-fluoro-4-iodophenyl)dimethylphosphine oxide (12) (30 mg, 0.1 mmol) and Cs$_2$CO$_3$ (98 mg, 0.3 mmol) in 10 mL of dioxane/H$_2$O (9:1), and the mixture was degassed with $N_2$. Pd(dppf)Cl$_2$ (8 mg, 0.01 mmol) was added and the mixture was heated to 100° C. for 3.5 h. The resulting mixture was concentrated and the crude product was purified by column chromatography (silica gel, MeOH—CH$_2$Cl$_2$ gradient) to yield 17 mg of (2-fluoro-4-(1-(quinolin-6-ylmethyl)-1H-[1,2,3]triazolo[4,5-b]pyrazin-6-yl)phenyl)dimethyl-phosphine oxide (10) as a tan solid: MS (m/z) MH$^+$=434; $^1$H NMR (300 MHz, CDCl$_3$): δ 1.87 (d, J=13.0 Hz, 6H), 3.20 (s, 2H), 6.18 (s, 2H), 7.42-8.17 (m, 8H), 8.92 (s, 1H), 9.24 (s, 1H).

Example 6

(4-(1-(Imidazo[1,2-a]pyridin-6-ylmethyl)-1H-[1,2,3] triazolo[4,5-b]pyrazin-6-yl)phenyl)dimethylphosphine Oxide (15)

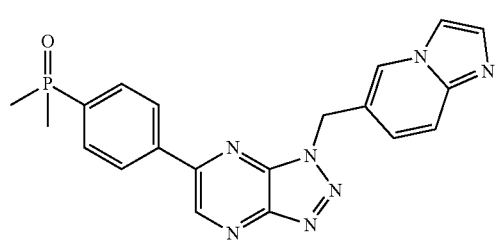

15

Compound 15 was prepared according to Scheme 17.

Scheme 17

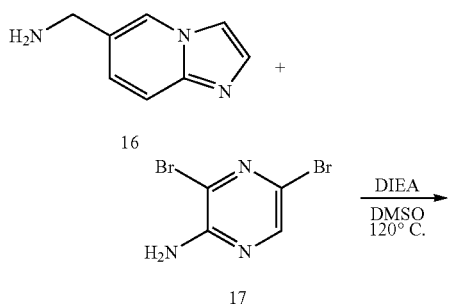

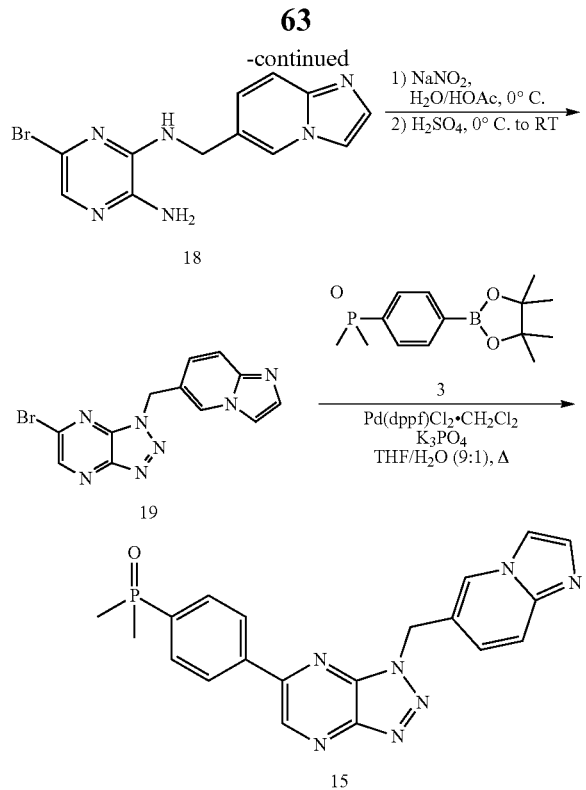

Method C

6-Bromo-N²-(imidazo[1,2-a]pyridin-6-ylmethyl)pyrazine-2,3-diamine (18)

A stirred solution of imidazo[1,2-a]pyridin-6-ylmethanamine (16) (638.7 mg, 3.5 mmol; CAS #132213-03-7), 3,5-dibromopyrazine-2-amine (17) (2.6 g, 10.4 mmol) and N,N-diisopropylethylamine (3.0 mL, 17.2 mmol) in anhydrous DMSO (17.5 mL) was heated at 120° C. under $N_2$ until conversion was complete (4 d). The cooled solution was then partitioned between water and EtOAc and the organic extract was washed with satd. aq. NaCl, dried ($CaSO_4$), and concentrated in vacuo. The residue was purified by chromatography on silica gel eluting with a 1-10% gradient of MeOH (containing 2% concd. $NH_4OH$) in $CH_2Cl_2$. The resulting material was crystallized from boiling EtOAc to give 435 mg of 6-bromo-N²-(imidazo[1,2-a]pyridin-6-ylmethyl)pyrazine-2,3-diamine (18) as a yellow powder: MS (m/z) MH⁺=319.

6-Bromo-1-(imidazo[1,2-a]pyridin-6-ylmethyl)-1H-[1,2,3]triazolo[4,5-b]pyrazine (19)

A cold solution of sodium nitrite (191 mg, 2.8 mmol) in water (1.0 mL) was rapidly added by pipette beneath the surface of a stirred, 0° C. solution of 6-bromo-N²-(imidazo[1,2-a]pyridin-6-ylmethyl)pyrazine-2,3-diamine (18) (588 mg, 1.8 mmol) in 10 mL of a mixture of acetic acid/water (1:1). The reaction was stirred at 0° C. for 30 min and then warmed to room temperature over 1.5 h. Concd. $H_2SO_4$ (50 DL) was added and the reaction stirred at room temperature for 18 h. The solution was chilled and pH adjusted to approximately pH 10 with 20% aq. NaOH and then extracted with EtOAc. The organic extract was dried ($CaSO_4$), filtered and concentrated in vacuo. The resulting residue was purified by chromatography on silica gel eluting with a gradient of 0-5% MeOH in $CH_2Cl_2$ to yield 301 mg of 6-bromo-1-(imidazo[1,2-a]pyridin-6-ylmethyl)-1H-[1,2,3]triazolo[4,5-b]pyrazine (19) as a white solid: MS (m/z) MH⁺=330; ¹H NMR (300 MHz, DMSO-$d_6$): δ 9.01 (s, 1H), 8.71-8.70 (m, 1H), 7.97 (s, 1H), 7.59-7.56 (m, 2H), 7.27 (dd, J=9.3, 1.8 Hz, 1H), 6.01 (s, 2H); ¹³C NMR (75 MHz, DMSO-$d_6$): δ 147.9, 146.3, 144.3, 141.3, 138.6, 134.2, 127.9, 127.2, 126.9, 125.4, 119.9, 117.6, 114.1, 48.6.

(4-(1-(Imidazo[1,2-a]pyridin-6-ylmethyl)-1H-[1,2,3]triazolo[4,5-b]pyrazin-6-yl)-phenyl)dimethylphosphine Oxide (15)

A rapidly stirred mixture of 6-bromo-1-(imidazo[1,2-a]pyridin-6-ylmethyl)-1H-[1,2,3]triazolo[4,5-b]pyrazine (19) (74 mg, 0.2 mmol), dimethyl(4-(4,4,5,5-tetramethyl-1,3,2-dioxaborolan-2-yl)phenyl)phosphine oxide (3) (62 mg, 0.2 mmol), tripotassium phosphate (234 mg, 1.1 mmol), and Pd(dppf)$Cl_2$—$CH_2Cl_2$ (37 mg, 0.05 mmol) in 10 mL of THF/water (9:1) was degassed and then heated at reflux under $N_2$ for 30 min. The cooled reaction was concentrated in vacuo and the residue was purified by chromatography on silica gel eluting with a gradient of 0-10% MeOH in $CH_2Cl_2$ to provide 61 mg of yellow oil which was crystallized from EtOAc/heptane to yield 44 mg of (4-(1-(imidazo[1,2-a]pyridin-6-ylmethyl)-1H-[1,2,3]triazolo[4,5-b]pyrazin-6-yl)phenyl)dimethyl-phosphine oxide (15) as an off-white powder: MS (m/z) MH⁺=404; ¹H NMR (300 MHz, DMSO-$d_6$): δ 9.57 (s, 1H), 8.81 (s, 1H), 8.44 (dd, J=8.2, 1.9 Hz, 2H), 8.04-7.97 (m, 3H), 7.59-7.56 (m, 2H), 7.36 (dd, J=9.3, 1.4 Hz, 1H), 1.73 (d, J=13.4 Hz, 6H).

Example 7

(3-(1-(Imidazo[1,2-a]pyridin-6-ylmethyl)-1H-[1,2,3]triazolo[4,5-b]pyrazin-6-yl)phenyl)-dimethylphosphine Oxide (20)

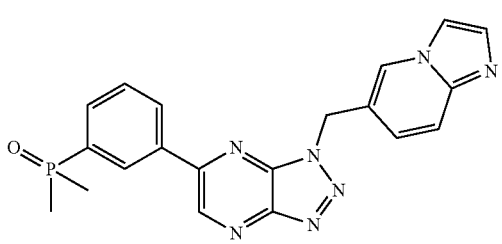

The synthesis of the required starting material (dimethyl (3-(4,4,5,5-tetramethyl-1,3,2-dioxaborolan-2-yl)phenyl) phosphine oxide (21) is shown below in Scheme 18.

Scheme 18

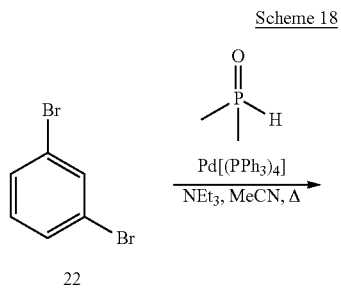

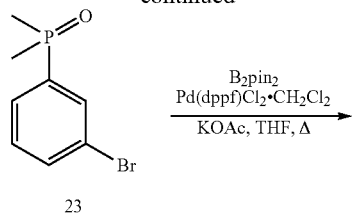

(3-Bromophenyl)dimethylphosphine Oxide (23)

Triethylamine (3.8 mL, 27.3 mmol) was added to an ambient temperature, clear colorless solution of 1,3-dibromobenzene (1.6 g, 6.8 mmol) and dimethylphosphine oxide (0.5 g, 6.6 mmol) in anhydrous acetonitrile (23 mL). The stirred solution was degassed by taking it through 10 evacuations (until the solvent just boils)/$N_2$ blanketing cycles. Tetrakis(triphenylphosphine) palladium(0) (409 mg, 0.4 mmol) was then added and the reaction mixture again taken through 10 degassing cycles. The resulting suspension was heated at reflux while stirring under $N_2$ for 2.5 h. The cooled reaction mixture was filtered and the filtrate was concentrated in vacuo and purified by chromatography on silica gel eluting with a gradient of 0-5% MeOH in $CH_2C_2$ to furnish (3-bromophenyl)-dimethylphosphine oxide (650 mg) as a white solid: MS (m/z) $MH^+$=233; $^1H$ NMR (300 MHz, DMSO-$d_6$): δ 7.97-7.92 (m, 1H), 7.82-7.75 (m, 2H), 7.54-7.46 (m, 1H), 1.67 (d, J=13.5 Hz, 6H); $^{13}C$ NMR (75 MHz, DMSO-$d_6$): δ 139.6 (d, 91.5 Hz), 134.5 (d, 2.3 Hz), 132.7 (d, 10.5 Hz), 131.3 (d, 11.6 Hz), 129.3 (d, 9.2 Hz), 122.6 (d, 14.3 Hz), 18.0 (d, 70.6 Hz).

Dimethyl(3-(4,4,5,5-tetramethyl-1,3,2-dioxaborolan-2-yl)phenyl)phosphine Oxide (21)

A mixture of (3-bromophenyl)dimethylphosphine oxide (23) (647 mg, 2.8 mmol), bis(pinacolato)diboron (1.4 g, 5.6 mmol), potassium acetate (1.4 g, 13.9 mmol) and [1,1'-bis(diphenylphosphino)ferrocene]dichloropalladium(II) complex with dichloromethane (456 mg, 0.6 mmol) in anhydrous THF (13.9 mL) was degassed and heated at reflux for 2 h. The cooled reaction mixture was partitioned between satd. aq. NaCl and ethyl acetate. The organic layer was dried ($CaSO_4$), filtered, concentrated in vacuo and purified by chromatography on silica gel eluting with a gradient of 0-10% MeOH in $CH_2Cl_2$. The resulting material was recrystallized from a mixture of EtOAc and heptane to provide 330 mg of dimethyl(3-(4,4,5,5-tetramethyl-1,3,2-dioxaborolan-2-yl)phenyl)phosphine oxide (21) as a light brown crystalline powder: MS (m/z) $MH^+$=281.

(3-(1-(Imidazo[1,2-a]pyridin-6-ylmethyl)-1H-[1,2,3]triazolo[4,5-b]pyrazin-6-yl)phenyl)dimethylphosphine Oxide (20)

Compound 20 was prepared by a procedure analogous to Example 6 by substituting dimethyl(4-(4,4,5,5-tetramethyl-1,3,2-dioxaborolan-2-yl)phenyl)phosphine oxide (3) with dimethyl(3-(4,4,5,5-tetramethyl-1,3,2-dioxaborolan-2-yl)phenyl)phosphine oxide (21) to afford compound 20 as an off-white powder: MS (m/z) $MH^+$=404; $^1H$ NMR (300 MHz, DMSO-$d_6$): δ 9.58 (s, 1H), 8.83 (s, 1H), 8.67 (d, J=11.9 Hz, 1H), 8.49 (d, J=7.5 Hz, 1H), 8.04-7.97 (m, 2H), 7.78 (ddd, J=7.7, 7.7, 2.6 Hz, 1H), 7.60-7.57 (m, 2H), 7.37 (dd, J=9.3, 1.5 Hz, 1H), 6.10 (s, 2H), 1.77 (d, J=13.4 Hz, 6H).

Example 8

Dimethyl(3-(1-(quinolin-6-ylmethyl)-1H-[1,2,3]triazolo[4,5-b]pyrazin-6-yl)phenyl)phosphine Oxide (24)

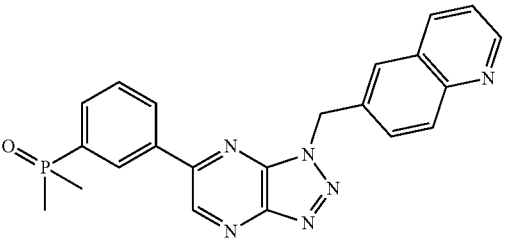

Compound 24 was prepared from 2 by a procedure analogous to the one described for Example 1 by substituting dimethyl(4-(4,4,5,5-tetramethyl-1,3,2-dioxaborolan-2-yl)phenyl)-phosphine oxide (3) with dimethyl(3-(4,4,5,5-tetramethyl-1,3,2-dioxaborolan-2-yl)phenyl)-phosphine oxide (21) to afford dimethyl(3-(1-(quinolin-6-ylmethyl)-1H-[1,2,3]triazolo[4,5-b]pyrazin-6-yl)phenyl)phosphine oxide (24) as a white powder: MS (m/z) $MH^+$=415; (300 MHz, DMSO-$d_6$): δ 9.59 (s, 1H), 8.90 (d, J=2.8 Hz, 1H), 8.64 (d, J=11.8 Hz, 1H), 8.47 (d, J=7.6 Hz, 1H), 8.41 (d, J=8.1 Hz, 1H), 8.07-7.96 (m, 3H), 7.89-7.86 (m, 1H), 7.79-7.75 (m, 1H), 7.56-7.52 (m, 1H), 6.28 (s, 2H), 1.75 (d, J=13.4 Hz, 6H).

Example 9

Dimethyl((4-(1-(quinolin-6-ylmethyl)-1H-[1,2,3]triazolo[4,5-b]pyrazin-6-yl)-1H-pyrazol-1-yl)methyl)phosphine Oxide (25)

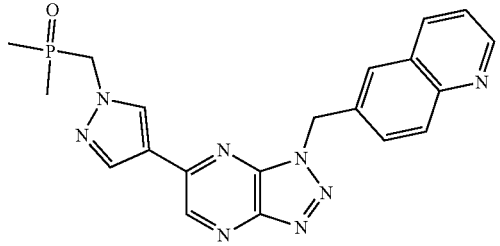

Compound 25 was prepared according to Scheme 19.

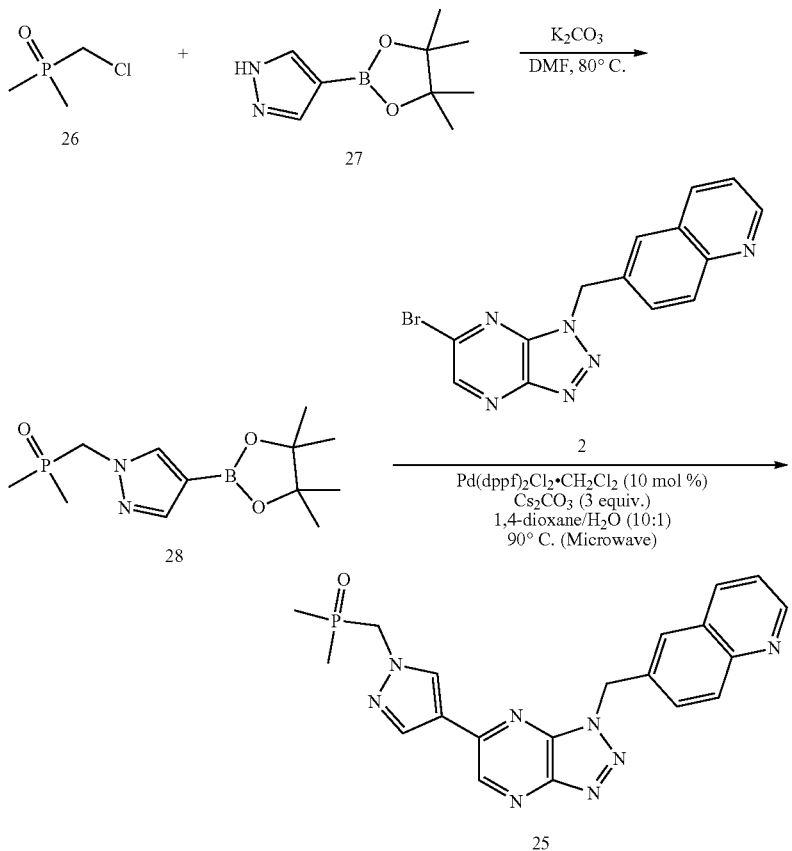

Method D

Dimethyl((4-(4,4,5,5-tetramethyl-1,3,2-dioxaborolan-2-yl)-1H-pyrazol-1-yl)methyl)-phosphine Oxide (28)

Potassium carbonate (1.31 g, 9.48 mmol) was added in one portion to a solution of (chloromethyl)dimethylphosphine oxide (26) (792 mg, 6.26 mmol) and 4-(4,4,5,5-tetramethyl-1,3,2-dioxaborolan-2-yl)-1H-pyrazole (27) (614 mg, 3.16 mmol) in anhydrous DMF (32 mL). The resulting slurry was heated at 80° C. while stirring under $N_2$ for 36 h, cooled to room temperature, filtered and the filtrate was concentrated in vacuo. The residue was triturated with hexane and purified by chromatography on silica gel eluting with a gradient of 0-15% MeOH in $CH_2Cl_2$ to afford 554 mg (62%) of dimethyl((4-(4,4,5,5-tetramethyl-1,3,2-dioxaborolan-2-yl)-1H-pyrazol-1-yl)methyl)-phosphine oxide (28) as a white solid. MS (m/z) $MH^+$=285; $^1H$ NMR (300 MHz, $CDCl_3$): δ 7.80 (s, 1H), 7.77 (s, 1H), 4.58 (d, J=8.41 Hz, 2H), 1.53 (d, J=13.1 Hz, 6H), 1.32 (s, 12H).

Dimethyl((4-(1-(quinolin-6-ylmethyl)-1H-[1,2,3]triazolo[4,5-b]pyrazin-6-yl)-1H-pyrazol-1-yl)methyl)phosphine Oxide (25)

6-((6-Bromo-1H-[1,2,3]triazolo[4,5-b]pyrazine-1-yl)methyl)quinoline (2) (50 mg, 0.1466 mmol; CAS #956907-14-5), dimethyl((4-(4,4,5,5-tetramethyl-1,3,2-dioxaborolan-2-yl)-1H-pyrazol-1-yl)methyl)phosphine oxide (28) (50 mg, 0.1759 mmol), $Cs_2CO_3$ (143 mg, 0.4398 mmol) and 5.5 mL of 1,4-dioxane/$H_2O$ (10:1) were added to a 10 mL microwave reaction tube fitted with a magnetic stir bar and a septum. The reaction mixture was degassed by slowly bubbling $N_2$ throughout the reaction mixture with stirring for 1 h. Pd(dppf)$Cl_2$—$CH_2Cl_2$ (12 mg, 0.0147 mmol) was added, the degassing continued for an additional 10 min and then the reaction tube was placed on a CEM Discover microwave reactor at 90° C. for 16 h. The reaction was cooled to room temperature and concentrated in vacuo. The residue was triturated with 3 times with 10 mL portions of a mixture of $CH_2Cl_2$/MeOH (9:1). The combined triturations were concentrated in vacuo and the residue was purified by chromatography on silica gel eluting with a gradient of 0-10% MeOH in $CH_2Cl_2$ to furnish 51 mg (69%) of dimethyl((4-(1-(quinolin-6-ylmethyl)-1H-[1,2,3]triazolo[4,5-b]pyrazin-6-yl)-1H-pyrazol-1-yl)methyl)phosphine oxide (25) as a tan solid: MS (m/z) $MH^+$=419; $^1H$ NMR (300 MHz, $CD_3OD$): δ 9.10 (s, 1H), 8.84, J=4.3, 1.4 Hz, 1H), 8.57 (s, 1H), 8.40-8.30 (m, 2H), 8.40-8.20 (m, 2H), 7.89 (dd, J=8.9, 1.8 Hz, 1H), 7.54 (dd, J=8.4, 4.3 Hz, 1H), 6.18 (s, 1H), 4.85 (d, J=7.1 Hz, 2H), 1.64 (d, J=13.5 Hz, 6H).

Example 10

((4-(1-(Imidazo[1,2-a]pyridin-6-ylmethyl)-1H-[1,2,3]triazolo[4,5-b]pyrazin-6-yl)-1H-pyrazol-1-yl)methyl)dimethylphosphine Oxide (29)

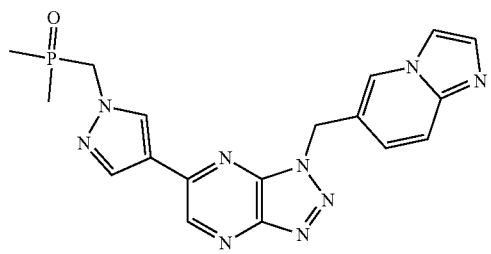

Compound 29 was prepared by procedures analogous to those described for Example 9 by substituting 6-((6-bromo-1H-[1,2,3]triazolo[4,5-b]pyrazine-1-yl)methyl)quinoline (2) with 6-bromo-1-(imidazo[1,2-a]pyridin-6-ylmethyl)-1H-[1,2,3]triazolo[4,5-b]pyrazine (19) to afford ((4-(1-(imidazo[1,2-a]pyridin-6-ylmethyl)-1H-[1,2,3]triazolo[4,5-b]pyrazin-6-yl)-1H-pyrazol-1-yl)methyl)dimethylphosphine oxide (29) as an off-white powder: MS (m/z) MH$^+$=408; $^1$H NMR (300 MHz, DMSO-d$_6$): δ 9.25 (s, 1H), 8.77 (s, 1H), 8.67 (s, 1H), 8.44 (s, 1H), 8.00 (s, 1H), 7.59-7.56 (m, 2H), 7.34 (d, J=8.8 Hz, 1H), 5.99 (s, 2H), 4.81 (d, J=9.2 Hz, 2H), 1.50 (d, J=13.4 Hz, 6H).

Example 11

Dimethyl(4-((1-(quinolin-6-ylmethyl)-1H-[1,2,3]triazolo[4,5-b]pyrazin-6-yl)amino)phenyl)phosphine Oxide (30)

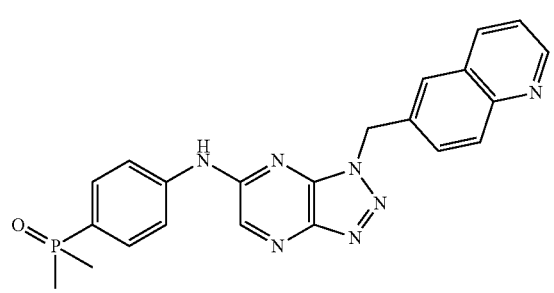

Scheme 20

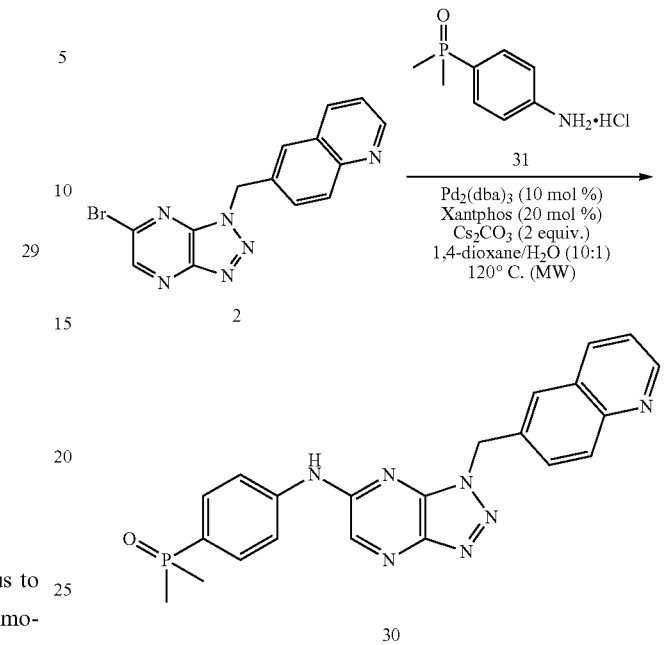

Compound 30 was prepared according to Scheme 20.
Method E

Dimethyl(4-((1-(quinolin-6-ylmethyl)-1H-[1,2,3]triazolo[4,5-b]pyrazin-6-yl)amino)-phenyl)phosphine Oxide (30)

6-((6-Bromo-1H-[1,2,3]triazolo[4,5-b]pyrazin-1-yl)methyl)-quinoline (2) (68 mg, 0.1993 mmol; CAS #956907-14-5), (4-aminophenyl)dimethylphosphine oxide hydrochloride (31) (45 mg, 0.2192 mmol), Cs$_2$CO$_3$ (130 mg, 0.3986 mmol) and 5.5 mL of 1,4-dioxane/H$_2$O (10;1) were added to a 10 mL microwave reaction tube fitted with a magnetic stir bar and a septum. The reaction mixture was degassed by slowly bubbling N$_2$ throughout the reaction mixture with stirring for 1 h. Pd$_2$(dba)$_3$ (18 mg, 0.0199 mmol) and Xantphos (23 mg, 0.0398 mmol) were added, the degassing continued for an additional 10 min and then the reaction tube was placed on a CEM Discover microwave reactor at 120° C. for 16 h. The reaction was cooled to room temperature and concentrated in vacuo. The residue was triturated with 3 times with 10 mL portions of a mixture of CH$_2$Cl$_2$/MeOH (9:1). The combined triturations were concentrated in vacuo and the residue was purified by chromatography on silica gel eluting with a gradient of 0-15% MeOH in CH$_2$Cl$_2$ to furnish 13 mg (15%) of dimethyl(4-((1-(quinolin-6-ylmethyl)-1H-[1,2,3]triazolo[4,5-b]pyrazin-6-yl)amino)phenyl)phosphine oxide (30) as an off-white solid: MS (m/z) MH$^+$=430; $^1$H NMR (300 MHz, CD$_3$OD): δ 8.85 (dd, J=4.3, 1.6 Hz, 1H), 8.40 (broad d, J=8.4 Hz, 1H), 8.31 (s, 1H), 8.09 (d, J=1.6 Hz, 1H), 8.04 (d, J=8.8 Hz, 1H), 7.95-7.86 (m, 2H), 7.82, (dd, J=8.8, 2.0 Hz, 1H), 7.70-7.60 (m, 2H), 7.57 (dd, J=8.4, 4.4 Hz, 1H), 6.07 (s, 2H), 1.78 (d, J=13.4 Hz, 6H).

Example 12

(2-Fluoro-4-((1-(quinolin-6-ylmethyl)-1H-[1,2,3]triazolo[4,5-b]pyrazin-6-yl)amino)phenyl)dimethylphosphine Oxide (32)

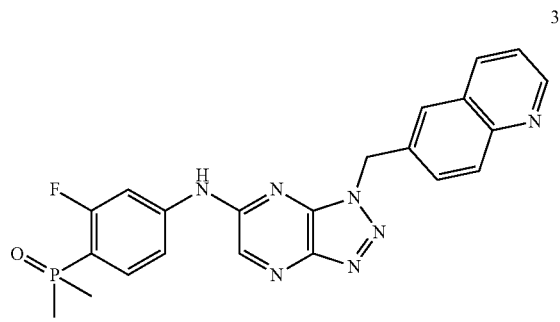

Compound 32 was prepared according to Scheme 21.

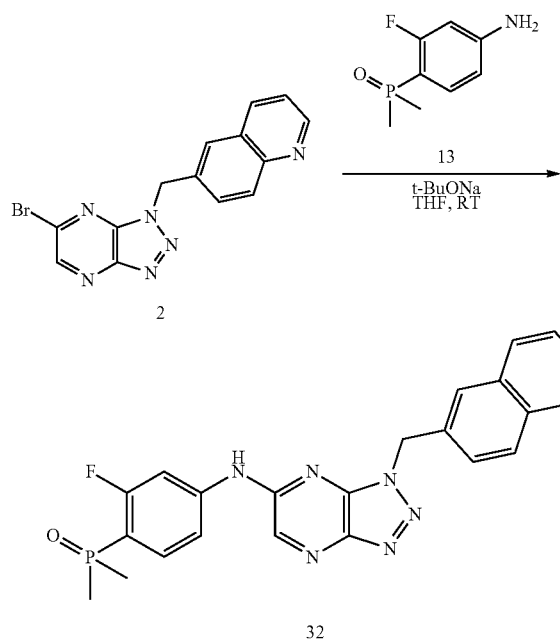

Method F (2-Fluoro-4-((1-(quinolin-6-ylmethyl)-1H-[1,2,3]triazolo[4,5-b]pyrazin-6-yl)amino)phenyl)dimethylphosphine Oxide (32)

Sodium tert-butoxide (124 mg, 1.3 mmol) was added at ambient temperature to a stirred suspension of (4-amino-2-fluorophenyl)dimethylphosphine oxide (125 mg, 0.7 mmol) and 6-((6-bromo-1H-[1,2,3]triazolo[4,5-b]pyrazin-1-yl)methyl)quinoline (2) (207 mg, 0.6 mmol) in anhydrous THF (6.1 mL). The reaction mixture was stirred at room temperature for 15 min and the resulting dark brown solution was concentrated in vacuo. The residue was purified by chromatography on silica gel eluting with a 0-10% MeOH gradient in EtOAc. The resulting material was subsequently crystallized from boiling EtOAc to yield 41 mg of (2-fluoro-4-((1-(quinolin-6-ylmethyl)-1H-[1,2,3]triazolo[4,5-b]pyrazin-6-yl)amino)phenyl)dimethylphosphine oxide (32) as a light yellow powder. An analytical sample was prepared by addition of excess anhydrous 4N HCl in 1,4-dioxane to a MeOH solution of product and evaporation to dryness. The residue was redissolved in MeOH, diluted with diethyl ether and the resulting precipitate was isolated by filtration to afford the HCl salt of 32 as an off-white solid: MS (m/z) MH$^+$=448; $^1$H NMR (300 MHz, CD$_3$OD): δ 8.85-8.83 (m, 1H), 8.39 (d, J=8.2 Hz, 1H), 8.32 (s, 1H), 8.09 (s, 1H), 8.05 (s, 1H), 8.02-7.95 (m, 1H), 7.83 (dd, J=8.8, 2.0 Hz, 1H), 7.72-7.63 (m, 1H), 7.58-7.53 (m, 2H), 6.10 (s, 2H), 1.83 (d, J=13.7 Hz, 6H).

Example 13

(3-(3-(Difluoro(imidazo[1,2-a]pyridin-6-yl)methyl)-[1,2,4]triazolo[4,3-b]pyridazin-6-yl)phenyl)dimethylphosphine Oxide (33)

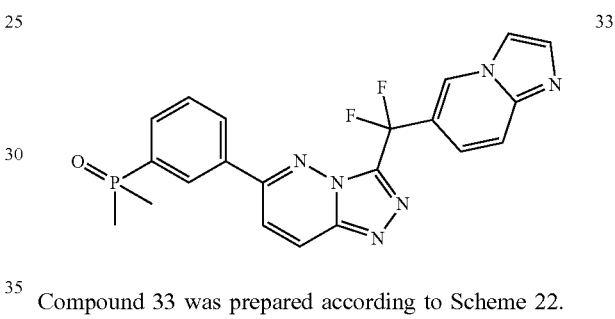

Compound 33 was prepared according to Scheme 22.

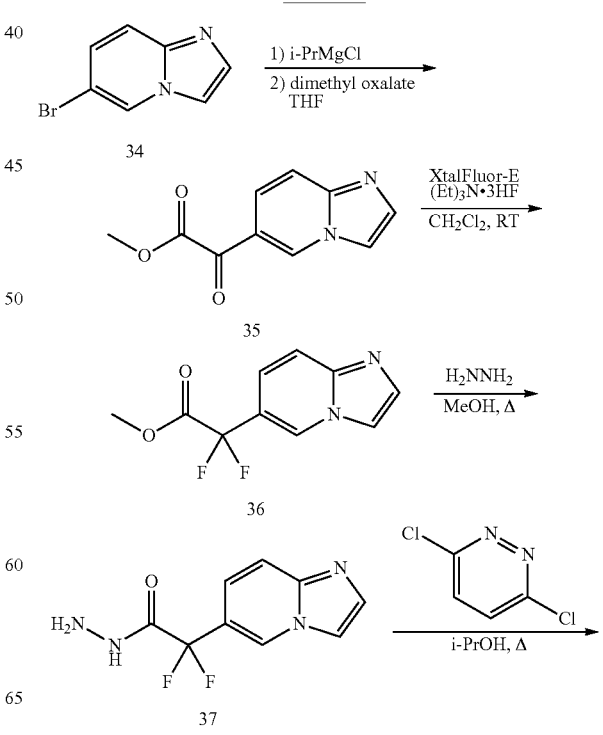

73
-continued

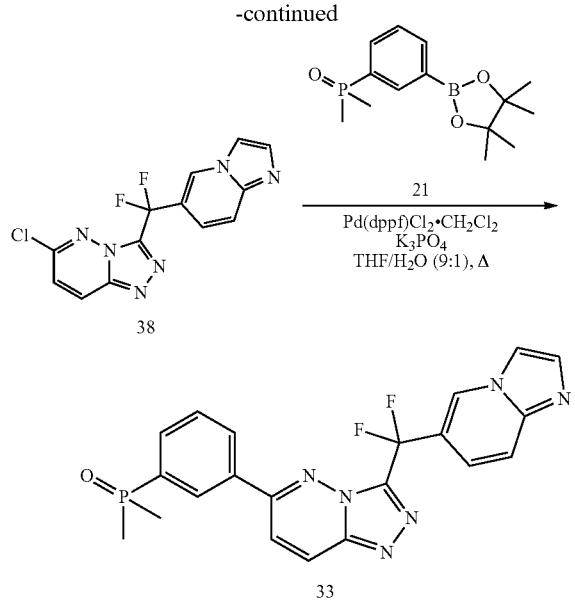

Method G

Methyl 2-(imidazo[1,2-a]pyridin-6-yl)-2-oxoacetate (35)

A solution of isopropyl magnesium chloride in THF (2.0 M; 8.5 mL, 17.0 mmol) was added while stirring under $N_2$ at room temperature to a clear yellow solution of 6-bromoimidazo[1,2-a]pyridine (34) (3.03 g, 15.4 mmol) in anhydrous THF (77 mL). The resulting opaque black suspension was stirred at ambient temperature for 2 h. A solution of dry dimethyl oxalate (3.64 g, 30.8 mmol) in anhydrous THF (16 mL) was added to the reaction mixture in one portion at room temperature. After 20 min, the reaction mixture was poured into 200 mL of satd. aq. NaCl containing ammonium chloride (1.8 g, 34.0 mmol) and extracted with EtOAc. The combined EtOAc extracts were washed with satd. aq. $NaHCO_3$, satd. aq. NaCl, dried ($CaSO_4$), filtered and concentrated in vacuo. The resulting residue was purified by chromatography on silica gel eluting with a gradient of 0-5% methanol in $CH_2Cl_2$ over to furnish 595 mg of methyl 2-(imidazo[1,2-a]pyridin-6-yl)-2-oxoacetate (35) as a yellow solid: MS (m/z) MH$^+$=205; $^1$H NMR (300 MHz, DMSO-$d_6$): δ 9.57-9.56 (m, 1H), 8.20 (m, 1H), 7.72-7.64 (m, 2H), 3.97 (s, 3H); $^{13}$C NMR (75 MHz, DMSO): δ 183.6, 163.3, 145.3, 136.0, 135.7, 122.4, 119.0, 117.7, 116.1, 53.7.

Methyl 2,2-difluoro-2-(imidazo[1,2-a]pyridin-6-yl)acetate (36)

Triethylamine trihydrofluoride (0.95 mL, 5.8 mmol) was added at room temperature under $N_2$ to a stirring suspension of methyl 2-(imidazo[1,2-a]pyridin-6-yl)-2-oxoacetate (35) (430 mg, 1.9 mmol) and XtalFluor-E (1.3 g, 5.8 mmol) in anhydrous $CH_2Cl_2$ (20 mL). After 18 h the reaction appeared as a clear brown solution. The reaction mixture was cautiously quenched by slowly pouring into 100 mL of satd. aq. $NaHCO_3$ and then extracted with additional $CH_2Cl_2$. The organic layer was dried over $CaSO_4$, filtered and concentrated in vacuo to yield 430 mg methyl 2,2-difluoro-2-(imidazo[1,2-a]pyridin-6-yl)acetate (36) as a light yellow crystalline solid: MS (m/z) MH$^+$=227.

74

2,2-Difluoro-2-(imidazo[1,2-a]pyridin-6-yl)acetohydrazide (37)

To a solution of methyl 2,2-difluoro-2-(imidazo[1,2-a]pyridin-6-yl)acetate (36) (791, mg, 3.5 mmol) in MeOH (125 mL) was added anhydrous hydrazine (1.1 mL, 35.0 mmol) and the resulting solution was heated at reflux for 18 h. The reaction mixture was cooled to room temperature and concentrated in vacuo. The residue was purified by chromatography on silica gel eluting with a gradient of 1-10% MeOH (containing 2% concd. $NH_4OH$) in $CH_2Cl_2$ to afford 243 mg of 2,2-difluoro-2-(imidazo[1,2-a]pyridin-6-yl)acetohydrazide (37) as a yellow solid: MS (m/z) MH$^+$=227.

6-Chloro-3-(difluoro(imidazo[1,2-a]pyridin-6-yl)methyl)-[1,2,4]triazolo[4,3-b]pyridazine (38)

A mixture of 2,2-difluoro-2-(imidazo[1,2-a]pyridin-6-yl)acetohydrazide (37) (185 mg, 0.8 mmol) and 3,6-dichloropyridazine (2.4 g, 16.3 mmol) in 2-propanol (82 mL) was heated at reflux while stirring under $N_2$ for 10 d and the resulting solution was cooled to room temperature and concentrated in vacuo. The residue was purified by chromatography on silica gel eluting with a gradient of 0-10% MeOH in $CH_2Cl_2$ to provide 203 mg of 6-chloro-3-(difluoro(imidazo[1,2-a]pyridin-6-yl)methyl)-[1,2,4]triazolo[4,3-b]pyridazine (38) as a yellow solid: MS (m/z) MH$^+$=321.

(3-(3-(Difluoro(imidazo[1,2-a]pyridin-6-yl)methyl)-[1,2,4]triazolo[4,3-b]pyridazin-6-yl)phenyl)dimethylphosphine oxide (33)

A mixture of 6-chloro-3-(difluoro(imidazo[1,2-a]pyridin-6-yl)methyl)-[1,2,4]triazolo[4,3-b]pyridazine (38) (133 mg, 0.4 mmol), dimethyl(3-(4,4,5,5-tetramethyl-1,3,2-dioxaborolan-2-yl)phenyl)phosphine oxide (21) (123 mg, 0.4 mmol), tripotassium phosphate (435 mg, 2.1 mmol), and [1,1'-bis(diphenylphosphino) ferrocene] dichloropalladium (II) complex with dichloromethane (72 mg, 0.1 mmol) in 10 mL of THF/$H_2O$ (9:1) was degassed and then heated at reflux while stirring under $N_2$ for 1.5 h. The cooled reaction mixture was concentrated in vacuo and purified by chromatography on silica gel eluting with a gradient of 2-5% MeOH in $CH_2Cl_2$. The resulting material was crystalized from EtOAc/heptane to afford 15.2 mg of (3-(3-(difluoro(imidazo[1,2-a]pyridin-6-yl)methyl)-[1,2,4]triazolo[4,3-b]pyridazin-6-yl)phenyl)dimethylphosphine oxide (33) as a fine white powder: MS (m/z) MH$^+$=439; $^1$H NMR (300 MHz, DMSO-$d_6$): δ 9.16 (s, 1H), 8.67 (d, J=9.9 Hz, 1H), 8.43 (d, J=11.8 Hz, 1H), 8.23 (d, J=9.9 Hz, 1H), 8.17-8.15 (m, 2H), 8.02-7.96 (m, 1H), 7.78-7.70 (m, 3H), 7.47 (dd, J=9.5, 1.8 Hz, 1H), 1.71 (d, J=13.4 Hz, 6H).

Example 14

(4-(3-(Difluoro(imidazo[1,2-a]pyridin-6-yl)methyl)-[1,2,4]triazolo[4,3-b]pyridazin-6-yl)phenyl)dimethylphosphine Oxide (39)

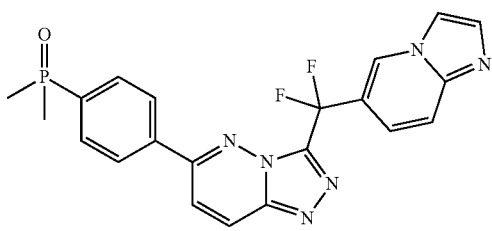

Compound 39 was prepared from 6-chloro-3-(difluoro(imidazo[1,2-a]pyridin-6-yl)methyl)-[1,2,4]triazolo[4,3-b]pyridazine (38) by a procedure analogous to Method G of Example 13 by substituting dimethyl(3-(4,4,5,5-tetramethyl-1,3,2-dioxaborolan-2-yl)phenyl)phosphine oxide (21) with dimethyl(4-(4,4,5,5-tetramethyl-1,3,2-dioxaborolan-2-yl)phenyl)phosphine oxide (3) to afford compound 39 as a light pink powder: MS (m/z) MH+=439; $^1$H NMR (300 MHz, DMSO-$d_6$): δ 8.70 (d, J=9.8 Hz, 1H), 8.22 (d, J=9.8 Hz, 1H), 8.15-8.12 (m, 2H), 8.02-7.87 (m, 4H), 7.67 (d, J=1.2 Hz, 1H), 7.60-7.58 (m, 1H), 7.52-7.46 (m, 1H), 1.71 (d, J=13.4 Hz, 6H).

Example 15

(4-(1-(1-(Imidazo[1,2-a]pyridin-6-yl)ethyl)-1H-[1,2,3]triazolo[4,5-b]pyrazin-6-yl)phenyl)dimethylphosphine Oxide (40)

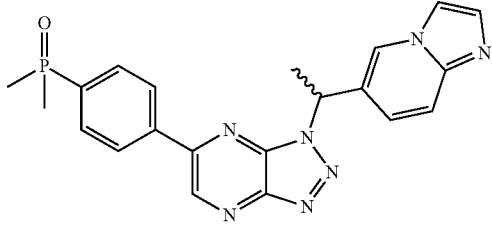

Compound 40 was prepared by methods analogous to those described for Example 6 by substituting imidazo[1,2-a]pyridin-6-ylmethanamine (16) with 1-(imidazo[1,2-a]pyridin-6-yl)ethan-1-amine (CAS #1270475-03-0) to afford (4-(1-(1-(imidazo[1,2-a]pyridin-6-yl)ethyl)-1H-[1,2,3]triazolo[4,5-b]pyrazin-6-yl)phenyl)dimethylphosphine oxide (40) as a tan solid: MS (m/z) MH+=418; $^1$H NMR (300 MHz, CDCl$_3$): δ 9.24 (s, 1H), 8.41 (br s, 1H), 8.25-8.15 (overlapping m, 2H), 8.00-7.90 (overlapping m, 2H), 7.70-7.55 (overlapping m, 3H), 7.41 (dd, J=9.5, 1.8 Hz, 1H), 6.41 (q, J=7.2 Hz, 1H), 2.33 (d, J=7.2 Hz, 1H), 1.82 (d, J=13.0 Hz, 6H).

Example 16

(4-(1-((2,3-Dihydrobenzofuran-5-yl)methyl)-1H-[1,2,3]triazolo[4,5-b]pyrazin-6-yl)phenyl)dimethylphosphine Oxide (41)

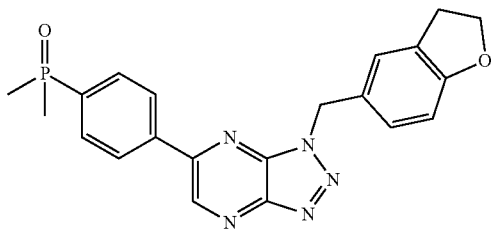

Compound 41 was prepared by methods analogous to those described for Example 6 by substituting imidazo[1,2-a]pyridin-6-ylmethanamine (16) (CAS #132213-03-7) with (2,3-dihydrobenzofuran-5-yl)methanamine (CAS #55745-74-9) to afford (4-(1-((2,3-dihydrobenzofuran-5-yl)methyl)-1H-[1,2,3]triazolo[4,5-b]pyrazin-6-yl)phenyl)dimethylphosphine oxide (41) as a light brown powder: MS (m/z) MH+=406; $^1$H NMR (300 MHz, DMSO-$d_6$): δ 9.54 (s, 1H), 8.43 (d, J=8.1 Hz, 2H), 8.05-7.98 (m, 2H), 7.37 (s, 1H), 7.29 (d, J=8.2 Hz, 1H), 6.75 (d, J=8.2 Hz, 1H), 5.94 (s, 2H), 4.49 (t, J=8.7 Hz, 2H), 3.13 (t, J=8.7 Hz, 2H), 1.74 (d, J=13.4 Hz, 6H).

Example 17

(4-(1-((3-Fluoroimidazo[1,2-a]pyridin-6-yl)methyl)-1H-[1,2,3]triazolo[4,5-b]pyrazin-6-yl)phenyl)dimethylphosphine Oxide (42)

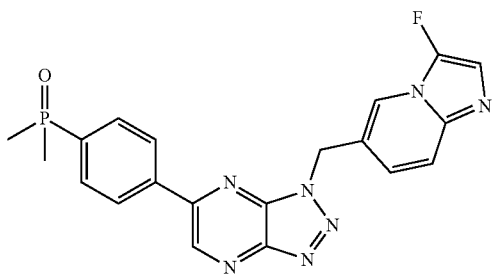

Compound 42 was prepared according to Scheme 23.

Scheme 23

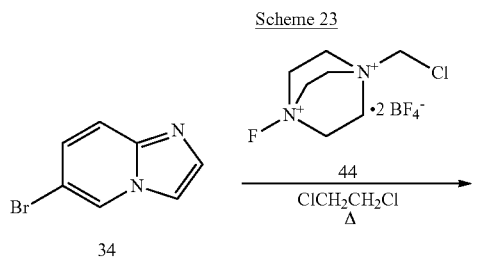

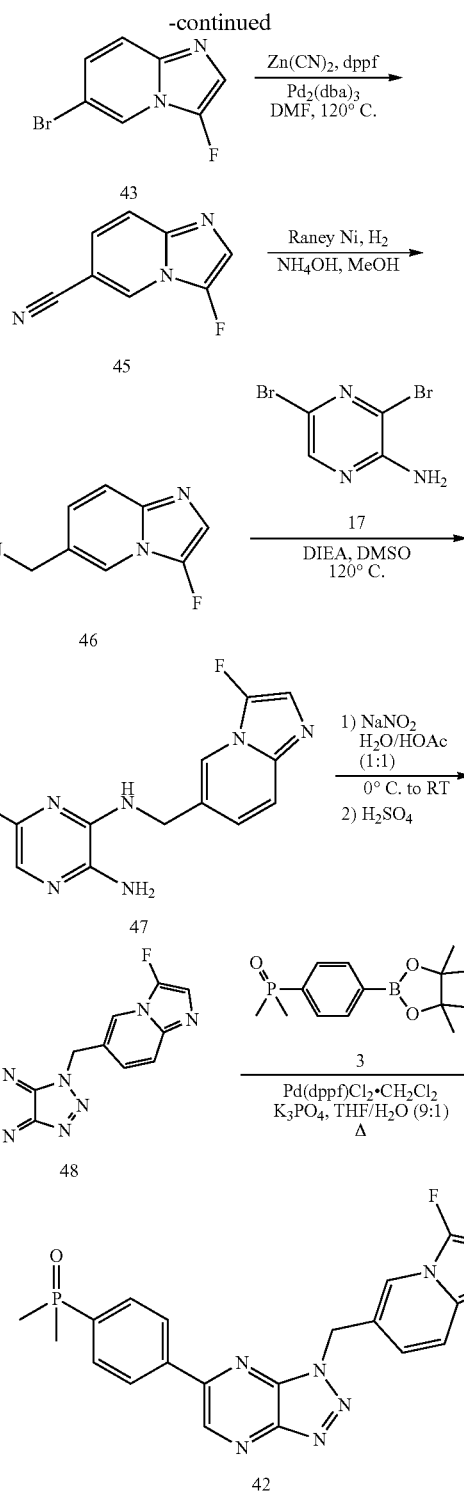

6-Bromo-3-fluoroimidazo[1,2-a]pyridine (43)

1-Chloromethyl-4-fluoro-1,4-diazonia-bicyclo[2.2.2]octane bis(tetrafluoroborate) (44) (4.2 g, 11.8 mmol) was added to a solution of 6-bromoimidazo[1,2-a]pyridine (34) (581 mg, 2.95 mmol) in anhydrous 1,2-dichloroethane (29.5 mL) while stirring at room temperature. The resulting suspension heated at reflux for 5 d, cooled to room temperature and concentrated in vacuo. The residue was purified by chromatography on silica gel eluting with a gradient of 0-10% EtOAc in hexanes to afford 360 mg of 6-bromo-3-fluoroimidazo[1,2-a]pyridine (43) as a light yellow solid. An analytical sample was recrystallized from heptane to provide an off-white powder: MS (m/z) MH$^+$=215; $^1$H NMR (300 MHz, DMSO-d$_6$): δ 8.68 (d, J=0.7 Hz, 1H), 7.52 (dd, J=9.6, 1.2 Hz, 1H), 7.42 (d, J=7.1 Hz, 1H), 7.35 (dd, J=9.7, 1.8 Hz, 1H); $^{13}$C NMR (75 MHz, DMSO-d$_6$): δ 142.3 (d, J=270.4 Hz), 136.2 (d, J=5.1 Hz), 127.4 (d, J=2.0 Hz), 122.5, 119.2, 112.5 (d, J=6.0 Hz), 107.2.

3-Fluoroimidazo[1,2-a]pyridine-6-carbonitrile (45)

Zinc cyanide (1.61 g, 13.7 mmol), 1,1'-bis(diphenylphosphino)ferrocene (162 mg, 0.29 mmol) and tris(dibenzylideneacetone) dipalladium(0) (134 mg, 0.15 mmol) were added to a stirred solution of 6-bromo-3-fluoroimidazo[1,2-a]pyridine (2.88 g, 13.4 mmol) in anhydrous DMF. The reaction mixture was degassed by 10 evacuation (until the solvent just boils)/N$_2$ blanketing cycles while stirring and then heated at 120° C. for 4 d. The reaction mixture was to room temperature, concentrated in vacuo and triturated several times with EtOAc. The EtOAc insoluble product was isolated by filtration and dried to provide 3.7 g of 3-fluoroimidazo[1,2-a]pyridine-6-carbonitrile (45) as a brown powder, which was used without further purification: MS (m/z) MH$^+$=162; $^1$H NMR (300 MHz, DMSO-d$_6$): δ 9.26 (s, 1H), 7.75-7.71 (m, 1H), 7.57 (d, J=6.9 Hz, 1H), 7.51 (dd, J=9.5, 1.7 Hz, 1H); $^{13}$C NMR (75 MHz, DMSO-d$_6$): δ 142.9 (d, J=273.9 Hz), 136.9 (d, J=4.5 Hz), 130.7, 124.5 (d, J=2.2 Hz), 118.7, 117.7, 113.3 (d, J=6.6 Hz), 98.3.

(3-Fluoroimidazo[1,2-a]pyridin-6-yl)methanamine (46)

3-Fluoroimidazo[1,2-a]-pyridine-6-carbonitrile (45) (3.7 g, 23.2 mmol) was added to a solution of concd. aq. NH$_4$OH (5.0 mL) in MeOH (200 mL). Active Raney Ni 2800 (6 mL of freshly shaken slurry in H$_2$O) was added and the reaction mixture placed under H$_2$ (1 atm) and rapidly stirred for 7 d. The reaction mixture was vacuum filtered through Celite 545 and the filtrate was concentrated in vacuo. The residue was purified by chromatography on silica gel eluting with a gradient of 1-10% MeOH (containing 2% concd. aq. NH$_4$OH) in CH$_2$Cl$_2$ to give 484 mg of (3-fluoroimidazo[1,2-a]pyridin-6-yl)methanamine (46) as a brown solid: MS (m/z) MH$^+$=166; $^1$H NMR (300 MHz, DMSO-d$_6$): δ 8.14 (s, 1H), 7.48-7.44 (m, 1H), 7.31 (d, J=7.2 Hz, 1H), 7.24 (dd, J=9.4, 1.6 Hz, 1H), 3.74 (d, J=0.9 Hz, 2H), 1.96 (br s, 2H); $^{13}$C NMR (75 MHz, DMSO-d$_6$): δ 142.3 (d, J=270.4 Hz), 136.2 (d, J=5.1 Hz), 127.4 (d, J=2.0 Hz), 122.5, 119.2, 112.5 (d, J=6.0 Hz), 107.2.

6-Bromo-N$^2$-((3-fluoroimidazo[1,2-a]pyridin-6-yl)methyl)pyrazine-2,3-diamine (47)

A stirred solution of (3-fluoroimidazo[1,2-a]pyridin-6-yl)methanamine (46) (468 mg, 2.8 mmol), 3,5-dibromopyrazin-2-amine (17) (2.2 g, 8.5 mmol) and N,N-diisopropylethylamine (2.5 mL, 14.4 mmol) in anhydrous DMSO (14.0 mL) was heated at 120° C. under N$_2$ for 4 d. The reaction mixture was cooled to room temperature and partitioned between water and EtOAc. The organic layer was washed with satd. aq. NaCl, dried (CaSO$_4$), filtered and concentrated in vacuo. The resulting residue was chromatographed on silica gel eluting with a gradient of 1-10% MeOH (containing 2% concd. aq. NH$_4$OH) in CH$_2$Cl$_2$ to provide 549 mg of 6-bromo-N$^2$-((3-fluoroimidazo-[1,2-a]pyridin-6-yl)methyl)pyrazine-2,3-diamine (47) as a yellowish-brown solid. An analytical sample was prepared by recrystallization from boiling EtOAc to give 47 as an off-white powder: MS (m/z) MH$^+$=337; $^1$H NMR (300 MHz, DMSO-d$_6$): δ 8.29 (s, 1H), 7.53 (dd, J=9.4, 1.0 Hz, 1H), 7.36 (d, J=7.1 Hz, 1H), 7.27-7.24 (m, 2H), 7.02 (t, J=5.3 Hz, 1H), 6.22 (s, 2H), 4.52 (d, J=5.2 Hz, 2H); $^{13}$C NMR (75 MHz, DMSO-d$_6$): δ 144.1, 143.7, 143.1, 140.5, 137.3, 137.2, 128.6, 125.8, 124.4, 122.1, 120.2, 117.9, 111.7, 111.6, 42.

6-Bromo-1-((3-fluoroimidazo[1,2-a]pyridin-6-yl)methyl)-1H-[1,2,3]triazolo[4,5-b]-pyrazine (48)

A cold solution of sodium nitrite (80 mg, 1.2 mmol) in water (1.0 mL) was added rapidly to a stirring solution of 6-bromo-N$^2$-((3-fluoroimidazo[1,2-a]pyridin-6-yl)methyl)pyrazine-2,3-diamine (47) (196 mg, 0.6 mmol) in 10 mL of acetic acid/H$_2$O (1:1) at 0° C. After 30 min, the reaction mixture was warmed to room temperature, stirred for 30 min, treated with concd. H$_2$SO$_4$ (3 drops) and stirred at room temperature for 18 h. The resulting solution was chilled, adjusted to approximately pH 10 with 20% aq. NaOH, and then extracted with EtOAc. The organic extract was dried (CaSO$_4$), filtered and concentrated in vacuo to afford 142 mg of 6-6romo-1-((3-fluoroimidazo[1,2-a]pyridin-6-yl)methyl)-1H-[1,2,3]triazolo[4,5-b]-pyrazine (48) as a yellow oil: MS (m/z) MH$^+$=348.

(4-(1-((3-Fluoroimidazo[1,2-a]pyridin-6-yl)methyl)-1H-[1,2,3]triazolo[4,5-b]pyrazin-6-yl)phenyl)dimethylphosphine Oxide (42)

A mixture of 6-bromo-1-((3-fluoroimidazo[1,2-a]pyridin-6-yl)methyl)-1H-[1,2,3]triazolo[4,5-b]pyrazine (48) (60 mg, 0.2 mmol), dimethyl(4-(4,4,5,5-tetramethyl-1,3,2-dioxaborolan-2-yl)phenyl)phosphine oxide (3) (52 mg, 0.2 mmol), tripotassium phosphate (181 mg, 0.9 mmol), and [1,1'-bis(diphenylphosphino)ferrocene]-dichloropalladium (II) complex with CH$_2$Cl$_2$ (28 mg, 0.03 mmol) in 10 mL of a mixture of H$_2$O/THF (9:1) was degassed and then heated at reflux under N$_2$ for 30 min. The reaction mixture was cooled to room temperature, concentrated in vacuo and chromatographed on silica gel eluting with 0-10% MeOH in CH$_2$Cl$_2$ to provide 41 mg of yellow oil. This material was crystallized from a mixture of MeOH/EtOAc/heptane to yield 34 mg of (4-(1-((3-fluoroimidazo[1,2-a]pyridin-6-yl)methyl)-1H-[1,2,3]triazolo[4,5-b]pyrazin-6-yl)phenyl)-dimethylphosphine oxide (42) as an off-white powder: MS (m/z) MH$^+$=422; $^1$H NMR (300 MHz, DMSO-d$_6$): δ 9.57 (s, 1H), 8.69 (s, 1H), 8.45 (dd, J=8.4, 2.0 Hz, 2H), 8.03-7.97 (m, 2H), 7.53 (d, J=9.5 Hz, 1H), 7.39 (d, J=7.1 Hz, 1H), 7.35-7.32 (m, 1H), 6.12 (s, 2H), 1.73 (d, J=13.4 Hz, 6H).

Example 18

Dimethyl(1-(quinolin-6-ylmethyl)-1H-[1,2,3]triazolo[4,5-b]pyrazin-6-yl)phosphine Oxide (49)

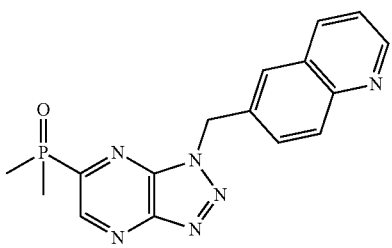

49

Compound 49 was prepared by a procedure analogous to the one described for the first step of Example 5 by substituting 4-bromo-3-fluoroaniline (13) with 6-((6-bromo-1H-[1,2,3]triazolo[4,5-b]pyrazin-1-yl)methyl)quinoline (2) to afford compound 49 as an off-white powder: MS (m/z) MH$^+$=339; $^1$H NMR (300 MHz, DMSO-d$_6$): δ 9.28 (s, 1H), 8.92 (s, 1H), 8.38 (d, J=7.9 Hz, 1H), 8.10 (s, 1H), 8.04 (d, J=8.6 Hz, 1H), 7.88 (d, J=8.9 Hz, 1H), 7.57-7.54 (m, 1H), 6.27 (s, 2H), 1.84 (d, J=13.9 Hz, 6H).

Example 19

Dimethyl(4-(1-(1-(quinolin-6-yl)ethyl)-1H-[1,2,3]triazolo[4,5-b]pyrazin-6-yl)phenyl)phosphine Oxide (50)

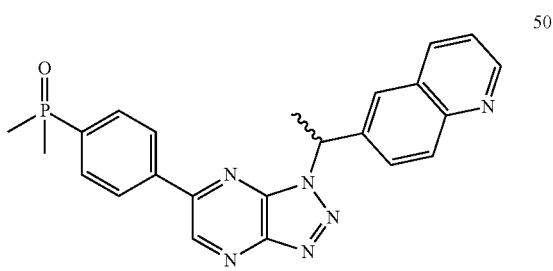 [SMILES: CC(c1ccc2ncccc2c1)n1nnc2ncc(-c3ccc(P(C)(C)=O)cc3)nc21]

50

Compound 50 was prepared by methods analogous to those described for Example 6 by substituting imidazo[1,2-a]pyridin-6-ylmethanamine (16) with 1-(quinolin-6-yl)ethan-1-amine (CAS #151506-20-6) to furnish dimethyl(4-(1-(1-(quinolin-6-yl)ethyl)-1H-[1,2,3]triazolo[4,5-b]pyrazin-6-yl)phenyl)phosphine oxide (50) as a beige solid: MS (m/z) MH$^+$=429; $^1$H NMR (300 MHz, CDCl$_3$): δ 9.22 (s, 1H), 8.92 (dd, J=4.3, 1.7 Hz, 1H), 8.21 (dd, J=8.5, 2.3 Hz, 1H), 8.17 (dd, 8.5, 0.9 Hz, 1H), 8.10 (d, J=8.8 Hz, 1H), 8.00-7.88 (m, 4H), 7.43 (dd, J=8.3, 4.2 Hz, 1H), 6.58 (q, J=7.2 Hz, 1H), 2.39 (d, J=7.2 Hz, 3H), 1.81 (d, J=13.0 Hz, 6H).

Example 20

(4-(1-((6-Fluoro-2-methyl-2H-indazol-5-yl)methyl)-1H-[1,2,3]triazolo[4,5-b]pyrazin-6-yl)phenyl)dimethylphosphine Oxide (51)

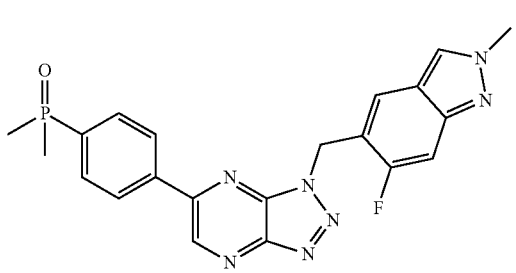

The synthesis of the required starting material (6-fluoro-2-methyl-2H-indazol-5-yl)methanamine (52) is shown below in Scheme 24.

Scheme 24

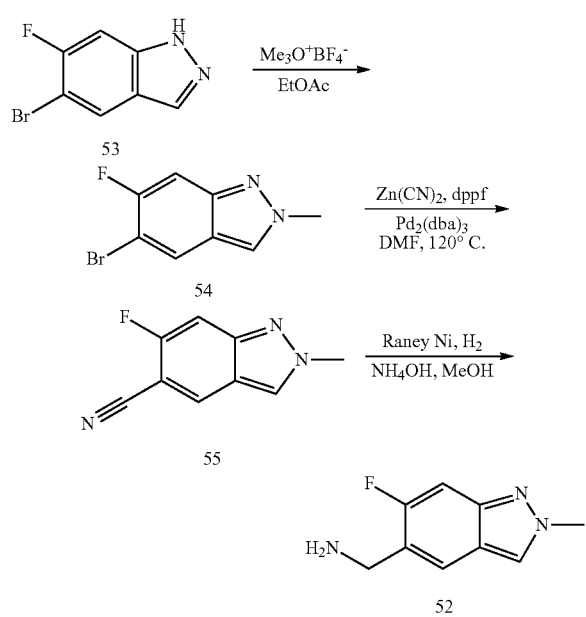

5-Bromo-6-fluoro-2-methyl-2H-indazole (54)

Trimethyloxonium tetrafluoroborate (1.0 g, 6.5 mmol) was added at room temperature to a clear brown solution of 5-bromo-6-fluoro-1H-indazole (1.2 g, 5.4 mmol) in EtOAc (54.0 mL) while stirring under $N_2$. The reaction, which appeared as a suspension after 30 min, was allowed to continue for 18 h. Subsequently, the reaction mixture was partitioned between 5% aq. $NaHSO_3$ and additional EtOAc. The organic extract was washed with sat. aq. NaCl, dried ($CaSO_4$), filtered, and chromatographed on silica gel eluting with a gradient of 0-100% EtOAc in hexanes to provide 742 mg of 5-bromo-6-fluoro-2-methyl-2H-indazole (54) as an orange solid: MS (m/z) $MH^+=229$.

6-Fluoro-2-methyl-2H-indazole-5-carbonitrile (55)

Zinc cyanide (384 mg, 3.3 mmol), 1,1'-ferrocenediyl-bis(diphenylphosphine) (37 mg, 0.07 mmol), and tris(dibenzylideneacetone) dipalladium(0) (30 mg, 0.03 mmol) were added to a stirred solution of 5-bromo-6-fluoro-2-methyl-2H-indazole (54) (745 mg, 3.3 mmol) in anhydrous DMF (10.8 mL). The reaction mixture was degassed through 10 evacuation (until the solvent just boils)/$N_2$ purging cycles and subsequently heated at 120° C. while stirring under $N_2$. After 2 d, additional zinc cyanide (192 mg, 1.6 mmol) was added and the reaction was stirred at 120° C. for 4 d. The reaction mixture cooled to room temperature and evaporated to dryness. The residue was purified by chromatography on silica gel eluting with a gradient of 20-100% EtOAc in hexanes to furnish 701 mg of 6-fluoro-2-methyl-2H-indazole-5-carbonitrile (55) as a light brown solid: MS (m/z) $MH^+=176$.

(6-Fluoro-2-methyl-2H-indazol-5-yl)methanamine (52)

Raney Ni 2800 (6 mL of freshly shaken slurry in water) was added to a solution of 6-fluoro-2-methyl-2H-indazole-5-carbonitrile (55) (701 mg, 3.3 mmol) in concd. aq. $NH_4OH$ (30 mL) and MeOH (130 mL) while stirring at room temperature under $N_2$. The reaction mixture was then sparged with $H_2$ at atmospheric pressure, stirred at room temperature for 30 min, filtered through a pad of Celite 545. The clear colorless filtrate was concentrated in vacuo and the residue was purified by chromatography on silica gel eluting with a gradient of 1-10% MeOH (containing 2% concd. aq. $NH_4OH$) in $CH_2Cl_2$ to furnish 340 mg of (6-fluoro-2-methyl-2H-indazol-5-yl)methanamine (52) as an off-white solid: MS (m/z) $MH^+=180$; $^1H$ NMR (300 MHz, DMSO-$d_6$): δ 8.32 (s, 1H), 7.72 (d, J=7.6 Hz, 1H), 7.26 (d, J=11.8 Hz, 1H), 4.13 (s, 3H), 3.78 (s, 2H), 1.83 (br s, 2H); $^{13}C$ NMR (75 MHz, DMSO-$d_6$): δ 160.3 (d, J=241.6 Hz), 147.4 (d, J=13.5 Hz), 127.8 (d, J=20.7 Hz), 125.2, 119.9 (d, J=7.1 Hz), 119.2, 100.1 (d, J=24.2 Hz), 40.6, 40.4.

(4-(1-((6-Fluoro-2-methyl-2H-indazol-5-yl)methyl)-1H-[1,2,3]triazolo[4,5-b]pyrazin-6-yl)phenyl)dimethylphosphine Oxide (51)

Compound 51 was prepared by methods analogous to those described for Example 6 by substituting imidazo[1,2-a]pyridin-6-ylmethanamine (16) with (6-fluoro-2-methyl-2H-indazol-5-yl)methanamine (52) to afford (4-(1-((6-fluoro-2-methyl-2H-indazol-5-yl)methyl)-1H-[1,2,3]triazolo[4,5-b]pyrazin-6-yl)phenyl)dimethylphosphine oxide (51) as an off-white solid: MS (m/z) $MH^+=436$; $^1H$ NMR (300 MHz, DMSO-$d_6$): δ 9.55 (s, 1H), 8.44 (s, 1H), 8.41 (dd, J=8.4, 2.1 Hz, 2H), 8.03-7.97 (m, 3H), 7.40 (d, J=11.5 Hz, 1H), 6.12 (s, 2H), 4.14 (s, 3H), 1.73 (d, J=13.4 Hz, 6H).

Example 21

(4-(1-((6-Fluoro-2-methyl-2H-indazol-5-yl)methyl)-1H-[1,2,3]triazolo[4,5-b]pyrazin-6-yl)phenyl)dimethylphosphine oxide (56)

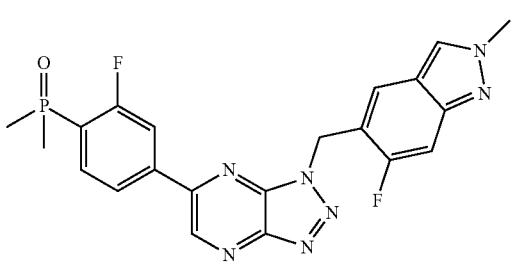

Compound 56 was prepared by methods analogous to those described for Example 6 by substituting imidazo[1,2-a]pyridin-6-ylmethanamine (16) with (6-fluoro-2-methyl-2H-indazol-5-yl)methanamine (52) and dimethyl(4-(4,4,5,5-tetramethyl-1,3,2-dioxaborolan-2-yl)phenyl)phosphine oxide (3) with (2-fluoro-4-(4,4,5,5-tetramethyl-1,3,2-dioxaborolan-2-yl)phenyl)dimethylphosphine oxide to furnish (2-fluoro-4-(1-((6-fluoro-2-methyl-2H-indazol-5-yl)methyl)-1H-[1,2,3]triazolo[4,5-b]pyrazin-6-yl)phenyl)-dimethylphosphine oxide (56) as a light brown powder: MS (m/z) MH$^+$454; $^1$H NMR (300 MHz, DMSO-d$_6$): δ 9.58 (s, 1H), 8.44 (s, 1H), 8.31 (d, J=8.0 Hz, 1H), 8.25-8.20 (m, 1H), 8.02-7.93 (m, 2H), 7.40 (d, J=11.6 Hz, 1H), 6.13 (s, 2H), 4.14 (s, 3H), 1.79 (d, J=13.7 Hz, 6H).

Example 22

(2-Fluoro-4-(1-((2-methyl-2H-indazol-5-yl)methyl)-1H-[1,2,3]triazolo[4,5-b]pyrazin-6-yl)phenyl)dimethylphosphine Oxide (57)

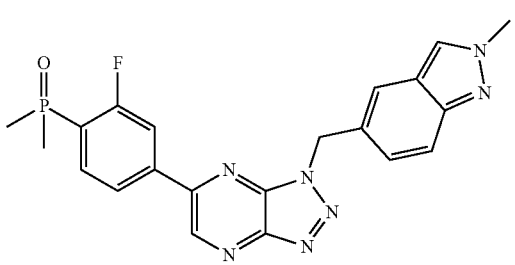

Compound 5 was prepared by methods analogous to those described for Example 6 by substituting imidazo[1,2-a]pyridin-6-ylmethanamine (16) with (2-methyl-2-indazol-5-yl)methanamine and dimethyl(4-(4,4,5,5-tetramethyl-1,3,2-dioxaborolan-2-yl)phenyl)phosphine oxide (3) with (2-fluoro-4-(4,4,5,5-tetramethyl-1,3,2-dioxaborolan-2-yl)phenyl)dimethylphosphine oxide to furnish (2-fluoro-4-(1-((2-methyl-2H-indazol-5-yl)methyl)-1H-[1,2,3]triazolo[4,5-b]pyrazin-6-yl)phenyl)dimethylphosphine oxide (57) as a yellow powder: MS (m/z) MH$^+$436; $^1$H NMR (300 MHz, DMSO-d$_6$): δ 9.57 (s, 1H), 8.35 (s, 1H), 8.34-8.30 (m, 1H), 8.26 (ddd, J=1.3, 4.1, 11.3 Hz, 1H), 8.05-7.93 (m, 1H), 7.86 (s, 1H), 7.58 (d, J=8.9 Hz, 1H), 7.34 (dd, J=1.65, 8.9 Hz, 1H), 6.10 (s, 2H), 4.14 (s, 3H), 1.79 (d, J=13.7 Hz, 6H).

Biochemical Assay

Reagents:

Reaction Buffer: 20 mM Hepes (pH 7.5), 10 mM MgCl$_2$, 1 mM EGTA, 0.02%, Brij35, 0.02 mg/mL BSA, 0.1 mM Na$_3$VO$_4$, 2 mM DTT and 1% DMSO.

Required cofactors were added individually to each kinase reaction.

Compound Handling:

The testing compounds were dissolved in 100% DMSO to specific concentration. The serial dilution was conducted by Integra Viaflo Assist in DMSO.

Reaction Procedure:

1. Prepare substrate in freshly prepared Reaction Buffer.
2. Deliver any required cofactors to the substrate solution above.
3. Deliver kinase into the substrate solution and gently mix.
4. Deliver compounds in 100% DMSO into the kinase reaction mixture by Acoustic technology (Echo550; nanoliter range), incubate for 20 min at room temp.
5. Deliver $^{33}$P-ATP (Specific activity 10 μCi/μL) into the reaction mixture to initiate the reaction.
6. Incubate for 2 hours at room temperature.
7. Detect radioactivity by filter-binding method.
8. Kinase activity data were expressed as the percent remaining kinase activity in test samples compared to vehicle (DMSO) reactions. IC$_{50}$ values and curve fits were obtained using Prism (GraphPad Software) (Table 1).

TABLE 1

Results of biochemical assay of the exemplary compounds.

| Ex | Compd | Method[a] | Structure | Name | IC$_{50}$[b] |
|---|---|---|---|---|---|
| 1 | 1 | A | 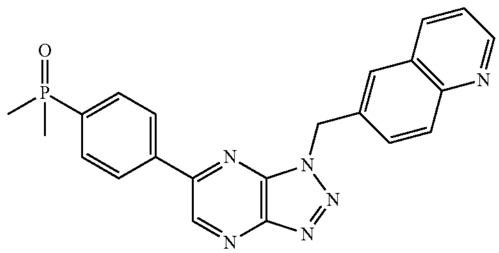 [SMILES: CP(C)(=O)c1ccc(-c2cnc3nnn(Cc4ccc5ncccc5c4)c3n2)cc1] | Dimethyl(4-(1-(quinolin-6-ylmethyl)-1H-[1,2,3]triazolo[4,5-b]pyrazin-6-yl)phenyl) phosphine oxide | ++++ |
| 2 | 4 | A | 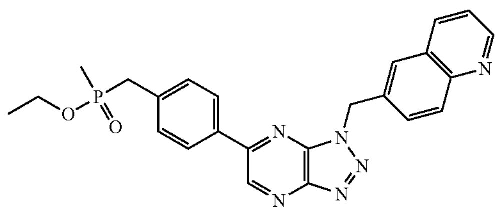 [SMILES: CCOP(C)(=O)Cc1ccc(-c2cnc3nnn(Cc4ccc5ncccc5c4)c3n2)cc1] | Ethyl methyl(4-(1-(quinolin-6-ylmethyl)-1H-[1,2,3]triazolo[4,5-b]pyrazin-6-yl)benzyl) phosphinate | ++++ |
| 3 | 5 | A | 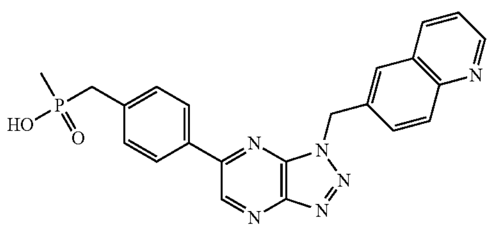 [SMILES: CP(=O)(O)Cc1ccc(-c2cnc3nnn(Cc4ccc5ncccc5c4)c3n2)cc1] | Methyl(4-(1-(quinolin-6-ylmethyl)-1H-[1,2,3]triazolo[4,5-b]pyrazin-6-yl)benzyl) phosphinic acid | ++++ |
| 4 | 7 | A | 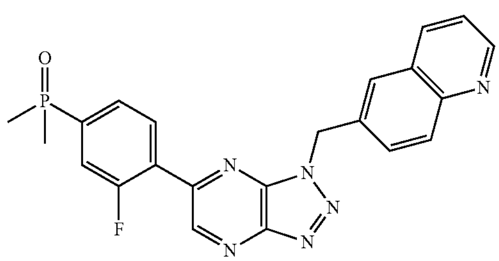 [SMILES: CP(C)(=O)c1ccc(-c2cnc3nnn(Cc4ccc5ncccc5c4)c3n2)c(F)c1] | (3-Fluoro-4-(1-(quinolin-6-ylmethyl)-1H-[1,2,3]triazolo[4,5-b]pyrazin-6-yl)phenyl)dimethylphosphine oxide | +++ |
| 5 | 10 | B | 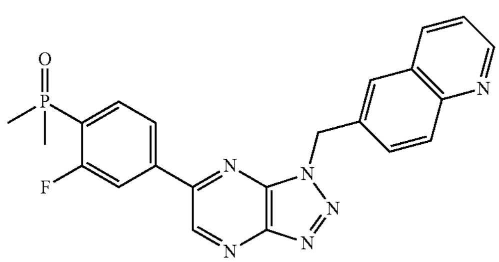 [SMILES: CP(C)(=O)c1ccc(-c2cnc3nnn(Cc4ccc5ncccc5c4)c3n2)cc1F] | (2-Fluoro-4-(1-(quinolin-6-ylmethyl)-1H-[1,2,3]triazolo[4,5-b]pyrazin-6-yl)phenyl)dimethylphosphine oxide | ++++ |
| 6 | 15 | C | 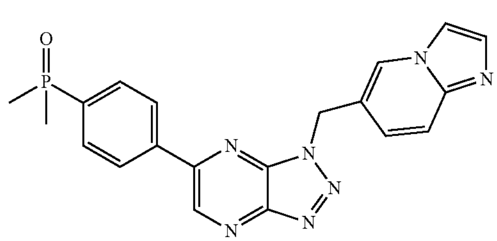 [SMILES: CP(C)(=O)c1ccc(-c2cnc3nnn(Cc4ccc5nccn5c4)c3n2)cc1] | (4-(1-(Imidazo[1,2-a]pyridin-6-ylmethyl)-1H-[1,2,3]triazolo[4,5-b]pyrazin-6-yl)phenyl)dimethylphosphine oxide | ++++ |

TABLE 1-continued

Results of biochemical assay of the exemplary compounds.

| Ex | Compd | Method[a] | Structure | Name | IC$_{50}$[b] |
|---|---|---|---|---|---|
| 7 | 20 | C | 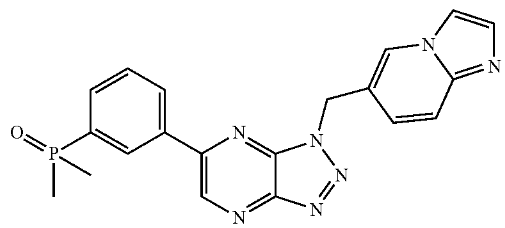 [SMILES: CP(C)(=O)c1cccc(-c2cnc3nnn(Cc4ccc5nccn5c4)c3n2)c1] | (3-(1-(Imidazo[1,2-a]pyridin-6-ylmethyl)-1H-[1,2,3]triazolo[4,5-b]pyrazin-6-yl)phenyl)dimethylphosphine oxide | +++ |
| 8 | 24 | A | 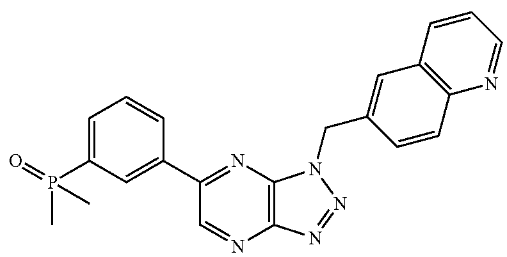 [SMILES: CP(C)(=O)c1cccc(-c2cnc3nnn(Cc4ccc5ncccc5c4)c3n2)c1] | Dimethyl(3-(1-(quinolin-6-ylmethyl)-1H-[1,2,3]triazolo[4,5-b]pyrazin-6-yl)phenyl)phosphine oxide | +++ |
| 9 | 25 | D | 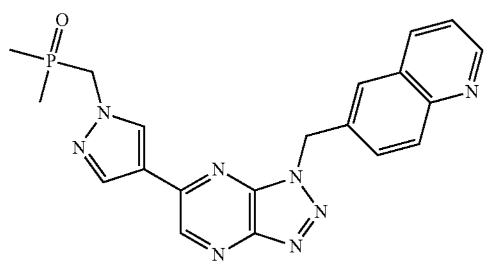 [SMILES: CP(C)(=O)Cn1cc(-c2cnc3nnn(Cc4ccc5ncccc5c4)c3n2)cn1] | Dimethyl((4-(1-(quinolin-6-ylmethyl)-1H-[1,2,3]triazolo[4,5-b]pyrazin-6-yl)-1H-pyrazol-1-yl)methyl)phosphine oxide | ++ |
| 10 | 29 | D | 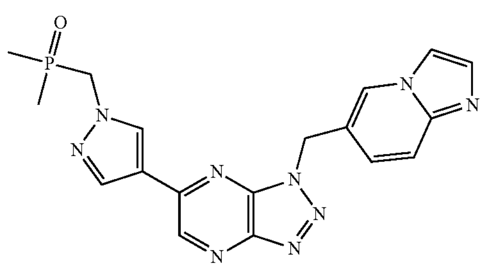 [SMILES: CP(C)(=O)Cn1cc(-c2cnc3nnn(Cc4ccc5nccn5c4)c3n2)cn1] | ((4-(1-(Imidazo[1,2-a]pyridin-6-ylmethyl)-1H-[1,2,3]triazolo[4,5-b]pyrazin-6-yl)-1H-pyrazol-1-yl)methyl)dimethylphosphine oxide | ++ |
| 11 | 30 | E | 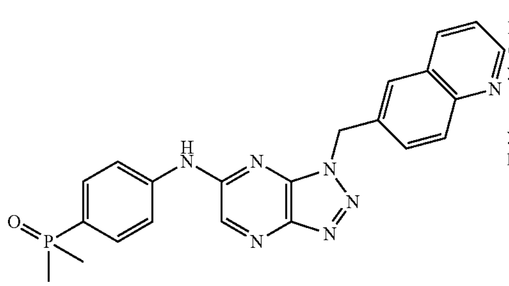 [SMILES: CP(C)(=O)c1ccc(Nc2cnc3nnn(Cc4ccc5ncccc5c4)c3n2)cc1] | Dimethyl(4-((1-(quinolin-6-ylmethyl)-1H-[1,2,3]triazolo[4,5-b]pyrazin-6-yl)amino)phenyl)phosphine oxide | ++++ |

TABLE 1-continued

Results of biochemical assay of the exemplary compounds.

| Ex | Compd | Method[a] | Structure | Name | IC$_{50}$[b] |
|---|---|---|---|---|---|
| 12 | 32 | F | 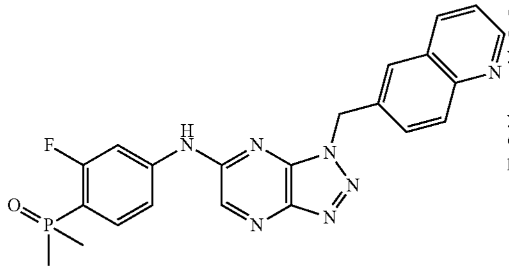 [SMILES: CP(C)(=O)c1ccc(Nc2cnc3nnn(Cc4ccc5ncccc5c4)c3n2)cc1F] | (2-Fluoro-4-((1-(quinolin-6-ylmethyl)-1H-[1,2,3]triazolo[4,5-b]pyrazin-6-yl)amino)phenyl)dimethylphosphine oxide | ++++ |
| 13 | 33 | G | 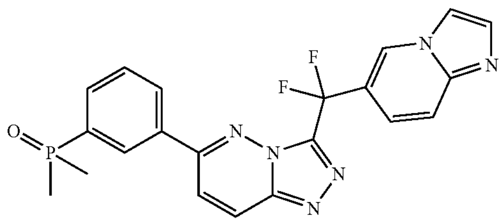 [SMILES: CP(C)(=O)c1cccc(-c2ccc3nnc(C(F)(F)c4ccc5nccn5c4)n3n2)c1] | (3-(3-(Difluoro(imidazo[1,2-a]pyridin-6-yl)methyl)-[1,2,4]triazolo[4,3-b]pyridazin-6-yl)phenyl)dimethylphosphine oxide | ++ |
| 14 | 39 | A | 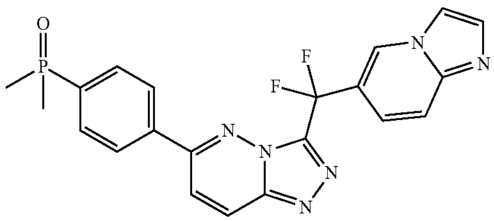 [SMILES: CP(C)(=O)c1ccc(-c2ccc3nnc(C(F)(F)c4ccc5nccn5c4)n3n2)cc1] | (4-(3-(Difluoro(imidazo[1,2-a]pyridin-6-yl)methyl)-[1,2,4]triazolo[4,3-b]pyridazin-6-yl)phenyl)dimethyl phosphine oxide | + |
| 15 | 40 | C | 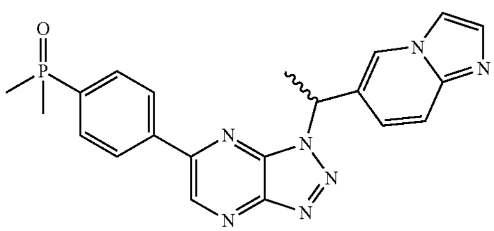 [SMILES: CC(c1ccc2nccn2c1)n1nnc2ncc(-c3ccc(P(C)(C)=O)cc3)nc21] | (4-(1-(1-(Imidazo[1,2-a]pyridin-6-yl)ethyl)-1H-[1,2,3]triazolo[4,5-b]pyrazin-6-yl)phenyl)dimethylphosphine oxide | ++++ |
| 16 | 41 | A | 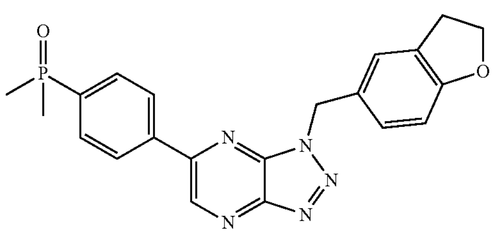 [SMILES: CP(C)(=O)c1ccc(-c2cnc3nnn(Cc4ccc5c(c4)CCO5)c3n2)cc1] | (4-(1-((2,3-Dihydrobenzofuran-5-yl)methyl)-1H-[1,2,3]triazolo[4,5-b]pyrazin-6-yl)phenyl)dimethylphosphine oxide | +++ |
| 17 | 42 | C | 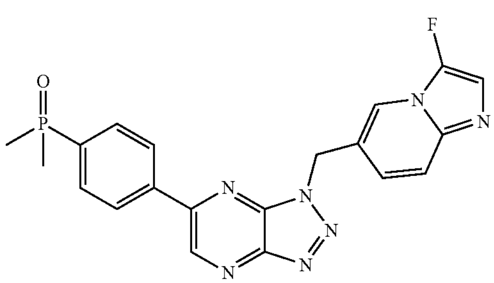 [SMILES: CP(C)(=O)c1ccc(-c2cnc3nnn(Cc4ccc5ncc(F)n5c4)c3n2)cc1] | (4-(1-((3-Fluoroimidazo[1,2-a]pyridin-6-yl)methyl)-1H-[1,2,3]triazolo[4,5-b]pyrazin-6-yl)phenyl)dimethylphosphine oxide | ++ |

TABLE 1-continued

Results of biochemical assay of the exemplary compounds.

| Ex | Compd | Method[a] | Structure | Name | IC$_{50}$[b] |
|---|---|---|---|---|---|
| 18 | 49 | B | 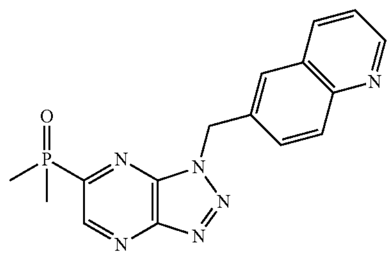 [SMILES: CP(C)(=O)c1cnc2nnn(Cc3ccc4ncccc4c3)c2n1] | Dimethyl(1-(quinolin-6-ylmethyl)-1H-[1,2,3]triazolo[4,5-b]pyrazin-6-yl)phosphine oxide | + |
| 19 | 50 | C | 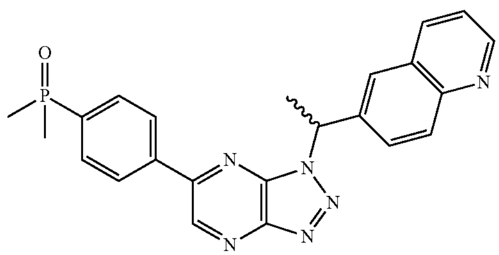 [SMILES: CC(c1ccc2ncccc2c1)n1nnc2ncc(-c3ccc(P(C)(C)=O)cc3)nc21] | Dimethyl(4-(1-(1-(quinolin-6-yl)ethyl)-1H-[1,2,3]triazolo[4,5-b]pyrazin-6-yl)phenyl)phosphine oxide | ++++ |
| 20 | 51 | C | 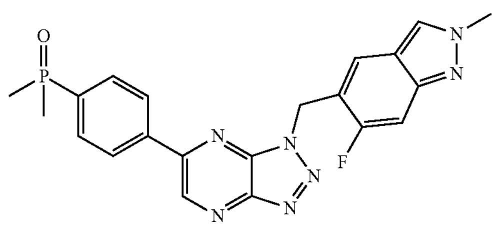 | (4-(1-((6-Fluoro-2-methyl-2H-indazol-5-yl)methyl)-1H-[1,2,3]triazolo[4,5-b]pyrazin-6-yl)phenyl)dimethylphosphine oxide | ++++ |
| 21 | 56 | C | 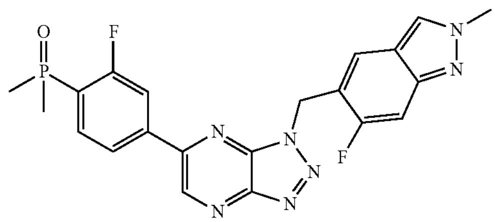 | (2-Fluoro-4-(1-((6-fluoro-2-methyl-2H-indazol-5-yl)methyl)-1H-[1,2,3]triazolo[4,5-b]pyrazin-6-yl)phenyl)dimethylphosphine oxide | ++++ |
| 22 | 57 | C | 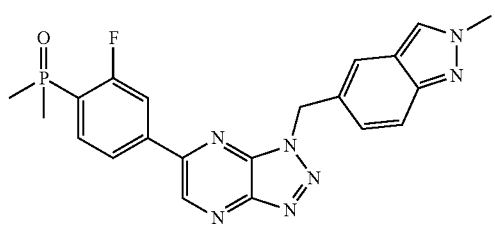 | (2-Fluoro-4-(1-((2-methyl-2H-indazol-5-yl)methyl)-1H-[1,2,3]triazolo[4,5-b]pyrazin-6-yl)phenyl)dimethylphosphine oxide | ++++ |

[a]The methods are described in the following corresponding examples: A (Example 1), B (Example 5), C (Example 6), D (Example 9), E (Example 11), F (Example 12), G (Example 13) and H (Example 20).

[b]IC$_{50}$ ranges are defined as: < 10 nM = ++++; 11-20 nM = +++; 21-100 nM = ++; 1,000-6,000 nM = +.

The foregoing embodiments and examples are provided for illustration only and are not intended to limit the scope of the invention. Various changes and modifications to the disclosed embodiments will be apparent to those skilled in the art based on the present disclosure, and such changes and modifications may be made without departure from the spirit and scope of the present invention. All patent or non-patent references cited are incorporated herein by reference in their entireties without admission of them as prior art.

What is claimed is:

1. A compound of formula (I):

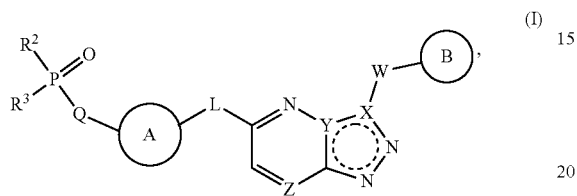

or a pharmaceutically acceptable salt, solvate, or prodrug thereof, wherein:

A is absent, arylene or heteroarylene, each optionally substituted by one to four substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, hydroxy, $C_1$-$C_6$ acyl, cyano, nitro, and $NR^cR^d$;

L is absent, O, S, $NR^1$, C(O), or $C(R^L)_2$, wherein $R^L$ at each occurrence is independently hydrogen, halogen, or $C_1$-$C_4$ alkyl;

Q is absent or $C(R^Q)_2$, wherein $R^Q$ at each occurrence is independently hydrogen, halogen, $C_1$-$C_4$ alkyl, $C_1$-$C_4$ haloalkyl, $C_1$-$C_4$ alkoxy, or $C_1$-$C_4$ haloalkoxy;

X and Y are each C or N;

Z is $CR^Z$ or N, wherein $R^Z$ is hydrogen, halogen, $C_1$-$C_4$ alkyl, $C_1$-$C_4$ haloalkyl, $C_1$-$C_4$ alkoxy, or $C_1$-$C_4$ haloalkoxy;

when X is C and Y is N, then W is O, $NR^1$, S, or $CR^5R^6$;

when X is N, then W is $CR^5R^6$, provided that at least one of X and Y is N, $R^1$ is H or $C_1$-$C_6$ alkyl;

$R^2$ and $R^3$ are each independently alkyl, aryl, cycloalkyl, heteroaryl, heterocyclyl, —$OR^4$, —$NR^7R^8$, or —$OCH_2(C=O)OR^9$, wherein said alkyl, aryl, cycloalkyl, heteroaryl, or heterocyclyl is each optionally substituted by one to five substituents independently selected from the group consisting of $C_1$-$C_6$ alkyl, $C_2$-$C_6$ alkenyl, $C_2$-$C_6$ alkynyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —$C(O)OR^9$, —$C(O)R^{10}$, —$NR^aR^b$, and —$C(O)NR^cR^d$; or alternatively $R^2$ and $R^3$ together with the phosphorus atom to which they are attached form a 4- to 8-membered ring optionally substituted with one to five substituents independently selected from the group consisting of $C_1$-$C_6$ alkyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —$C(O)OR^9$, —$C(O)R^{10}$, —$NR^aR^b$, —$C(O)NR^cR^d$, and oxo;

$R^4$ at each occurrence is independently hydrogen, alkyl, cycloalkyl, aryl, heteroaryl, heterocyclyl, or arylalkyl, each except hydrogen optionally substituted;

$R^5$ and $R^6$ are each independently selected from H, halogen, $C_1$-$C_6$ alkyl, and $C_1$-$C_6$ alkoxy; or $R^5$ and $R^6$ together form oxo (=O) or with the carbon atom to which they are attached form a 3- to 6-membered ring optionally substituted by one to five substituents independently selected from the group consisting of halogen, $C_1$-$C_6$ alkyl, and $C_1$-$C_6$ alkoxy;

$R^7$ and $R^8$ are independently selected from hydrogen, $C_1$-$C_6$ alkyl, $C_3$-$C_6$ cycloalkyl, $C_6$-$C_{10}$ aryl, 5- to 10-membered heteroaryl, and 5- to 10-membered heterocyclyl; or alternatively, $R^7$ and $R^8$ together with the nitrogen atom to which they are attached, form a 4- to 6-membered ring, wherein said 4- to 6-membered ring optionally may contain one to five substituents independently selected from the group consisting of halogen, $C_1$-$C_6$ alkyl, $C_1$-$C_6$ haloalkyl, $C_6$-$C_{10}$ aryl, and —$OR^9$;

B is aryl, heteroaryl, cycloalkyl, or heterocyclyl, each optionally substituted with one or more, sometimes preferably one to five, sometimes more preferably one to three, substituents independently selected from the group consisting of halogen, $C_1$-$C_6$ alkyl, $C_1$-$C_6$ haloalkyl, $C_2$-$C_6$ alkenyl, $C_3$-$C_6$ cycloalkyl, $C_6$-$C_{10}$ aryl, 5- to 10-membered heteroaryl, 3- to 10-membered heterocyclyl, CN, $P(=O)(R^9)_2$, $P(=O)(OR^9)_2$, —$C(O)R^{10}$, —$CO_2R^9$, —$OR^9$, —$SR^9$, —$NR^aR^b$, —$CONR^aR^b$, —$NR^{12}C(O)R^{10}$, —$NR^{12}SO_2R^{11}$, —$NR^{12}SO_2NR^aR^b$, —$SO_2R^{11}$, and —$SO_2NR^aR^b$;

$R^9$ at each occurrence is independently hydrogen, $C_1$-$C_6$ alkyl, or $C_6$-$C_{10}$ aryl;

$R^{10}$ at each occurrence is independently hydrogen, $C_1$-$C_6$ alkyl, $C_1$-$C_6$ haloalkyl, $C_3$-$C_6$ cycloalkyl, $C_6$-$C_{10}$ aryl, or 5- to 10-membered heteroaryl, each except hydrogen optionally substituted;

$R^{11}$ at each occurrence is independently selected from the group consisting of $C_1$-$C_6$ alkyl, $C_3$-$C_6$ cycloalkyl, $C_6$-$C_{10}$ aryl, and 5- to 10-membered heteroaryl, each optionally substituted;

$R^{12}$ each occurrence is independently hydrogen, $C_1$-$C_6$ alkyl, or $C_3$-$C_6$ cycloalkyl;

wherein, unless specifically defined, cycloalkyl and heterocyclyl may optionally be fused onto an aromatic ring and may optionally be substituted with one to five substituents independently selected from the group consisting of halogen, cyano, nitro, —$OR^{13}$, —$SR^{13}$, $C_1$-$C_6$ alkyl, $C_6$-$C_{10}$ aryl, —$NR^aR^b$, and —$C(O)OR^{14}$;

wherein, unless specifically defined, any said aryl and heteroaryl may optionally be substituted with one to five substituents independently selected from halogen, cyano, nitro, —$OR^{13}$, —$SR^{13}$, $C_1$-$C_6$ alkyl, $C_1$-$C_6$ haloalkyl, $C_6$-$C_{10}$ aryl, —$C(O)OR^{14}$, —$NR^aR^b$, and —$C(O)NR^cR^d$;

$R^{13}$ at each occurrence is independently hydrogen, $C_1$-$C_6$ alkyl, or $C_1$-$C_6$ haloalkyl;

$R^{14}$ at each occurrence is independently hydrogen or $C_1$-$C_6$ alkyl;

$R^a$ and $R^b$ are independently selected from hydrogen, $C_1$-$C_6$ alkyl, $C_3$-$C_6$ cycloalkyl, $C_6$-$C_{10}$ aryl, 5- to 10-membered heteroaryl, and benzyl; and $R^c$ and $R^d$ are independently hydrogen or $C_1$-$C_6$ alkyl.

2. The compound of claim 1, wherein X is N, Y is C, and Z is N, having a structure of formula (II):

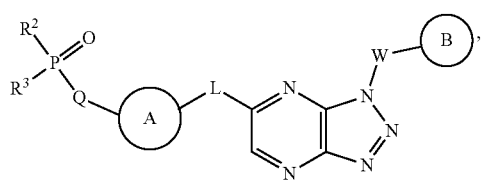
(II)

or a pharmaceutically acceptable salt, solvate, or prodrug thereof.

3. The compound of claim 1, wherein X is C, Y is N, and Z is CH, having a structure of formula (III):

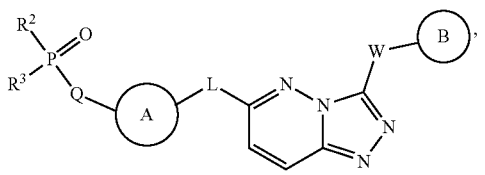
(III)

or a pharmaceutically acceptable salt, solvate, or prodrug thereof.

4. The compound of claim 1, wherein X is C, Y is N, and Z is N, having a structure of formula (IV):

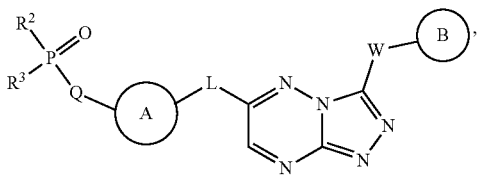
(IV)

or a pharmaceutically acceptable salt, solvate, or prodrug thereof.

5. The compound of claim 1, or a pharmaceutically acceptable salt, solvate, or prodrug thereof, wherein A is arylene or heteroarylene each optionally substituted by one to four substituents independent selected from the group consisting of halogen, $C_1$-$C_6$ alkyl, $C_1$-$C_6$ alkoxy, $C_1$-$C_6$ haloalkyl, and $C_1$-$C_6$ haloalkoxy.

6. The compound of claim 1, or a pharmaceutically acceptable salt, solvate, or prodrug thereof, wherein A is selected from the group consisting of:

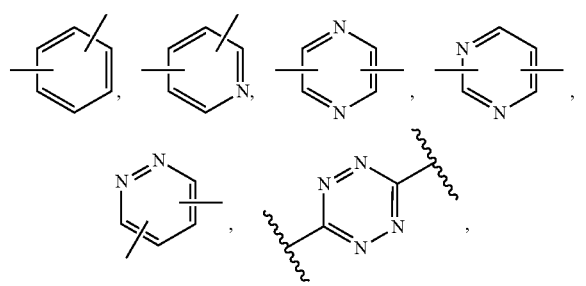

-continued

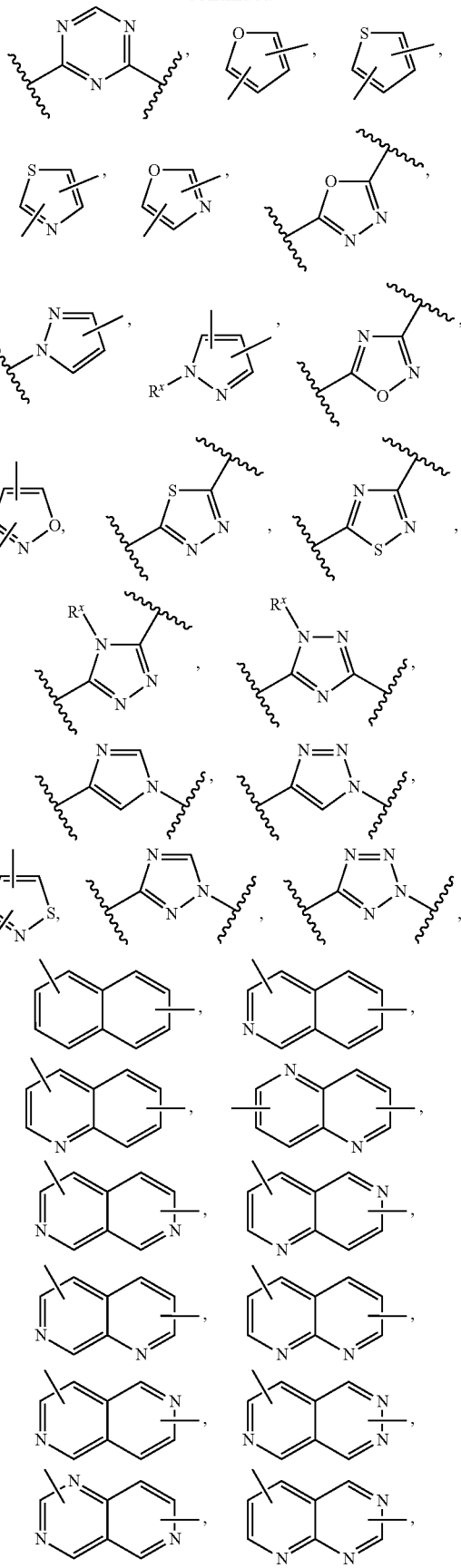

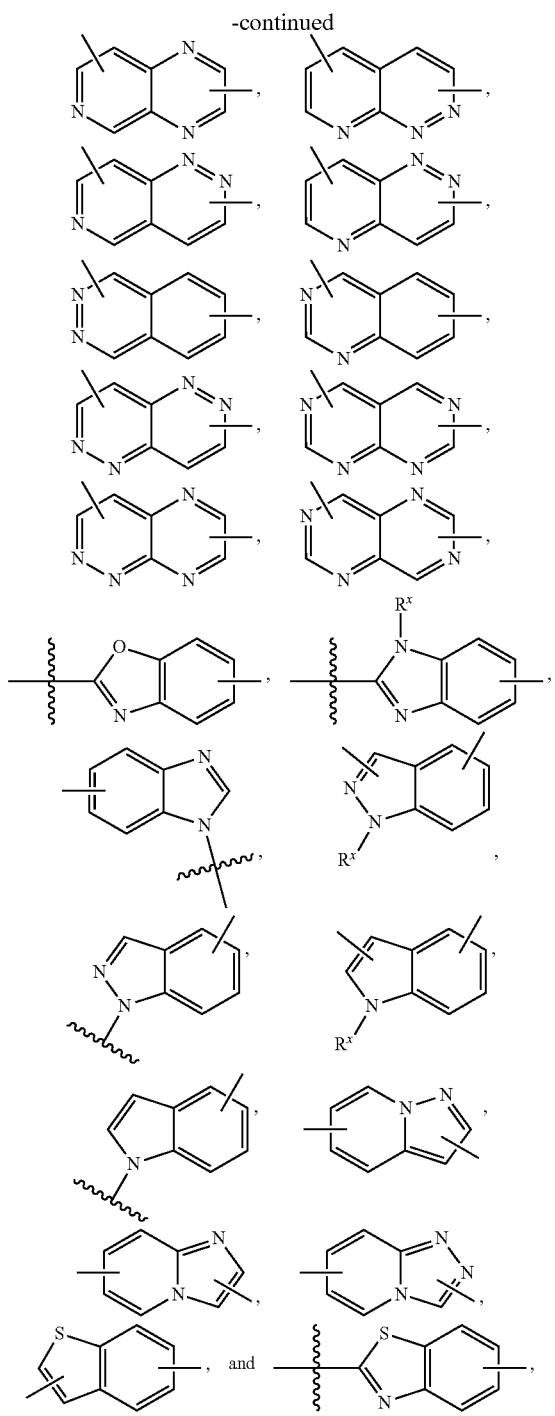

each optionally substituted by one, two, or three substituents independently selected from the group consisting of halogen, $C_1$-$C_4$ alkyl, $C_1$-$C_4$ alkoxy, $C_1$-$C_4$ haloalkyl, and $C_1$-$C_4$ haloalkoxy.

7. The compound of claim 1, or a pharmaceutically acceptable salt, solvate, or prodrug thereof, wherein L is absent or $NR^1$, and Q is absent or $C(R^Q)_2$.

8. The compound of claim 1, or a pharmaceutically acceptable salt, solvate, or prodrug thereof, wherein L is absent, and Q is $C(R^Q)_2$.

9. The compound of claim 1, or a pharmaceutically acceptable salt, solvate, or prodrug thereof, wherein L is $NR^1$, and Q is $C(R^Q)_2$.

10. The compound of claim 1, or a pharmaceutically acceptable salt, solvate, or prodrug thereof, wherein L is $NR^1$, and Q is absent.

11. The compound of claim 1, or a pharmaceutically acceptable salt, solvate, or prodrug thereof, wherein L and Q are absent.

12. The compound of claim 1, or a pharmaceutically acceptable salt, solvate, or prodrug thereof, wherein A, L, and Q are all absent.

13. The compound of claim 1, or a pharmaceutically acceptable salt, solvate, or prodrug thereof, wherein B is heteroaryl or heterocyclyl, each optionally substituted with one to five substituents independently selected from the group consisting of halogen, CN, $C_1$-$C_6$ alkyl, $C_1$-$C_6$ haloalkyl, —C(O) $R^{10}$, —$CO_2R^9$, —$OR^9$, —$NR^aR^b$, —C(O)$NR^aR^b$, and —$SO_2NR^aR^b$, wherein $R^9$ is hydrogen or $C_1$-$C_6$ alkyl, $R^{10}$ is $C_1$-$C_4$ alkyl, and $R^a$ and $R^b$ are each independently hydrogen or $C_1$-$C_4$ alkyl.

14. The compound of claim 1, or a pharmaceutically acceptable salt, solvate, or prodrug thereof, wherein B is selected from the group consisting of:

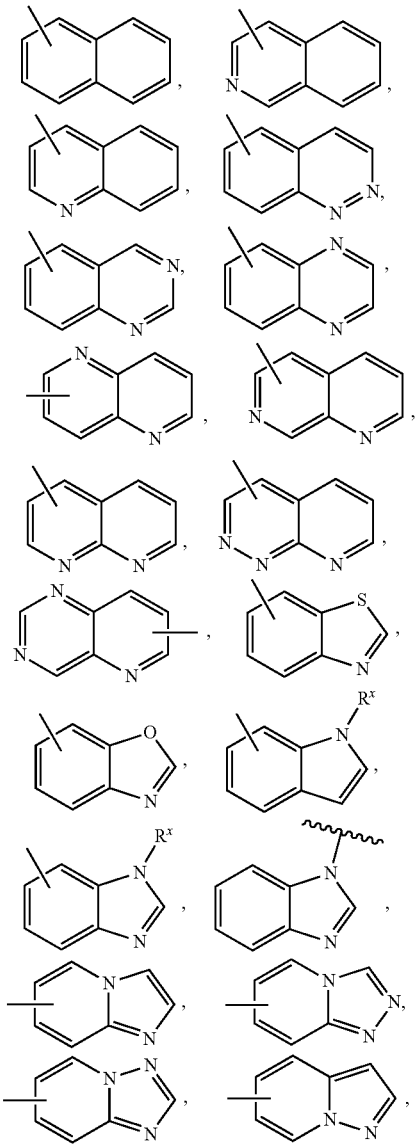

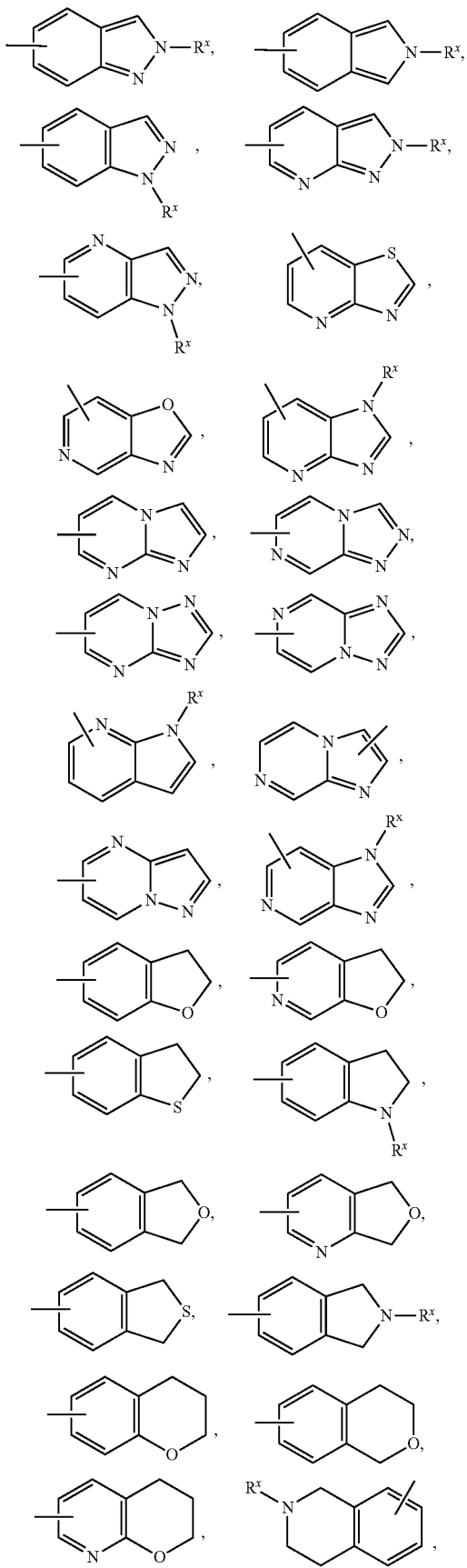

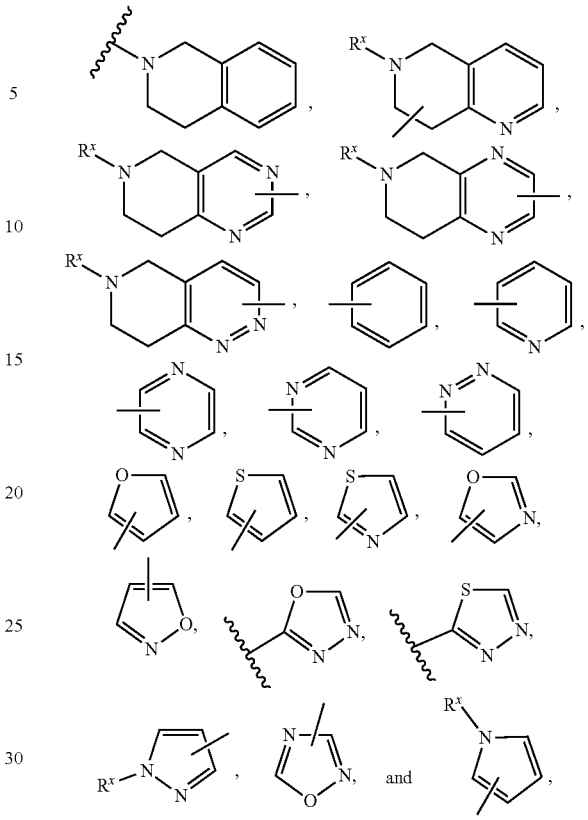

each optionally substituted by one, two, or three substituents independently selected from the group consisting of halogen, $C_1$-$C_6$ alkyl, $C_1$-$C_6$ alkoxy, $C_1$-$C_6$ haloalkyl, and $C_1$-$C_6$ haloalkoxy.

15. The compound of claim 1, or a pharmaceutically acceptable salt, solvate, or prodrug thereof, wherein W is $C(R^5R^6)$, wherein $R^5$ and $R^6$ are each independently H, halogen, or $C_1$-$C_4$ alkyl.

16. The compound of claim 1, wherein:
$R^2$ and $R^3$ are independently selected from the group consisting of $C_1$-$C_6$ alkyl, $C_3$-$C_6$ cycloalkyl, —$OR^4$, —$NR^7R^8$, and —$OCH_2$ (C=O)$OR^9$, wherein said alkyl or cycloalkyl is optionally substituted by one to four substituents independently selected from the group consisting of $C_1$-$C_4$ alkyl, $C_2$-$C_4$ alkenyl, $C_2$-$C_4$ alkynyl, $C_6$-$C_{10}$ aryl, 5- to 10-membered heteroaryl, $C_3$-$C_6$ cycloalkyl, 3- to 10-membered heterocyclyl, halogen, cyano, nitro, —$OR^9$, —$SR^9$, —$C(O)OR^9$, —$C(O)$ $R^{10}$, —$NR^aR^b$, and —$C(O)$ $NR^cR^d$;

$R^4$ is selected from the group consisting of hydrogen, $C_1$-$C_6$ alkyl, and benzyl;

$R^7$ and $R^8$ are independently selected from hydrogen, $C_1$-$C_6$ alkyl, $C_3$-$C_6$ cycloalkyl, and $C_6$-$C_{10}$ aryl; or alternatively, $R^7$ and $R^8$ together with the nitrogen atom to which they are attached, form a 4- to 6-membered ring, wherein said 4- to 6-membered ring optionally may contain one to three substituents independently selected from the group consisting of halogen, $C_1$-$C_6$ alkyl, $C_1$-$C_6$ haloalkyl, $C_6$-$C_{10}$ aryl, and —$OR^9$;

$R^9$ at each occurrence is independently H, $C_1$-$C_6$ alkyl, or $C_6$-$C_{10}$ aryl;

$R^{10}$ at each occurrence is independently selected from the group consisting of hydrogen, $C_1$-$C_6$ alkyl, $C_3$-$C_6$ cycloalkyl, $C_6$-$C_{10}$ aryl, and 5- to 10-membered heteroaryl;

$R^a$ and $R^b$ are each independently hydrogen or $C_1$-$C_6$ alkyl; and $R^c$ and $R^d$ are independently hydrogen or $C_1$-$C_4$ alkyl.

17. The compound of claim 1, having a structure of formula (V), (VI), (VII), or (VIII):

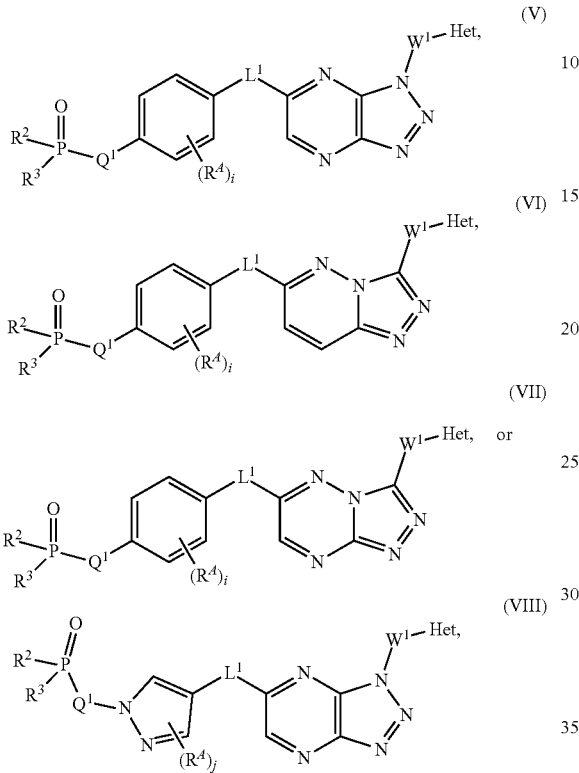

or a pharmaceutically acceptable salt, solvate, or prodrug thereof, wherein:

i is 1, 2, 3, or 4;

j is 1 or 2; and $R^A$ at each occurrence is independently selected from the group consisting of halogen, $C_1$-$C_6$ alkyl, $C_1$-$C_6$ alkoxy, $C_1$-$C_6$ haloalkyl, $C_1$-$C_6$ haloalkoxy, hydroxy, $C_1$-$C_6$ acyl, cyano, nitro, and $NR^cR^d$;

$L^1$ is a bond, O, S, $NR^1$, or $C(R^L)_2$, wherein $R^L$ at each occurrence is independently hydrogen, halogen, or $C_1$-$C_4$ alkyl;

$Q^1$ is a bond or $C(R^Q)_2$, wherein $R^Q$ at each occurrence is independently hydrogen, halogen, or $C_1$-$C_4$ alkyl;

$R^1$ at each occurrence is independently H or $C_1$-$C_4$ alkyl;

$R^2$ and $R^3$ are each independently selected from the group consisting of $C_1$-$C_6$ alkyl, $C_3$-$C_6$ cycloalkyl, $-NR^7R^8$, $OR^4$, and $-OCH_2$ $(C=O)OR^9$, wherein the alkyl is optionally substituted by one to three substituents independently selected from the group consisting of $C_6$-$C_{10}$ aryl, 5- to 10-membered heteroaryl, $C_3$-$C_6$ cycloalkyl, 3- to 10-membered heterocyclyl, halogen, cyano, nitro, $-OR^9$, $-SR^9$, $-C(O)OR^9$, $-C(O)$ $R^{10}$, $-NR^aR^b$, and $-C(O)NR^cR^d$ $R^4$ at each occurrence is independently H, $C_1$-$C_4$ alkyl, or phenyl;

$W^1$ is $CR^5R^6$, wherein $R^5$ and $R^6$ are each independently H, halogen, or $C_1$-$C_4$ alkyl, or $R^5$ and $R^6$ together with the carbon atom to which they are attached form a 3- to 6-membered ring optionally substituted;

$R^7$ and $R^8$ are independently selected from hydrogen, $C_1$-$C_6$ alkyl, $C_3$-$C_6$ cycloalkyl, $C_6$-$C_{10}$ aryl, 5- to 10-membered heteroaryl, and 5- to 10-membered heterocyclyl; or alternatively, $R^7$ and $R^8$ together with the nitrogen atom to which they are attached, form a 4- to 6-membered ring, wherein said 4- to 6-membered ring optionally may contain one to three substituents independently selected from the group consisting of halogen, $C_1$-$C_6$ alkyl, $C_1$-$C_6$ haloalkyl, $C_6$-$C_{10}$ aryl, and $-OR^9$;

"Het" is heteroaryl or heterocyclyl, each optionally substituted with one to four substituents independently selected from the group consisting of halogen, $C_1$-$C_6$ alkyl, $C_1$-$C_6$ haloalkyl, $C_2$-$C_6$ alkenyl, $C_3$-$C_6$ cycloalkyl, $C_6$-$C_{10}$ aryl, 5- to 10-membered heteroaryl, 3- to 10-membered heterocyclyl, and CN;

$R^9$ at each occurrence is independently H or $C_1$-6 alkyl;

$R^{10}$ at each occurrence is independently H or $C_1$-6 alkyl;

$R^{13}$ at each occurrence is independently hydrogen, $C_1$-$C_6$ alkyl, or $C_1$-$C_6$ haloalkyl;

$R^{14}$ at each occurrence is independently hydrogen or $C_1$-$C_6$ alkyl;

$R^a$ and $R^b$ are independently selected from hydrogen, $C_1$-$C_6$ alkyl, $C_3$-$C_6$ cycloalkyl, $C_6$-$C_{10}$ aryl, 5- to 10-membered heteroaryl, and benzyl; and $R^c$ and $R^d$ are independently hydrogen or $C_1$-$C_6$ alkyl.

18. The compound of claim 17, or a pharmaceutically acceptable salt or solvate thereof, wherein $L^1$ is absent or $NR^1$, and $Q^1$ is absent or $C(R^Q)_2$.

19. The compound of claim 17, or a pharmaceutically acceptable salt or solvate thereof, wherein $L^1$ is absent, and $Q^1$ is $C(R^Q)_2$.

20. The compound of claim 17, or a pharmaceutically acceptable salt or solvate thereof, wherein $L^1$ is $NR^1$, and $Q^1$ is $C(R^Q)_2$.

21. The compound of claim 17, or a pharmaceutically acceptable salt or solvate thereof, wherein $L^1$ is $NR^1$, and $Q^1$ is absent.

22. The compound of claim 17, or a pharmaceutically acceptable salt or solvate thereof, wherein $L^1$ and $Q^1$ are both absent.

23. The compound of claim 17, or a pharmaceutically acceptable salt, solvate, or prodrug thereof, wherein the Het is selected from the group consisting of:

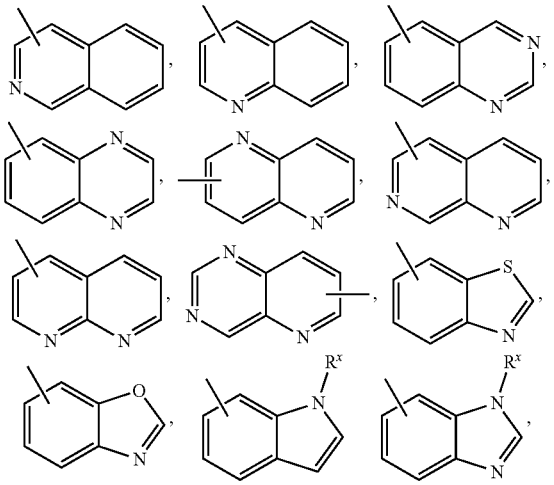

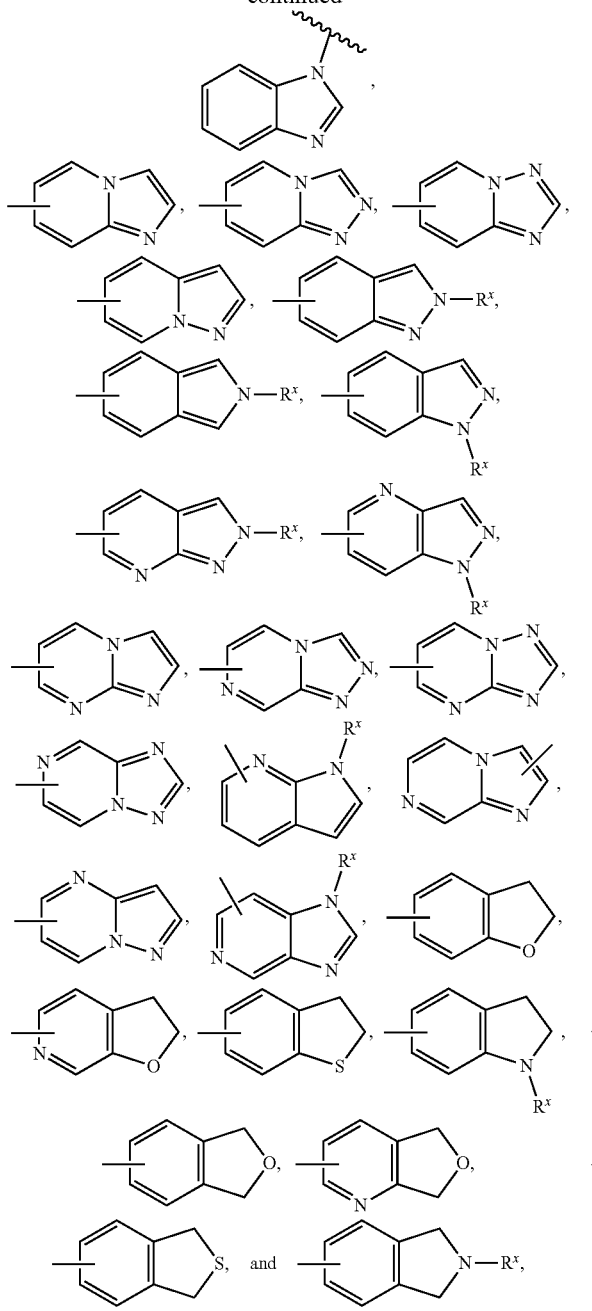

each optionally substituted by one, two, or three substituents independently selected from the group consisting of halogen, $C_1$-$C_6$ alkyl, $C_1$-$C_6$ alkoxy, $C_1$-$C_6$ haloalkyl, and $C_1$-$C_6$ haloalkoxy.

24. The compound of claim 17, wherein $R^2$ and $R^3$ are independently selected from the group consisting of $C_1$-$C_6$ alkyl, $C_3$-$C_6$ cycloalkyl, —$OR^4$, —$NR^7R^8$, and —$OCH_2$(C=O)$OR^9$, wherein said alkyl or cycloalkyl is optionally substituted by one to four substituents independently selected from the group consisting of $C_1$-$C_4$ alkyl, $C_6$-$C_{10}$ aryl, 5- to 10-membered heteroaryl, and $C_3$-$C_6$ cycloalkyl; wherein $R^4$ is hydrogen or $C_1$-$C_6$ alkyl, $R^7$ and $R^8$ are independently hydrogen or $C_1$-$C_4$ alkyl, and $R^9$ is $C_1$-$C_4$ alkyl.

25. The compound of claim 1, or a pharmaceutically acceptable salt, solvate or prodrug thereof, selected from the Compound List 1

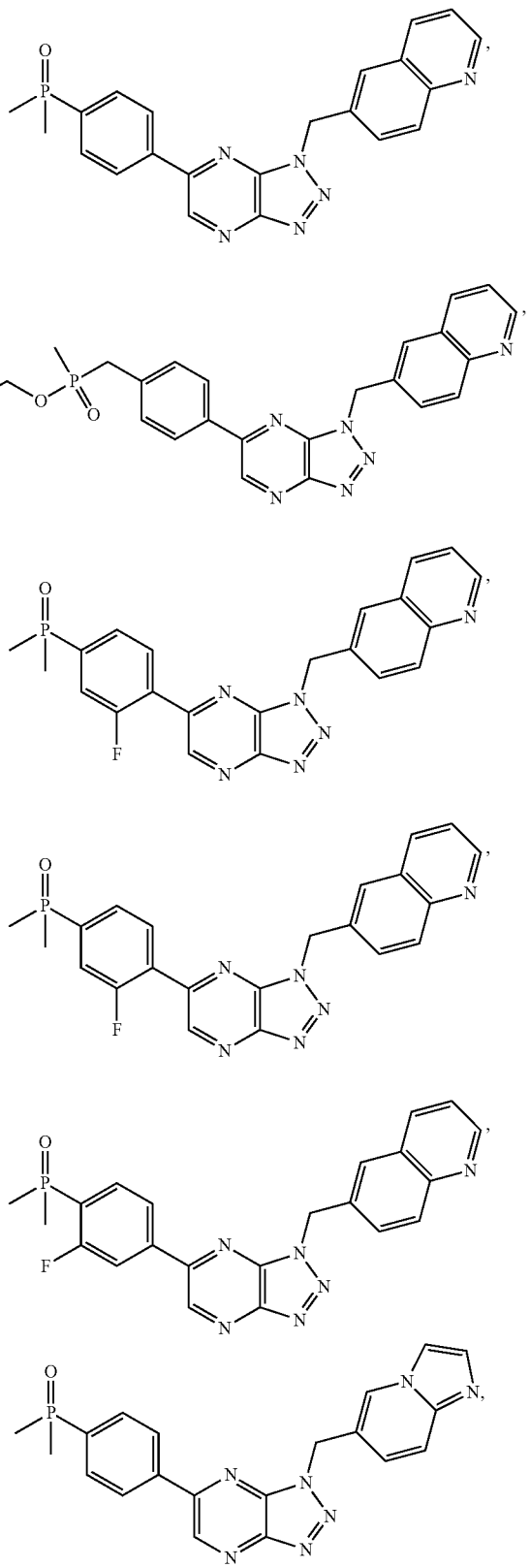

105
-continued
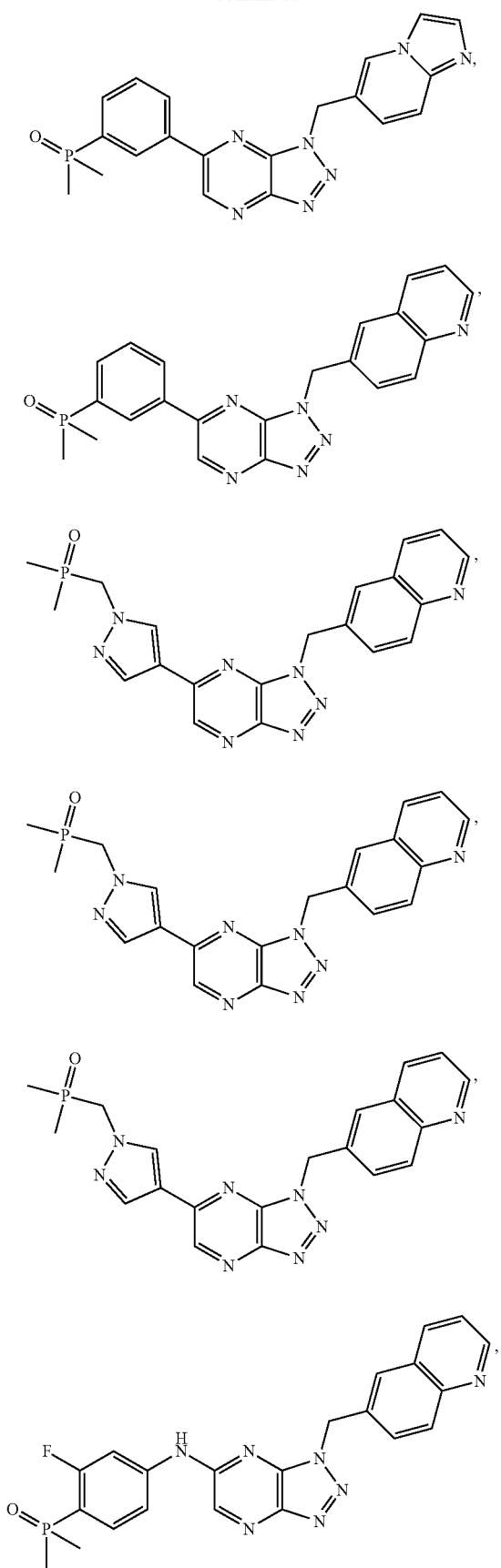 [SMILES: CP(C)(=O)c1cccc(-c2cnc3nnn(Cc4ccc5nccn5c4)c3n2)c1 ; CP(C)(=O)c1cccc(-c2cnc3nnn(Cc4ccc5ncccc5c4)c3n2)c1 ; CP(C)(=O)Cn1cc(-c2cnc3nnn(Cc4ccc5ncccc5c4)c3n2)cn1 ; CP(C)(=O)Cn1cc(-c2cnc3nnn(Cc4ccc5ncccc5c4)c3n2)cn1 ; CP(C)(=O)Cn1cc(-c2cnc3nnn(Cc4ccc5ncccc5c4)c3n2)cn1 ; CP(C)(=O)c1ccc(Nc2cnc3nnn(Cc4ccc5ncccc5c4)c3n2)cc1F]
106
-continued
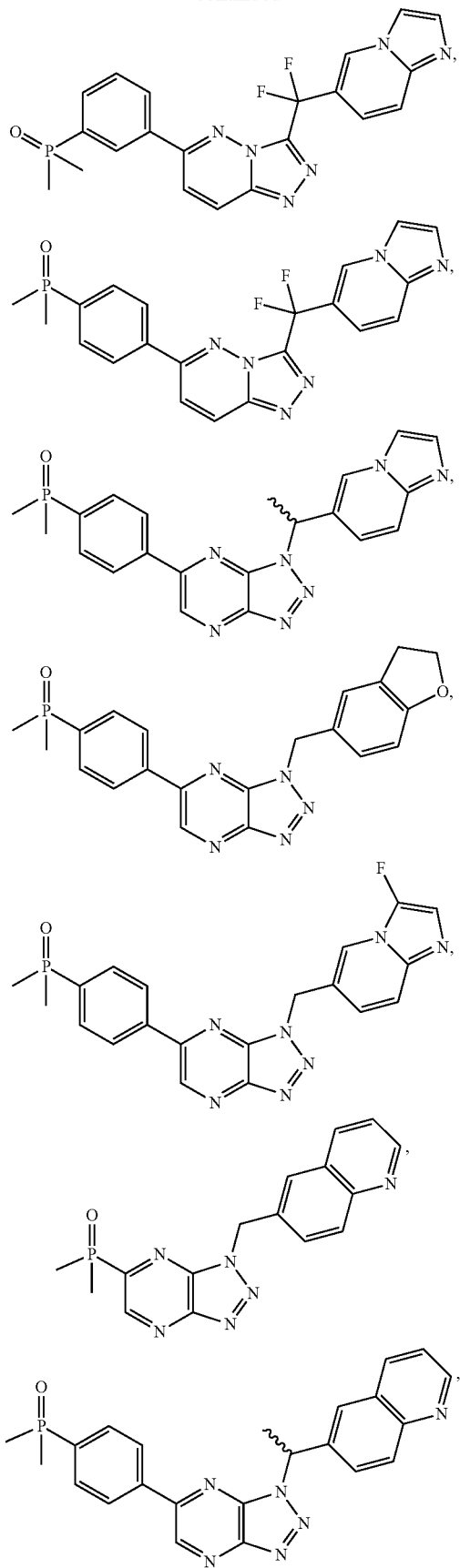

107
-continued
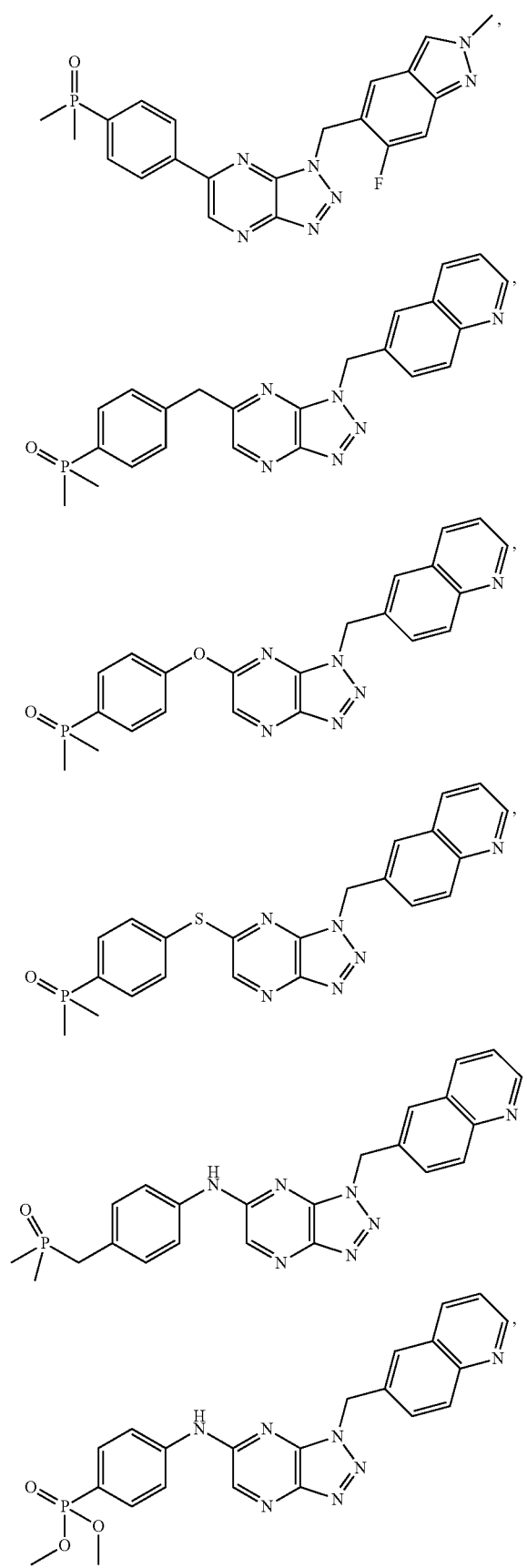
108
-continued
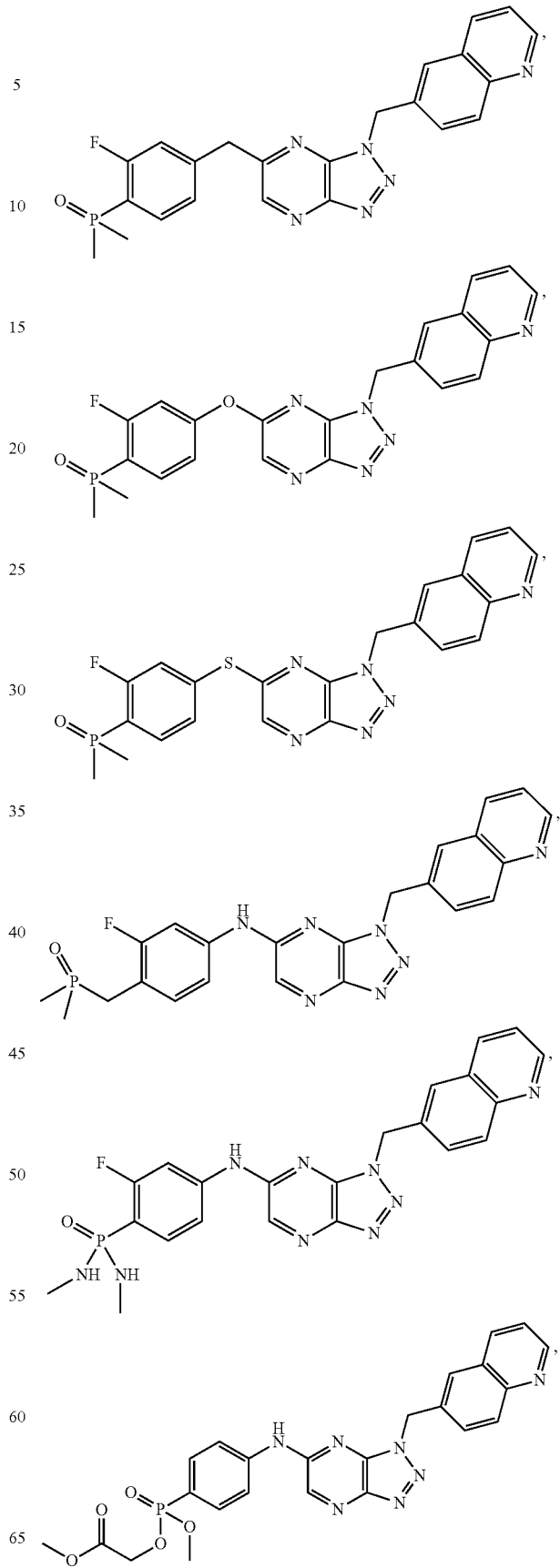

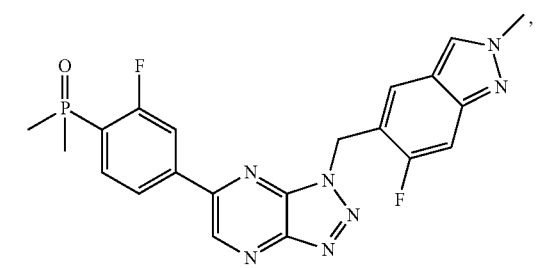
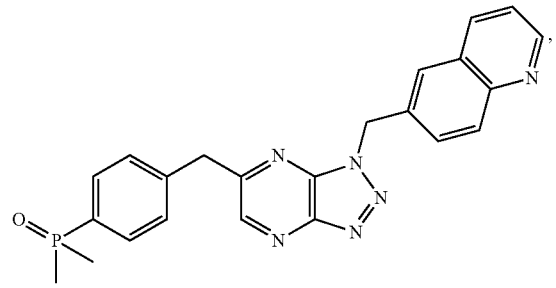
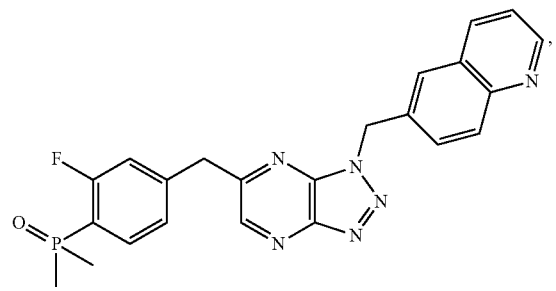
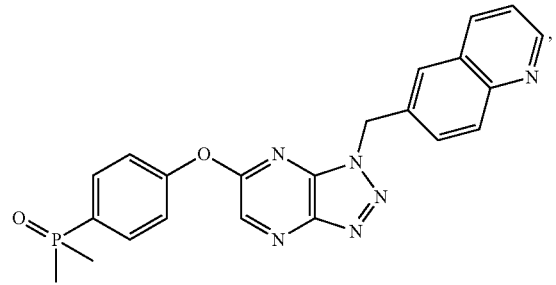
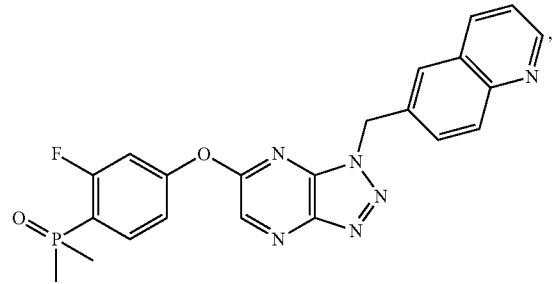
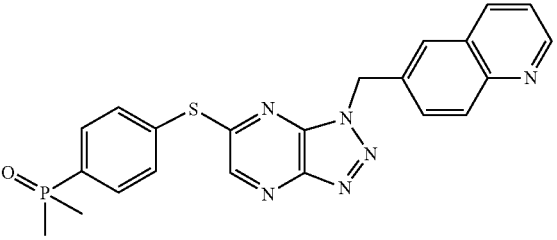
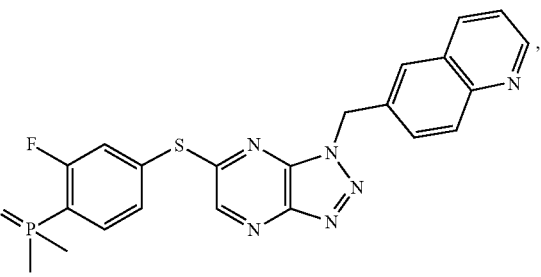
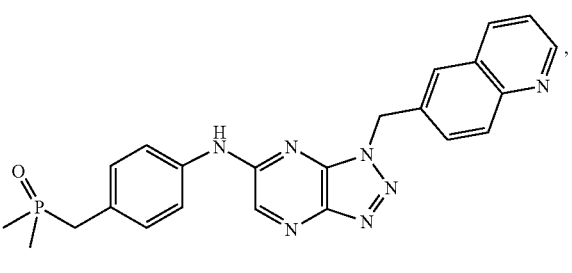
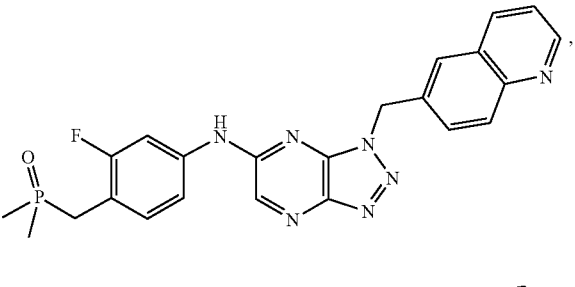
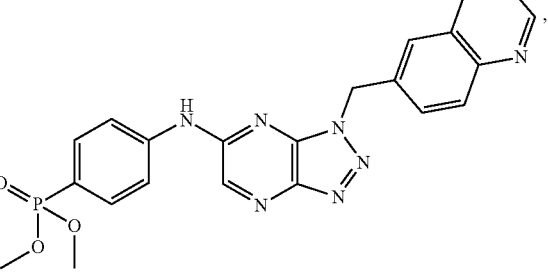
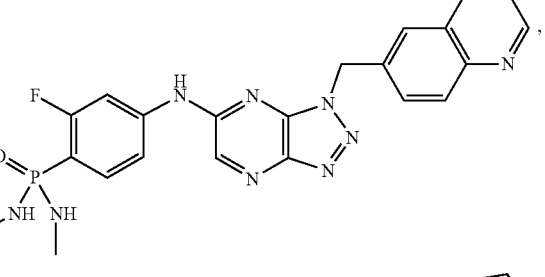
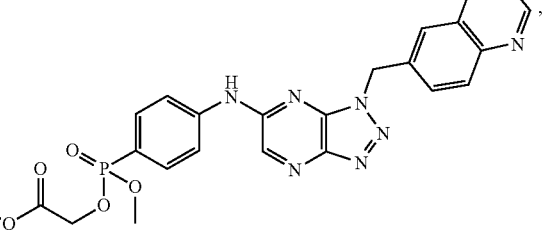

111
-continued
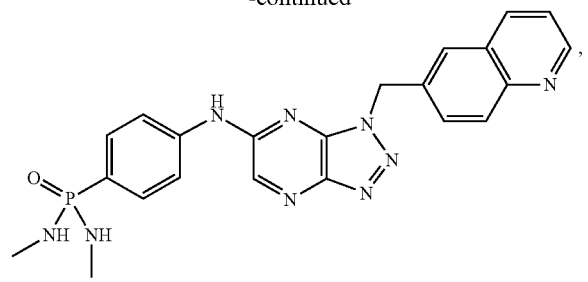
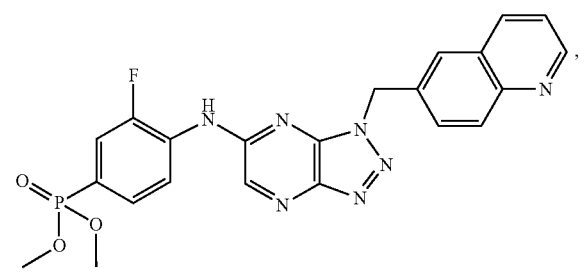
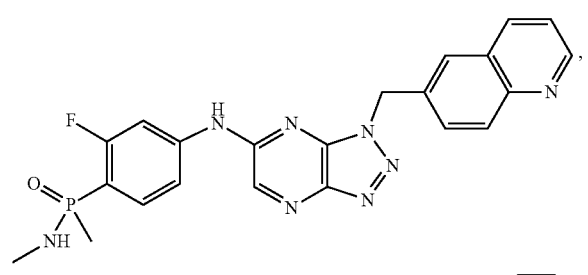
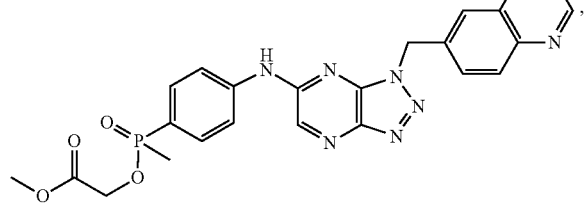
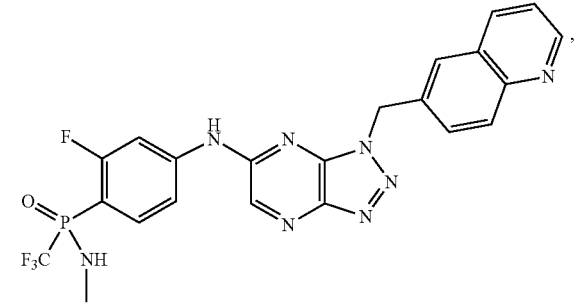
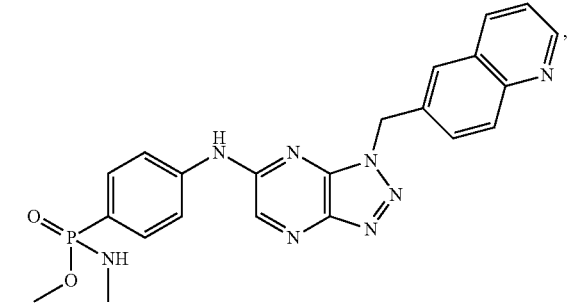 [SMILES: CNP(=O)(OC)c1ccc(Nc2cnc3nnn(Cc4ccc5ncccc5c4)c3n2)cc1]
112
-continued 113
-continued
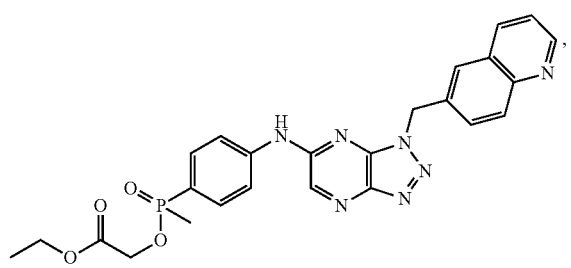
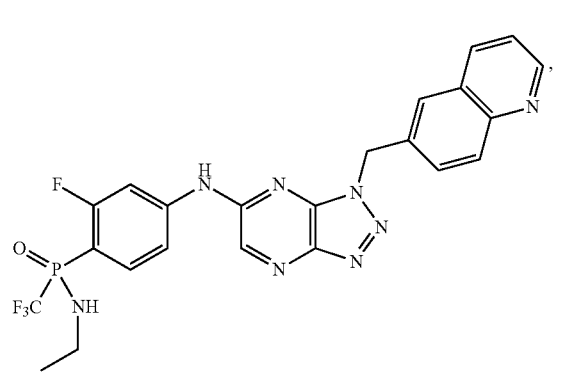
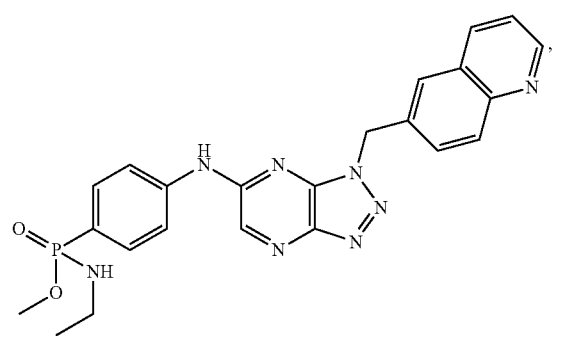
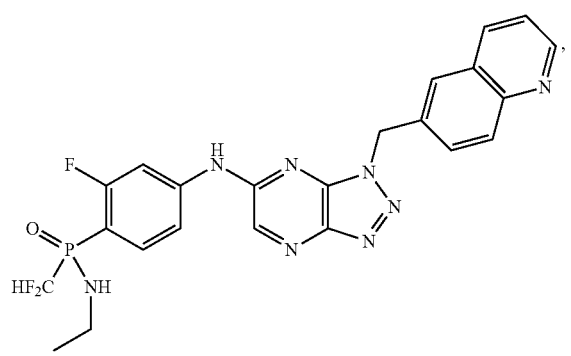
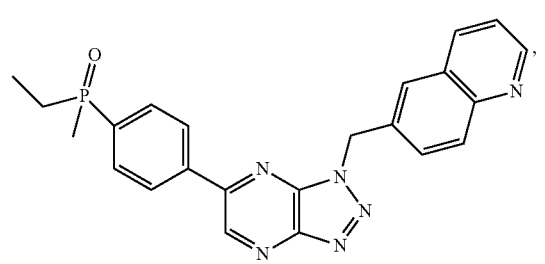
114
-continued
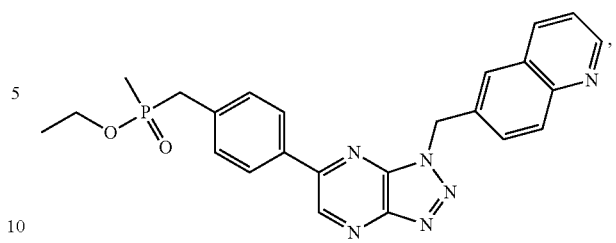
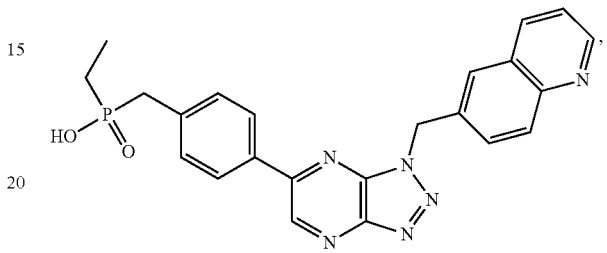
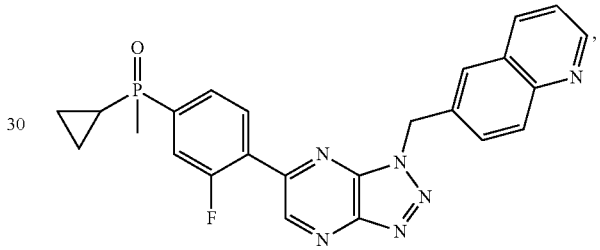
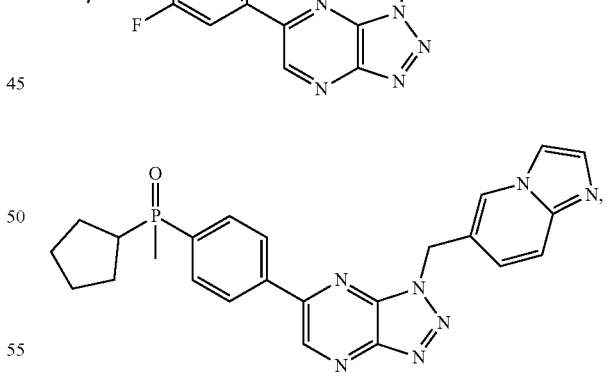
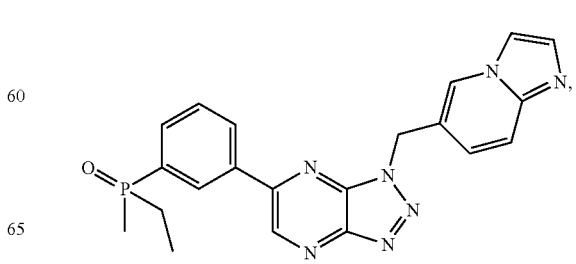

115
-continued
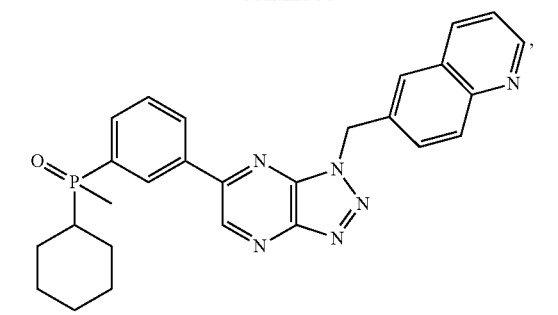
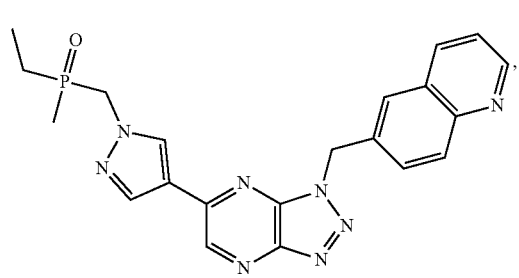
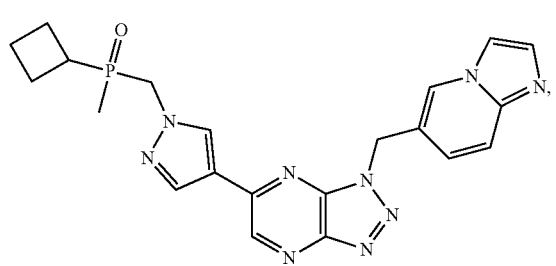
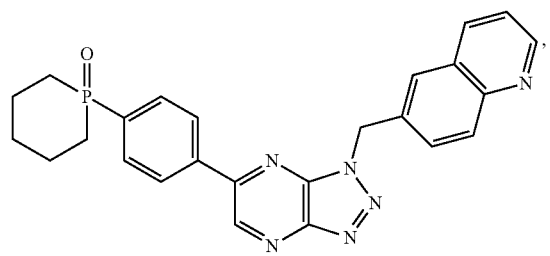
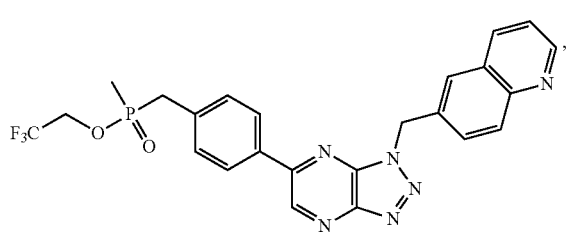
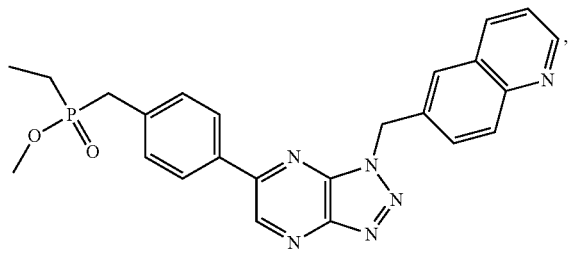
116
-continued
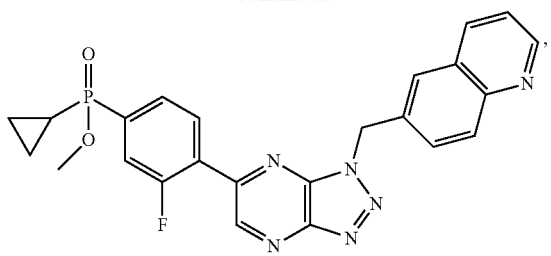
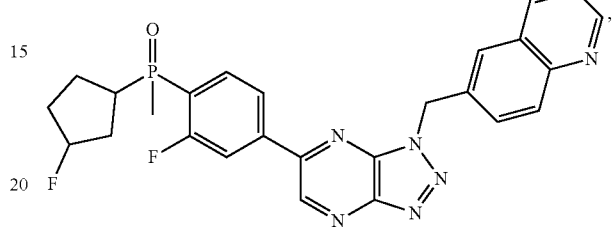
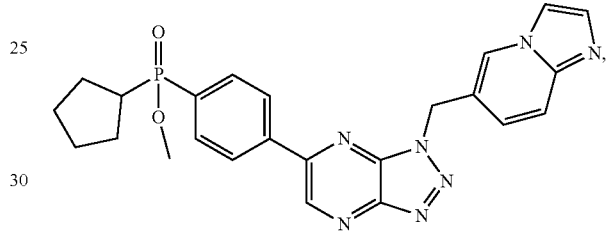
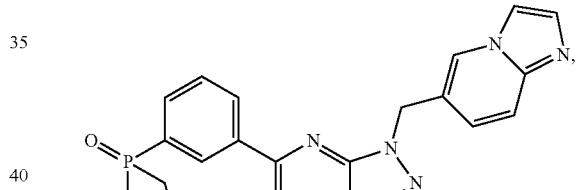
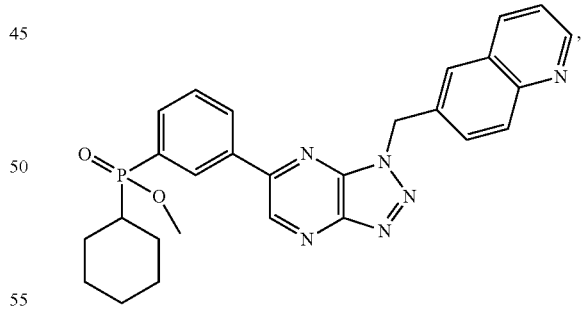
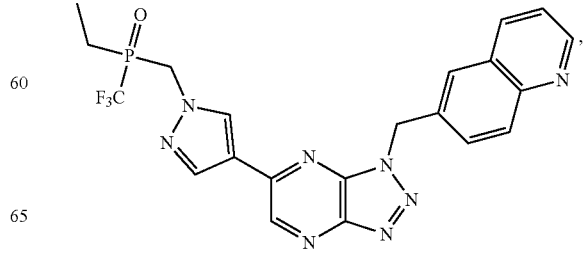

117
-continued
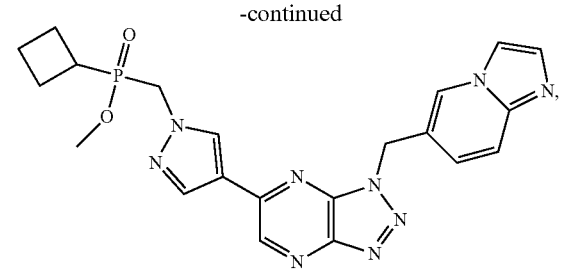
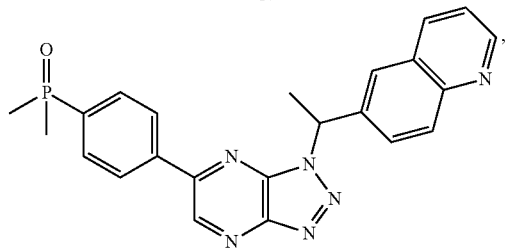
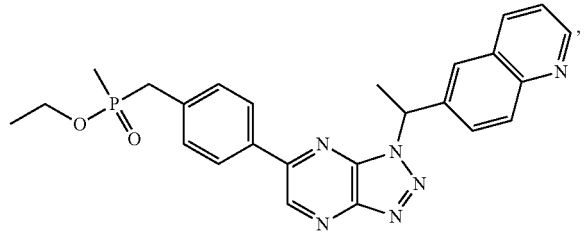
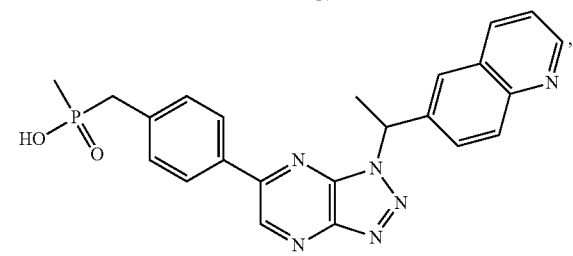
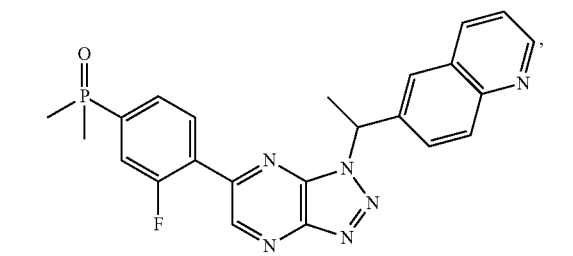
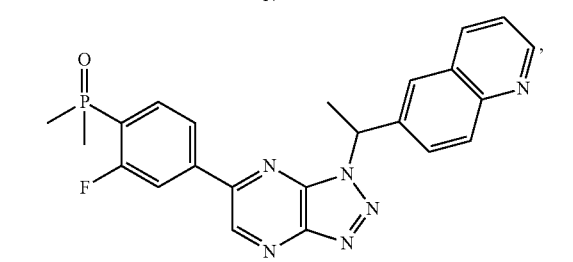
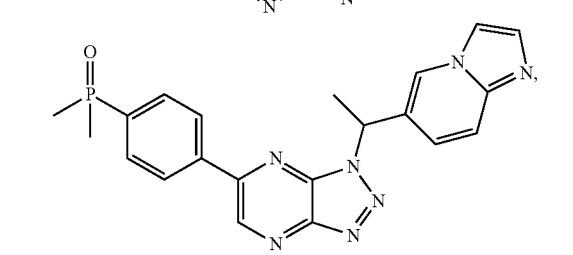
118
-continued
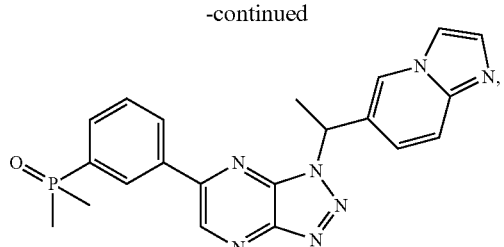
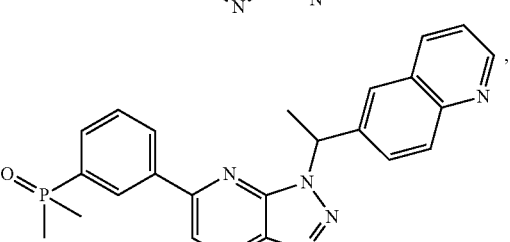
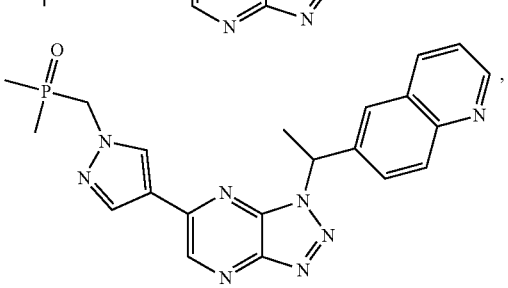
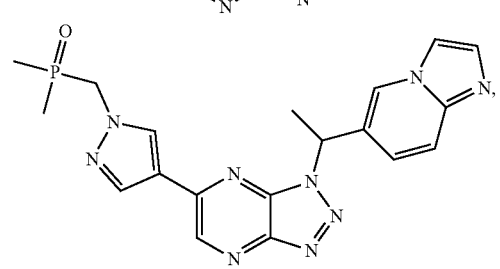
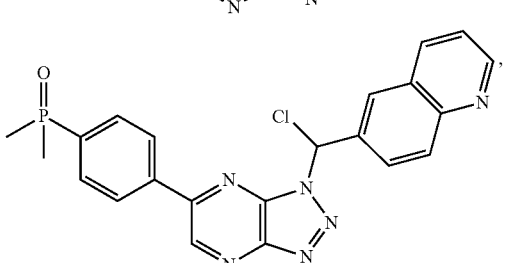
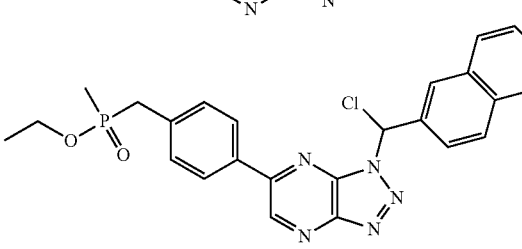
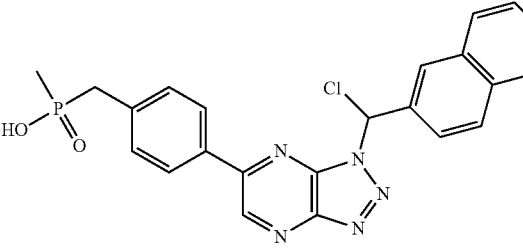

119
-continued
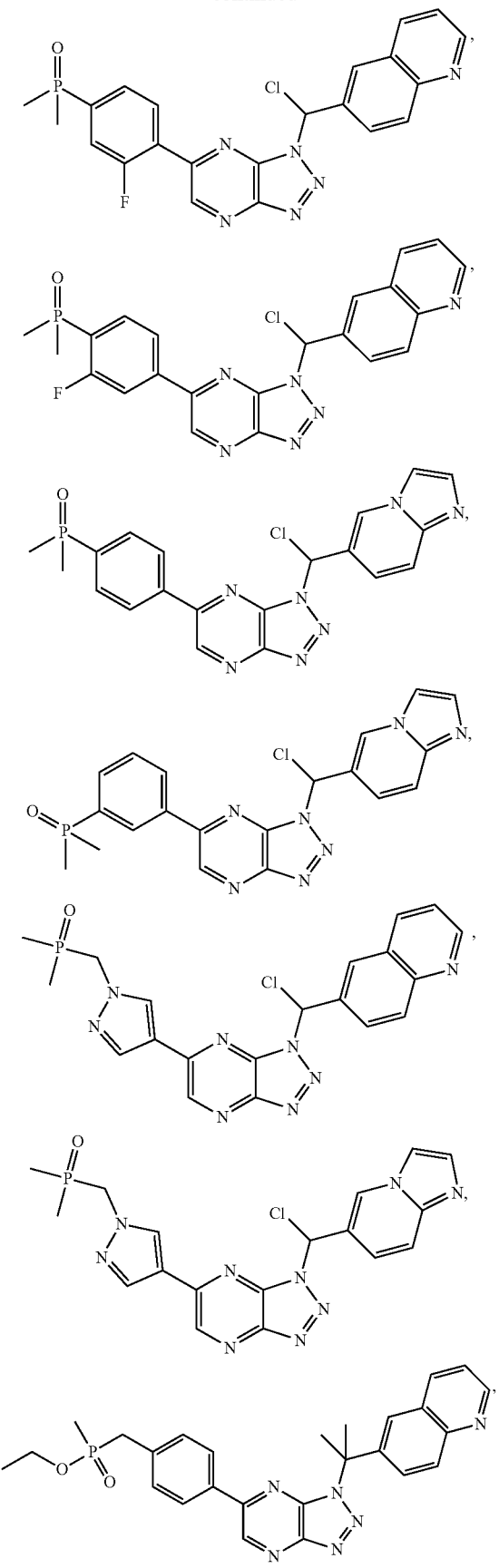
120
-continued
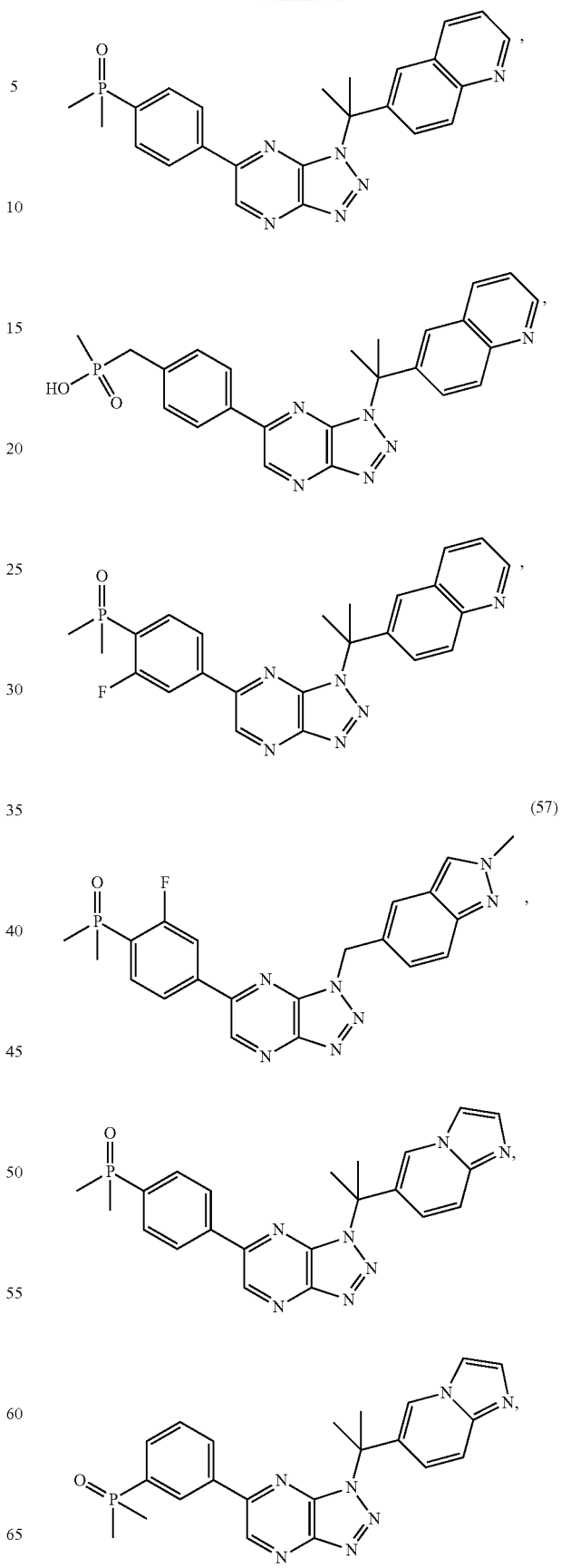
(57)

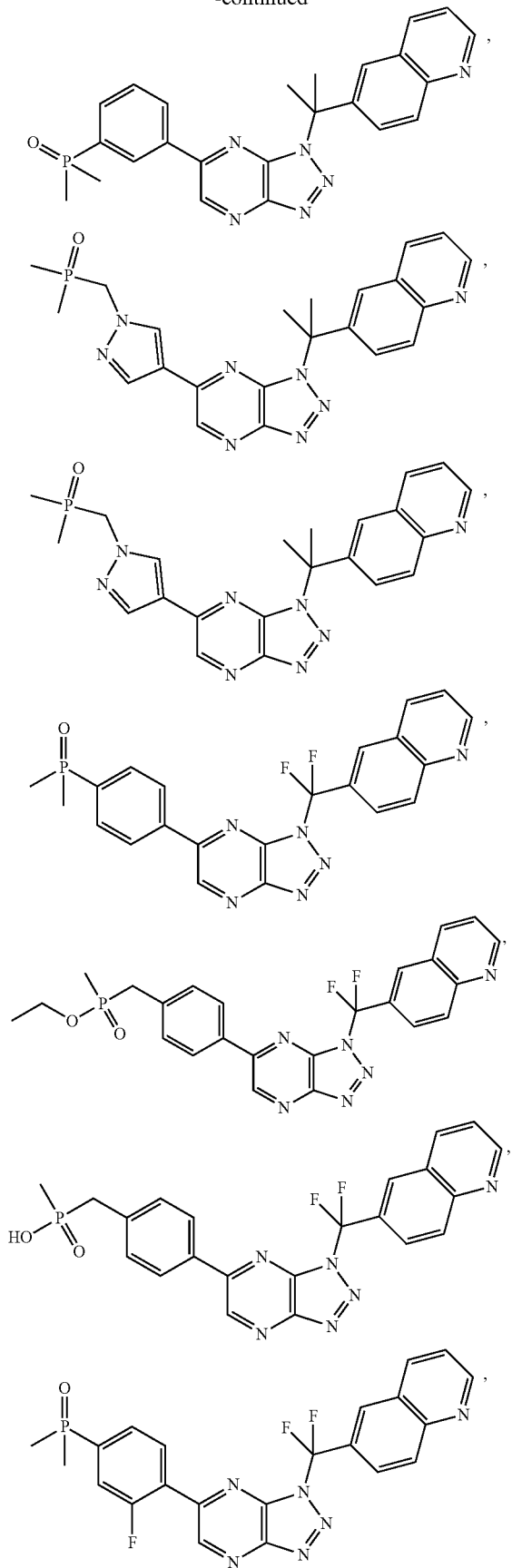

-continued
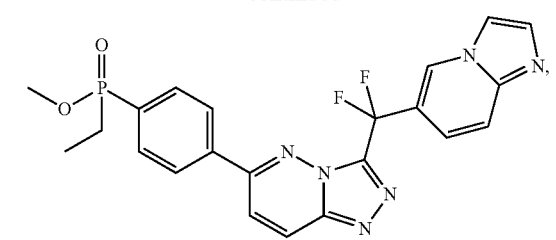
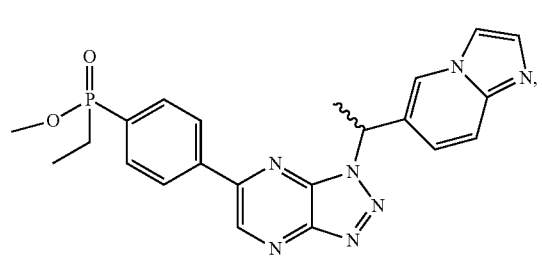
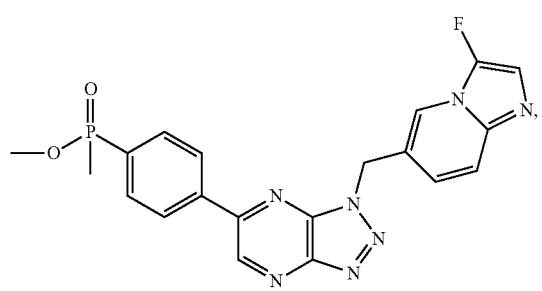
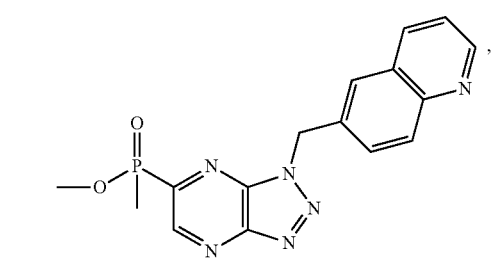
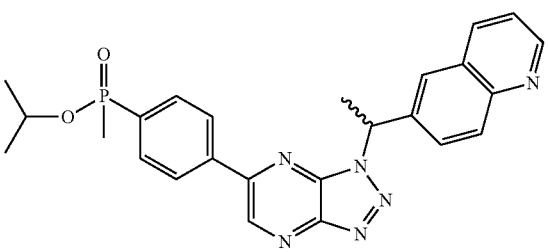
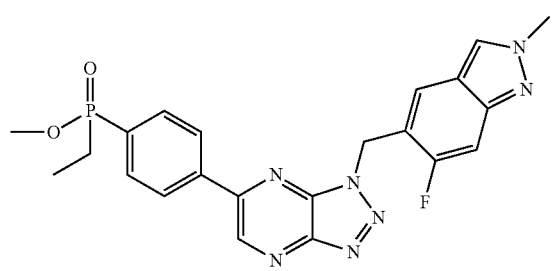
-continued
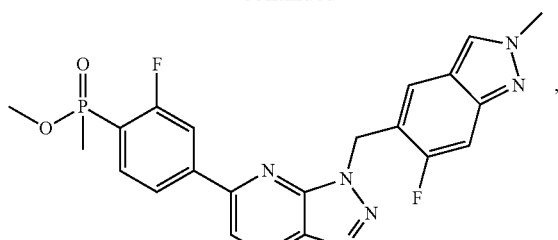
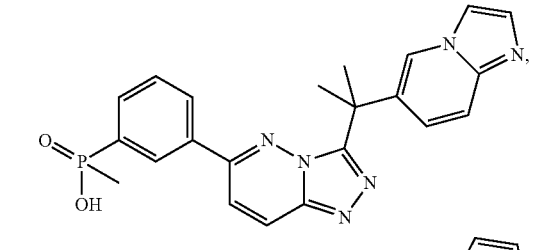
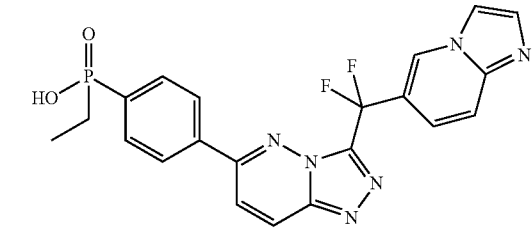
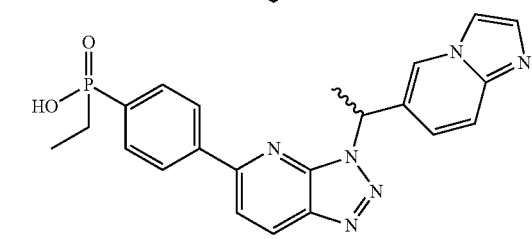
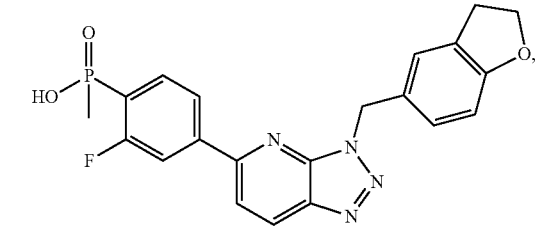
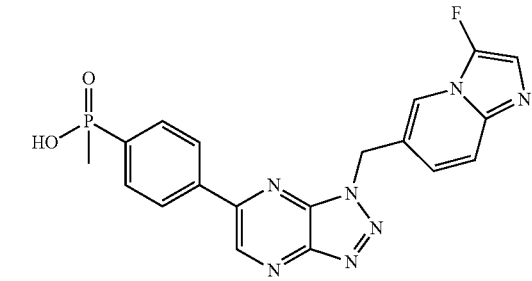
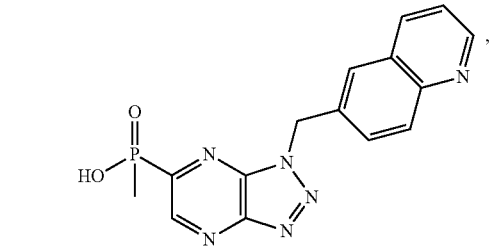

125
-continued
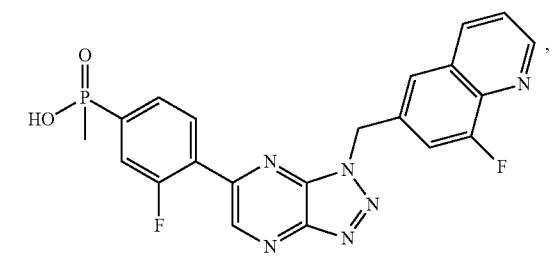
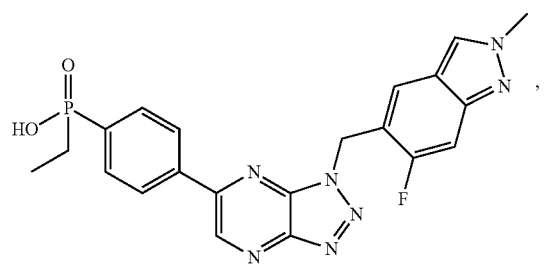
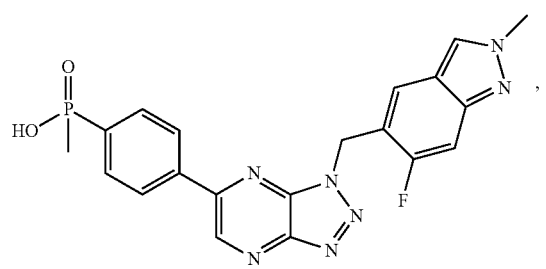
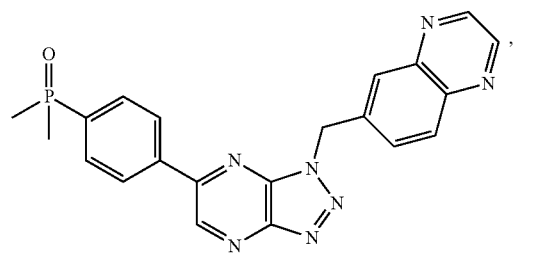
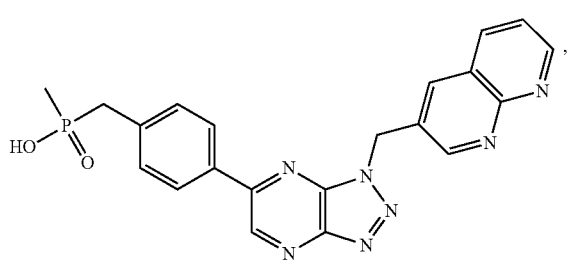
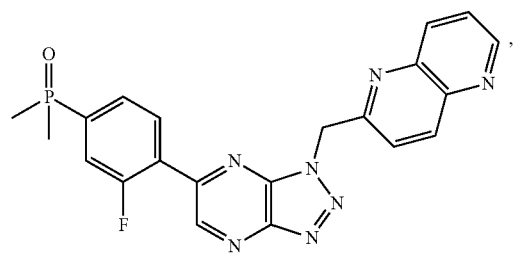
126
-continued
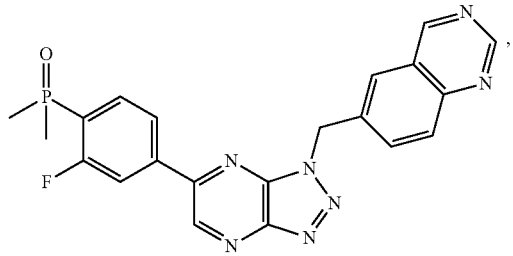
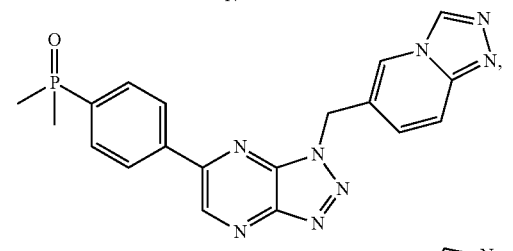
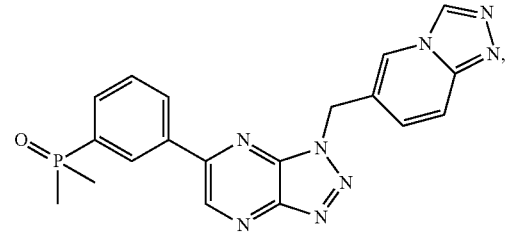
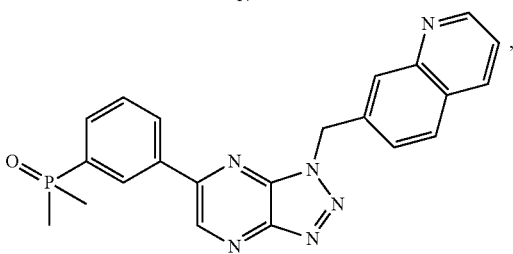
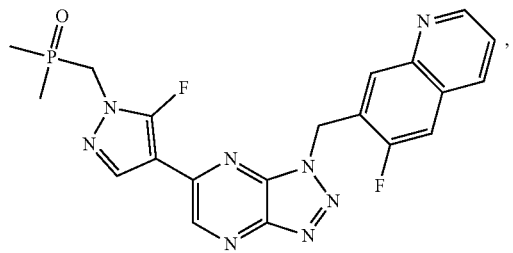
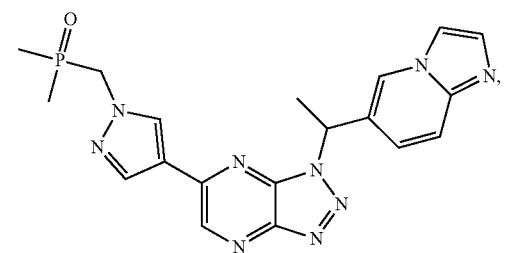
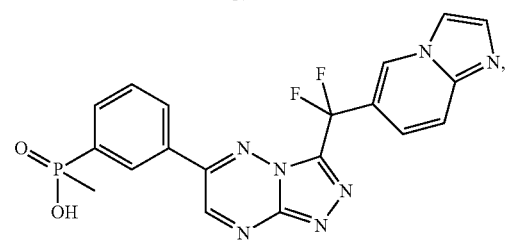

127
-continued
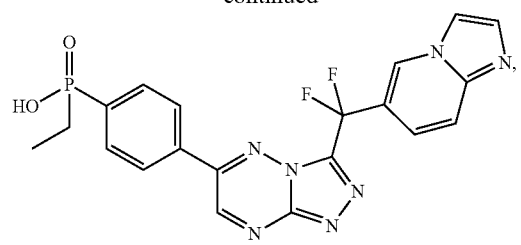
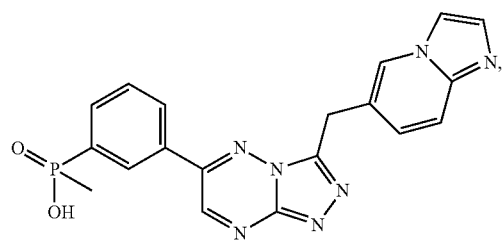
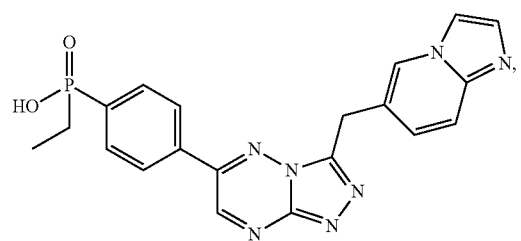
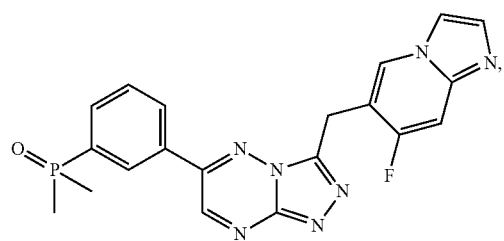
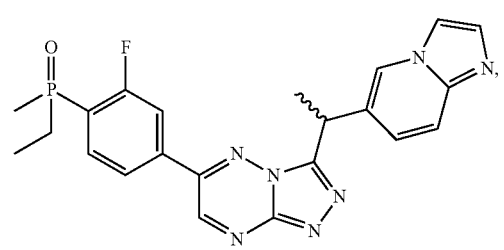
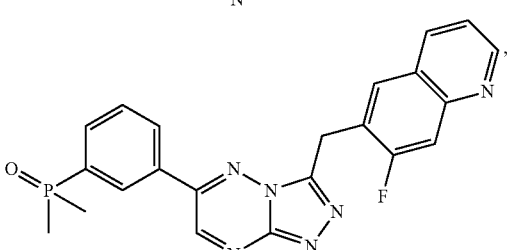
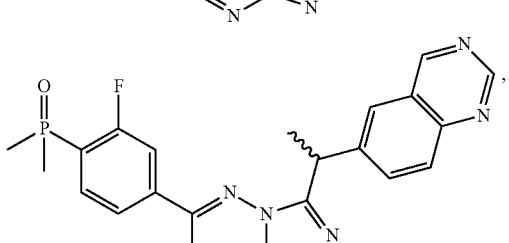
128
-continued
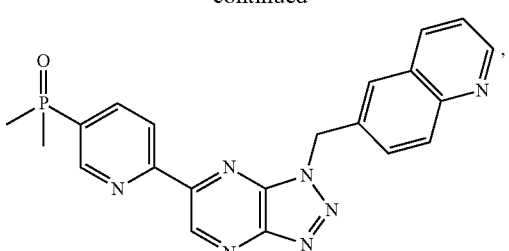
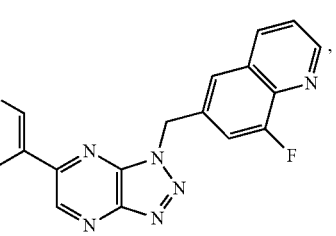
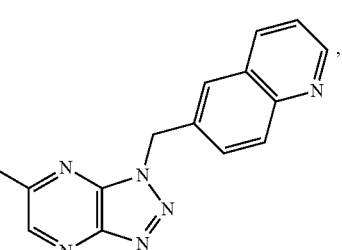
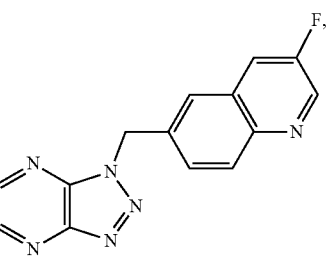
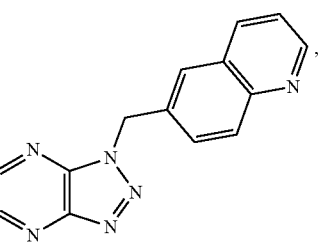
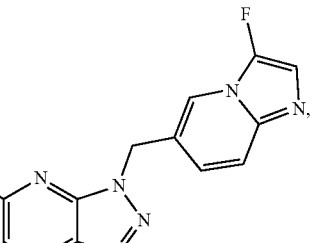

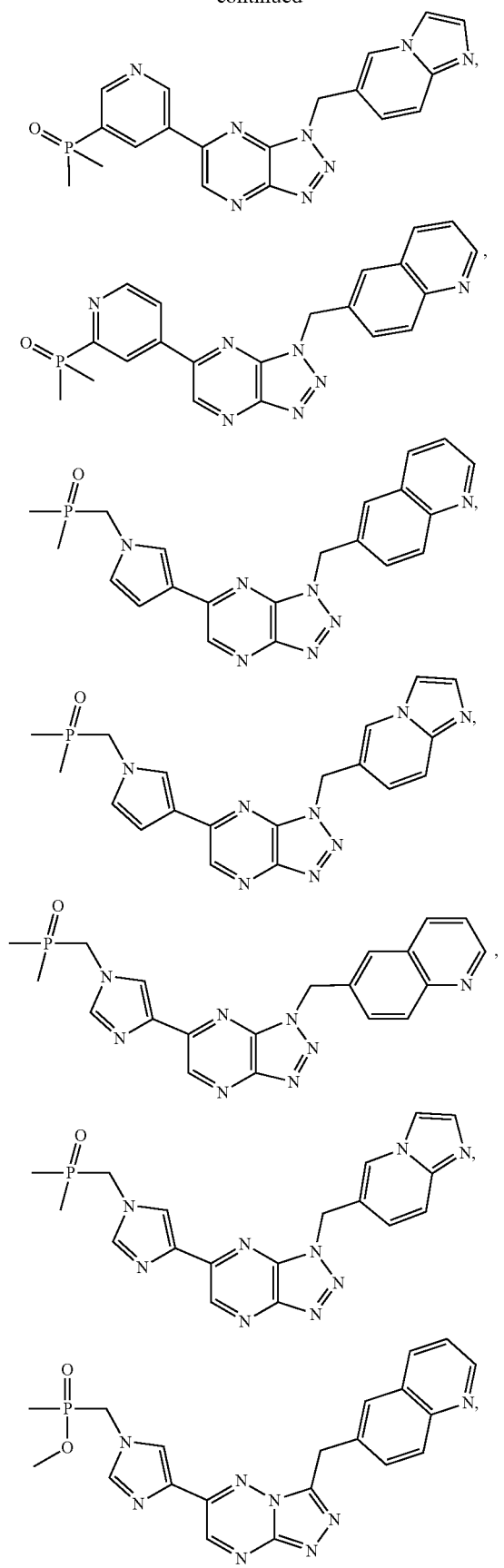
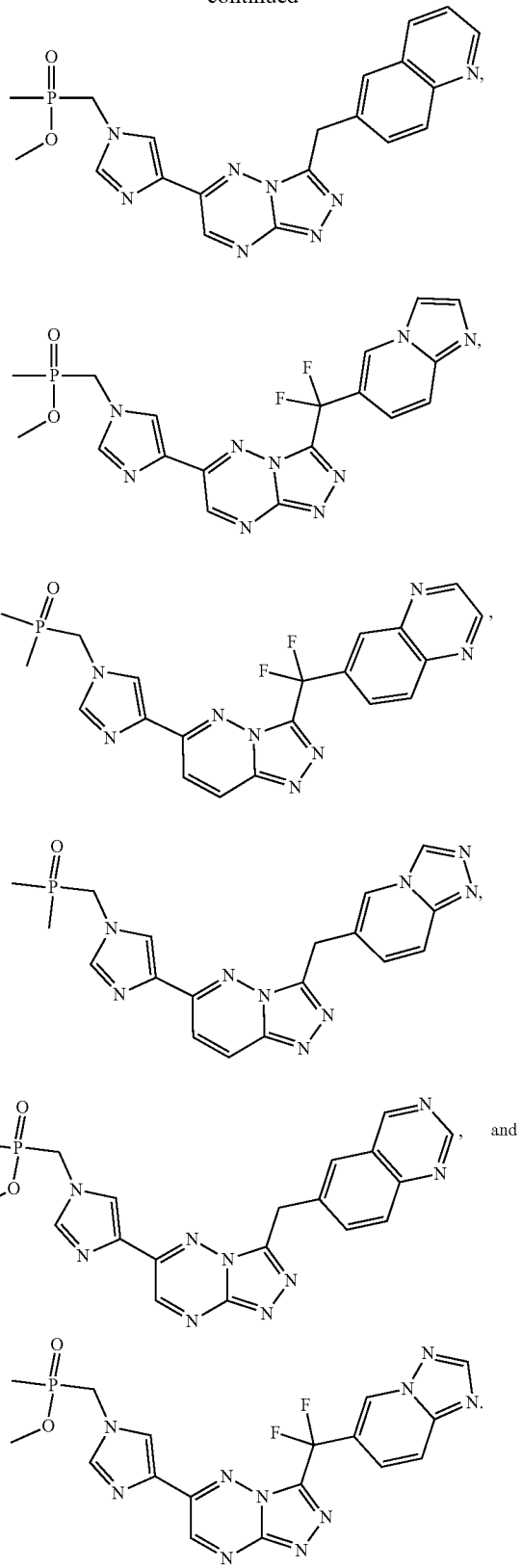
26. The compound of claim 1, or a pharmaceutically acceptable salt, solvate or prodrug thereof, selected from the group consisting of:

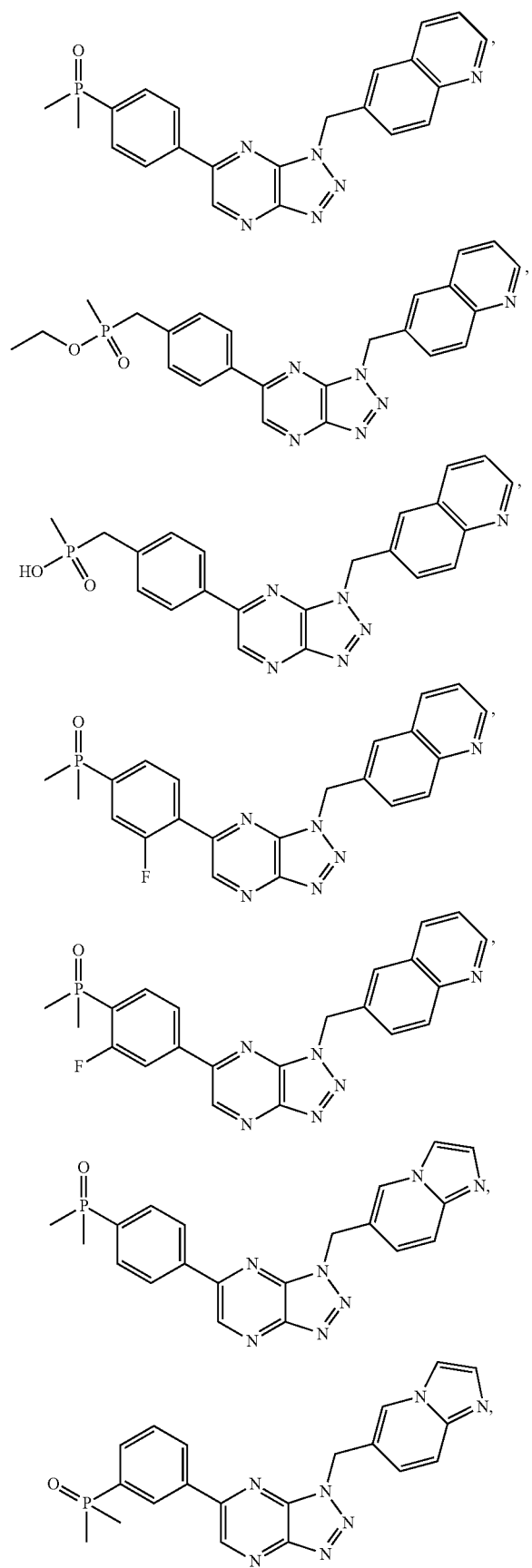
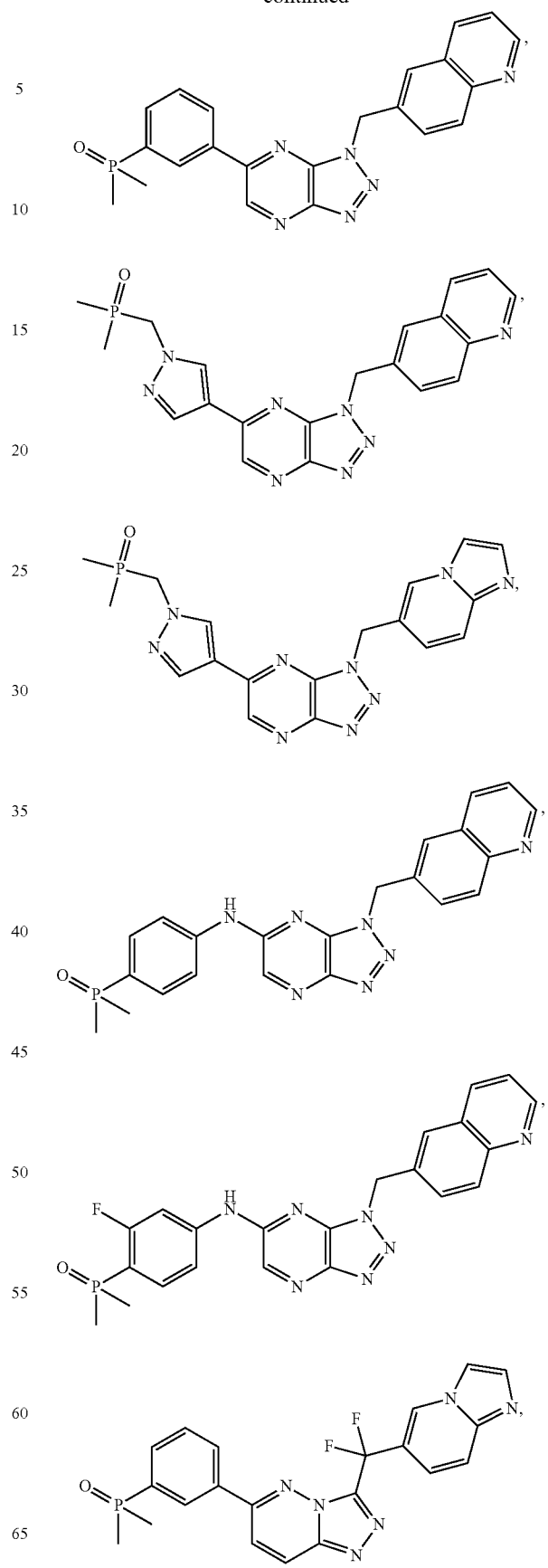

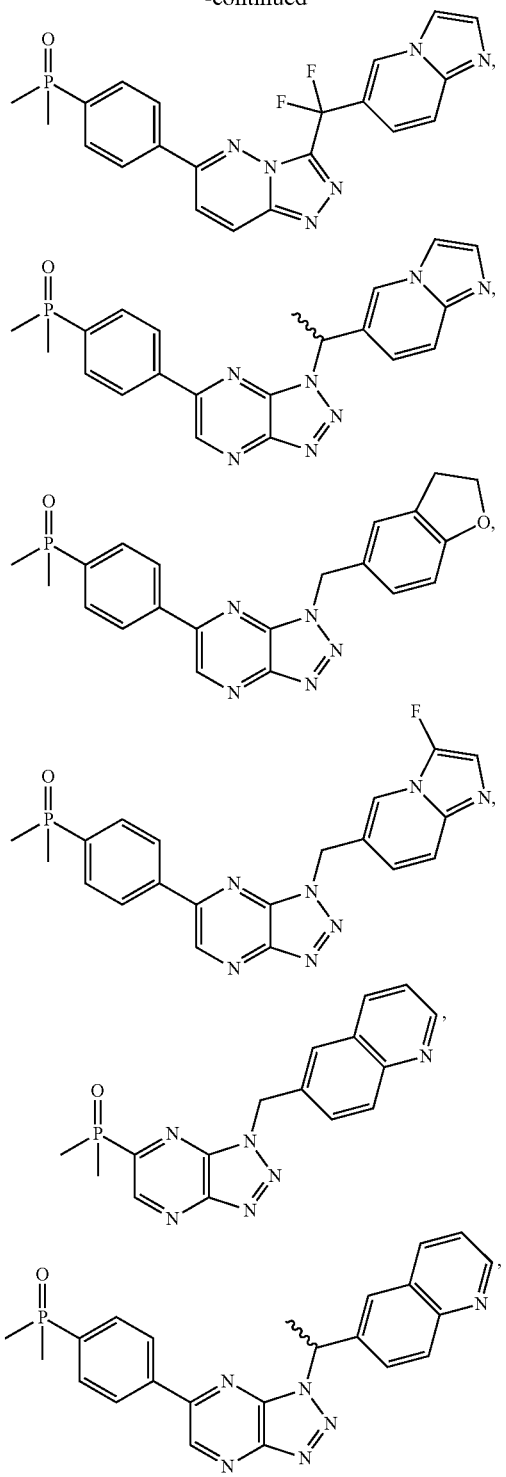

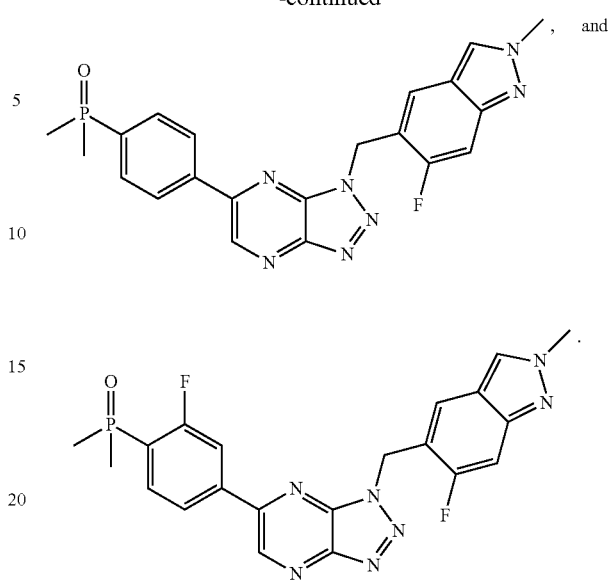

27. A pharmaceutical composition comprising a compound according to claim 1, or a pharmaceutically acceptable salt, solvate or prodrug thereof, and a pharmaceutically acceptable carrier.

28. A method of treating a disease or disorder in a subject, comprising administering to the subject a therapeutically effective amount of a compound according to claim 1, or a pharmaceutically acceptable salt, solvate or prodrug thereof, wherein the disease or disorder is associated with tyrosine kinase c-MET activity.

29. The method of claim 28, wherein the disease or disorder is selected from the group consisting of gastric cancer, lung cancer, colon cancer, breast cancer, pancreatic cancer, esophageal cancer, colorectal cancers, ovarian cancers, glioblastomas, hepatocellular cancer, melanoma, sarcoma, fibrosarcoma, osteoma, neuroblastoma, teratocarcinoma, retinoblastoma, rhabdomyosarcoma, hematopoietic malignancy, malignant ascites, atherosclerosis, and fibrosis of the lung.

30. The method of claim 28, wherein the disease or disorder is non-small cell lung cancer.

* * * * *